US008445283B2

(12) United States Patent
Connelly et al.

(10) Patent No.: US 8,445,283 B2
(45) Date of Patent: *May 21, 2013

(54) **METHODS FOR PRODUCING BIOLOGICAL SUBSTANCES IN ENZYME-DEFICIENT MUTANTS OF *ASPERGILLUS NIGER***

(75) Inventors: Mariah Connelly, Sacramento, CA (US); Howard Brody, Davis, CA (US)

(73) Assignee: Novozymes, Inc., Davis, CA (US)

( * ) Notice: Subject to any disclaimer, the term of this patent is extended or adjusted under 35 U.S.C. 154(b) by 184 days.

This patent is subject to a terminal disclaimer.

(21) Appl. No.: 12/823,046

(22) Filed: Jun. 24, 2010

(65) Prior Publication Data

US 2010/0323448 A1 Dec. 23, 2010

Related U.S. Application Data

(60) Division of application No. 11/837,279, filed on Aug. 10, 2007, now Pat. No. 7,771,971, which is a continuation of application No. 10/815,495, filed on Mar. 31, 2004, now Pat. No. 7,303,877.

(60) Provisional application No. 60/459,902, filed on Mar. 31, 2003.

(51) Int. Cl.
*C12N 15/74* (2006.01)
*C12N 1/14* (2006.01)

(52) U.S. Cl.
USPC .................. 435/471; 435/254.3; 435/69.1

(58) Field of Classification Search
None
See application file for complete search history.

(56) References Cited

U.S. PATENT DOCUMENTS

| | | | |
|---|---|---|---|
| 5,252,726 | A | 10/1993 | Woldike |
| 6,432,672 | B1 | 8/2002 | Selten et al. |
| 2003/0162218 | A1 | 8/2003 | Emalfarb et al. |
| 2004/0142364 | A1 | 7/2004 | Hjort et al. |

FOREIGN PATENT DOCUMENTS

| WO | WO 00/50576 | 8/2000 |
|---|---|---|
| WO | WO 01/68864 | 9/2001 |

OTHER PUBLICATIONS

Boel et al., Glucoamylases G1 and G2 from *Aspergillus niger* are synthesized from two different but closely related mRNAs, *EMBO J.* 3: 1984, 1097-1102.

Boel et al., Two different types of intervening sequences in the glucoamylase gene from *Aspergillus niger*, *EMBO* J. 3: 1984, 1581-1585.

Fowler et al., Regulation of the glaA gene of *Aspergillus niger*, 1990, *Curr. Genet.* 18: 537-545.

Korman et al., Cloning, characterization, and expression of two α-amylase genes from *Aspergillus niger* var. awamori, 1990, *Curr. Genet.* 17: 203-217.

Pedersen et al., Construction and characterization of an Oxalic Acid nonproducing strain of *Aspergillus niger*, 2000, *Metabolic Engineering* 2: 34-41.

Conesa et al., Studies on the productionof fungal peroxidases in *Aspergillus niger*, Applied Environmental Microbiology, 2000, v. 66, pp. 3016-3023.

Broekhuijsen et al., Secretion of heterologous proteins by *Aspergillus niger*: Production of active human interleukin-6 in a protease-deficient mutant by KEX2-like processing of a glucoamylase-hIL6 fusion protein, Journal of Biotechnology, 1993, v. 31, pp. 135-145.

MacKenzie et al., Molecular basis of glucoamylase overproduction by a mutagenised industrial strain of *Aspergillus niger*, Enzyme and Microbial Technology, 2000, v. 26, pp. 193-200.

Weenink et al., A new method for screening and isolation of hypersecretion mutants in *Aspergillus niger*, Applied Microbial and Cell Physiology, 2006, v. 69, pp. 711-717.

Morimura et al, 1999, Genetic Engineering of White Shochu-Koji 105(5), 309-314.

*Primary Examiner* — Patricia A Duffy
(74) *Attorney, Agent, or Firm* — Robert L. Starnes

(57) ABSTRACT

The present invention relates to methods of producing a heterologous biological substance, comprising: (a) cultivating a mutant of a parent *Aspergillus niger* strain in a medium suitable for the production of the heterologous biological substance, wherein (i) the mutant strain comprises a first nucleotide sequence encoding the heterologous biological substance and one or more second nucleotide sequences comprising a modification of glaA and at least one of the genes selected from the group consisting of asa, amyA, amyB, prtT, and oah, and (ii) the mutant strain is deficient in the production of glucoamylase and at least one enzyme selected from the group consisting of acid stable alpha-amylase, neutral alpha-amylase A, and neutral alpha-amylase B, protease, and oxalic acid hydrolase compared to the parent *Aspergillus niger* strain when cultivated under identical conditions; and (b) recovering the heterologous biological substance from the cultivation medium. The present invention also relates to enzyme-deficient mutants of *Aspergillus niger* strains and methods for producing such mutants.

11 Claims, 14 Drawing Sheets ively. U.S. Pat. No. 7,303,877, which claims the...

METHODS FOR PRODUCING BIOLOGICAL SUBSTANCES IN ENZYME-DEFICIENT MUTANTS OF *ASPERGILLUS NIGER*

CROSS-REFERENCE TO RELATED APPLICATION

This application is a divisional of U.S. patent application Ser. No. 11/837,279, filed Aug. 10, 2007, which is a continuation of U.S. patent application Ser. No. 10/815,495, filed Mar. 31, 2004, now U.S. Pat. No. 7,303,877, which claims the benefit of U.S. Provisional Application No. 60/459,902, filed Mar. 31, 2003, which applications are incorporated herein by reference.

BACKGROUND OF THE INVENTION

1. Field of the Invention

The present invention relates to methods of producing heterologous biological substances in enzyme-deficient *Aspergillus niger* mutant strains, methods of obtaining the enzyme-deficient *Aspergillus niger* mutant strains, and the enzyme-deficient *Aspergillus niger* mutant strains.

2. Description of the Related Art

*Aspergillus niger* secretes large quantities of glucoamylase. However, *Aspergillus niger* hosts with the desirable traits of increased protein expression and secretion may not necessarily have the most desirable characteristics for successful fermentation. The fermentation may not be optimal because of the secretion of multiple enzymes requiring removal during the recovery and purification of a biological substance of interest or the enzymes may co-purify with the biological substance.

Boel et al., 1984, *EMBO J.* 3: 1097-1102, 1581-1585, disclose the cloning of the glucoamylase (glaA) gene of *Aspergillus niger*. Fowler et al., 1990, *Curr. Genet.* 18: 537-545 disclose the deletion of the glucoamylase (glaA) gene of *Aspergillus niger*.

Korman et al., 1990, *Curr. Genet.* 17: 203-217 disclose the cloning, characterization, and expression of two alpha-amylase genes (amyA and amyB) from *Aspergillus niger* var. *awamori*. U.S. Pat. No. 5,252,726 discloses the cloning of two full length neutral alpha-amylase genes from *Aspergillus niger*.

U.S. Pat. No. 5,252,726 discloses the cloning of a portion of an acid stable alpha-amylase gene (asa) from *Aspergillus niger*.

Pedersen et al., 2000, *Metabolic Engineering* 2: 34-41, and WO 00/50576 disclose the disruption of an oxaloacetate hydrolase (oah) gene encoding oxaloacetate hydrolase (EC 3.7.1.1) in a glucoamylase-producing strain of *Aspergillus niger*, wherein the resulting strain was incapable of producing oxalic acid.

WO 01/68864 discloses that prtT-disrupted *Aspergillus niger* strains are protease deficient, indicating that deletion of prtT expression in a host strain can result in an increase in the level of recoverable protein susceptible to proteolysis.

It is an object of the present invention to provide improved *Aspergillus niger* hosts which combine the capacity for expression of commercial quantities of a biological substance while being deficient in the production of enzymes which can complicate recovery and downstream processing of the biological substance of interest.

SUMMARY OF THE INVENTION

The present invention relates to methods of producing a heterologous biological substance, comprising:

(a) cultivating a mutant of a parent *Aspergillus niger* strain in a medium suitable for the production of the heterologous biological substance, wherein (i) the mutant strain comprises a first nucleotide sequence encoding the heterologous biological substance and one or more second nucleotide sequences comprising a modification of glaA and at least one of the genes selected from the group consisting of asa, amyA, amyB, prtT, and oah, and (ii) the mutant strain is deficient in the production of glucoamylase and at least one enzyme selected from the group consisting of acid stable alpha-amylase, neutral alpha-amylase A, and neutral alpha-amylase B, protease, and oxalic acid hydrolase compared to the parent *Aspergillus niger* strain when cultivated under identical conditions; and (b) recovering the heterologous biological substance from the cultivation medium.

The present invention also relates to enzyme-deficient *Aspergillus niger* mutant strains and methods for producing the enzyme-deficient *Aspergillus niger* mutant strains.

DETAILED DESCRIPTION OF THE INVENTION

Figure 1:
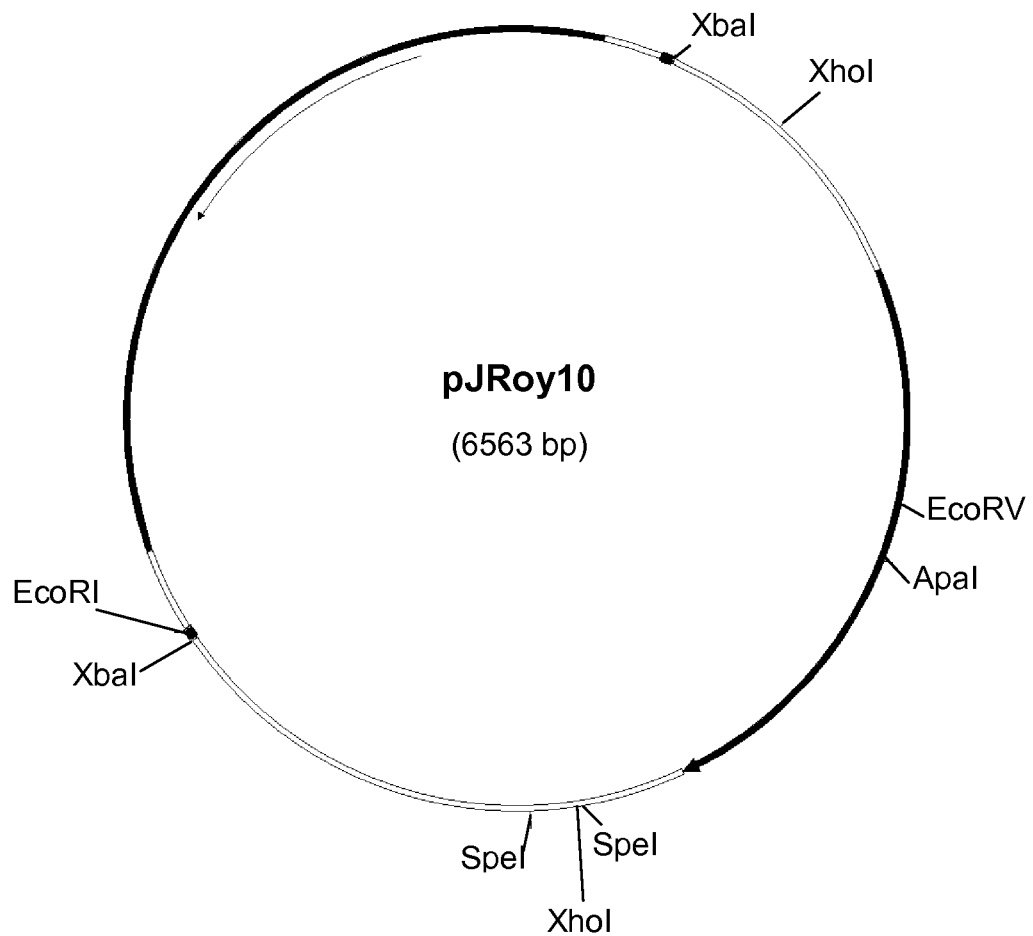
FIG. 1 shows a restriction map of pJRoy10.

The present invention relates to methods of producing a heterologous biological substance, comprising: (a) cultivating a mutant of a parent *Aspergillus niger* strain in a medium suitable for the production of the heterologous biological substance, wherein (i) the mutant strain comprises a first nucleotide sequence encoding the heterologous biological substance and one or more second nucleotide sequences comprising a modification of glaA and at least one of the genes selected from the group consisting of asa, amyA, amyB, prtT, and oah, and (ii) the mutant strain is deficient in the production of glucoamylase and at least one enzyme selected from the group consisting of acid stable alpha-amylase, neutral alpha-amylase A, and neutral alpha-amylase B, protease, and oxalic acid hydrolase compared to the parent *Aspergillus niger* strain when cultivated under identical conditions; and (b) recovering the heterologous biological substance from the cultivation medium.

An advantage of the present invention is the elimination or reduction of glucoamylase and at least one enzyme selected from the group consisting of acid stable alpha-amylase, neutral alpha-amylase A, and neutral alpha-amylase B, protease, and oxalic acid hydrolase in an *Aspergillus niger* fermentation broth simplifies downstream processing of heterologous biological substances.

The term "amyloglucosidase" is defined herein as a dextrin 6-alpha-D-glucanohydrolase activity which catalyses the endohydrolysis of 1,6-alpha-D-glucoside linkages at points of branching in chains of 1,4-linked alpha-D-glucose residues and terminal 1,4-linked alpha-D-glucose residues. For purposes of the present invention, glucoamylase activity is determined according to the procedure described by Fagershom and Kalkkinen, 1995, *Biotechnol. Appl. Biochem.* 21: 223-231, where the glucose produced by a glucoamylase from 0.1 M maltotriose is measured using a glucose oxidase assay kit (Sigma Chemical Co., St. Louis, Mo.) at pH 4, 25° C. One unit of glucoamylase activity is defined as 1.0 µmole of glucose produced per minute at 25° C., pH 4.

The term "alpha-amylase activity" is defined herein as a 1,4-alpha-D-glucan glucanohydrolase activity which catalyzes the endohydrolysis of polysaccharides with three or more alpha-1,4-linked glucose units in the presence of water to maltooligosaccharides.

The term "acid stable alpha-amylase activity" is defined herein as an alpha-amylase activity with optimal activity in the acid pH range. For purposes of the present invention, acid stable alpha-amylase activity is determined using 4,6-ethylidene (G7)-p-nitrophenyl (G1)-alpha-D-maltoheptaside as substrate using Sigma Chemical Co. Kit 577 at pH 4.0.

The term "neutral alpha-amylase activity" is defined herein as an alpha-amylase activity with optimal activity in the neutral pH range. For purposes of the present invention, neutral alpha-amylase activity is determined using 4,6-ethylidene (G7)-p-nitrophenyl (G1)-alpha-D-maltoheptaside as substrate using Sigma Chemical Co. Kit 577 at pH 7.0.

The term "oxalic acid hydrolase" is defined herein as an enzyme activity which catalyzes the conversion of oxaloacetate in the presence of water to oxalic acid and acetate. The enzyme is classified as belonging to EC 3.7.1.1. For purposes of the present invention, oxaloacetate hydrolase activity is determined according to the procedure described in the Examples section herein. One unit of oxaloacetate hydrolase activity is defined as 1.0 µmole of oxalic acid produced per minute at 30° C., pH 7.5.

The term "modification" is defined herein as an introduction, substitution, or removal of one or more nucleotides in a gene or a regulatory element required for the transcription or translation thereof, as well as a gene disruption, gene conversion, gene deletion, or random or specific mutagenesis of glaA and at least one of the genes selected from the group consisting of asa, amyA, amyB, prtT, and oah. The deletion of the glaA gene and asa, amyA, amyB, prtT, and/or oah gene(s) may be partial or complete. The modification results in a decrease or elimination in expression of glaA and at least one of the genes selected from the group consisting of asa, amyA, amyB, prtT, and oah.

In a preferred aspect, the modification results in the inactivation of glaA and at least one of the genes selected from the group consisting of asa, amyA, amyB, prtT, and oah. In another preferred aspect, the modification results in a decrease in expression of glaA and at least one of the genes selected from the group consisting of asa, amyA, amyB, prtT, and oah. In another preferred aspect, the modification results in the expression of glaA and at least one of the genes selected from the group consisting of asa, amyA, amyB, prtT, and oah being decreased, eliminated, or a combination thereof.

In a preferred aspect, the mutant comprises a modification of glaA and asa. In another preferred aspect, the mutant comprises a modification of glaA and amyA. In another preferred aspect, the mutant comprises a modification of glaA and amyB. In another preferred aspect, the mutant comprises a modification of glaA and prtT. In another preferred aspect, the mutant comprises a modification of glaA and oah.

In another preferred aspect, the mutant comprises a modification of glaA, asa, and amyA. In another preferred aspect, the mutant comprises a modification of glaA, asa, and amyB. In another preferred aspect, the mutant comprises a modification of glaA, asa, and prtT.

In another preferred aspect, the mutant comprises a modification of glaA, asa, and oah. In another preferred aspect, the mutant comprises a modification of glaA, amyA, and amyB. In another preferred aspect, the mutant comprises a modification of glaA, amyA, and prtT. In another preferred aspect, the mutant comprises a modification of glaA, amyA, and oah. In another preferred aspect, the mutant comprises a modification of glaA, amyB, and prtT. In another preferred aspect, the mutant comprises a modification of glaA, amyB, and oah. In another preferred aspect, the mutant comprises a modification of glaA, prtT, and oah.

In another preferred aspect, the mutant comprises a modification of glaA, asa, amyA, and amyB. In another preferred aspect, the mutant comprises a modification of glaA, asa, amyB, and prtT. In another preferred aspect, the mutant comprises a modification of glaA, asa, prtT, and oah. In another preferred aspect, the mutant comprises a modification of glaA, asa, amyA, and prtT. In another preferred aspect, the mutant comprises a modification of glaA, asa, amyA, and oah. In another preferred aspect, the mutant comprises a modification of glaA, amyA, amyB, and prtT. In another preferred aspect, the mutant comprises a modification of glaA, asa, amyB, and oah. In another preferred aspect, the mutant comprises a modification of glaA, amyA, prtT, and oah. In another preferred aspect, the mutant comprises a modification of glaA, amyA, amyB, and oah. In another preferred aspect, the mutant comprises a modification of glaA, amyB, prtT, and oah.

In another preferred aspect, the mutant comprises a modification of glaA, asa, amyA, amyB, and prtT. In another preferred aspect, the mutant comprises a modification of glaA, asa, amyB, prtT, and oah. In another preferred aspect, the mutant comprises a modification of glaA, amyA, amyB, prtT, and oah. In another preferred aspect, the mutant comprises a modification of glaA, asa, amyA, amyB, and oah. In another preferred aspect, the mutant comprises a modification of glaA, asa, amyA, prtT, and oah.

In another preferred aspect, the mutant comprises a modification of glaA, asa, amyA, amyB, prtT, and oah.

The term "deficient" is defined herein as an *Aspergillus niger* mutant strain which produces no detectable glucoamylase and at least one enzyme selected from the group consisting of acid stable alpha-amylase, neutral alpha-amylase A, and neutral alpha-amylase B, protease, and oxalic acid hydrolase compared to the parent *Aspergillus niger* strain when cultivated under identical conditions, or, in the alternative, produces preferably at least 25% less, more preferably at least 50% less, even more preferably at least 75% less, and most preferably at least 95% less glucoamylase and at least one enzyme selected from the group consisting of acid stable alpha-amylase, neutral alpha-amylase A, and neutral alpha-amylase B, protease, and oxalic acid hydrolase compared to the parent *Aspergillus niger* strain when cultivated under identical conditions. The level of enzyme produced by an *Aspergillus niger* mutant strain of the present invention may be determined using methods described herein or known in the art.

In the methods of the present invention, the parent *Aspergillus niger* strain may be a wild-type *Aspergillus niger* strain or a mutant thereof. It will be understood that the term "*Aspergillus niger*" also includes varieties of *Aspergillus niger* (See, for example, Robert A. Samsom and John I. Pitt, editors, *Integration of Modern Taxonomic Methods for Penicillium and Aspergillus Classification*, Harwood Academic Publishers, The Netherlands). In a preferred aspect, the parent *Aspergillus niger* strain is *Aspergillus niger* DSM 12665.

The enzyme-deficient *Aspergillus niger* mutant strain may be constructed by reducing or eliminating expression of glaA and at least one of the genes selected from the group consisting of asa, amyA, amyB, prtT and oah using methods well known in the art, for example, insertions, disruptions, replacements, or deletions. The portion of the gene to be modified or inactivated may be, for example, the coding region or a regulatory element required for expression of the coding region. An example of such a regulatory or control sequence of a gene may be a promoter sequence or a functional part thereof, i.e., a part which is sufficient for affecting expression of the gene. Other control sequences for possible modification include, but are not limited to, a leader, propeptide sequence, signal sequence, transcription terminator, and transcriptional activator.

The *Aspergillus niger* mutant strains may be constructed by gene deletion techniques to eliminate or reduce the expression of glaA and at least one of the genes selected from the group consisting of asa, amyA, amyB, prtT and oah. Gene deletion techniques enable the partial or complete removal of the gene(s) thereby eliminating their expression. In such methods, the deletion of the gene(s) may be accomplished by homologous recombination using a plasmid that has been constructed to contiguously contain the 5' and 3' regions flanking the gene.

The *Aspergillus niger* mutant strains may also be constructed by introducing, substituting, and/or removing one or more nucleotides in the gene or a regulatory element thereof required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, *Science* 229: 4719; Lo et al., 1985, *Proceedings of the National Academy of Sciences USA* 81: 2285; Higuchi et al., 1988, *Nucleic Acids Research* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The *Aspergillus niger* mutant strains may also be constructed by gene disruption techniques by inserting into the gene of interest an integrative plasmid containing a nucleic acid fragment homologous to the gene which will create a duplication of the region of homology and incorporate vector DNA between the duplicated regions. Such gene disruption can eliminate gene expression if the inserted vector separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The *Aspergillus niger* mutant strains may also be constructed by the process of gene conversion (see, for example, Iglesias and Trautner, 1983, *Molecular General Genetics* 189: 73-76). For example, in the gene conversion method, a nucleotide sequence corresponding to the gene(s) is mutagenized in vitro to produce a defective nucleotide sequence which is then transformed into the parent *Aspergillus niger* strain to produce a defective gene. By homologous recombination, the defective nucleotide sequence replaces the endogenous gene. It may be desirable that the defective gene or gene fragment also comprises a marker which may be used for selection of transformants containing the defective gene.

The *Aspergillus niger* mutant strains may also be constructed by established anti-sense techniques using a nucleotide sequence complementary to the nucleotide sequence of the gene (Parish and Stoker, 1997, *FEMS Microbiology Letters* 154: 151-157). More specifically, expression of the gene by an *Aspergillus niger* strain may be reduced or eliminated by introducing a nucleotide sequence complementary to the nucleotide sequence of the gene, which may be transcribed in the strain and is capable of hybridizing to the mRNA produced in the strain. Under conditions allowing the complementary anti-sense nucleotide sequence to hybridize to the mRNA, the amount of protein translated is thus reduced or eliminated.

The *Aspergillus niger* mutant strains may be further constructed by random or specific mutagenesis using methods well known in the art, including, but not limited to, chemical mutagenesis (see, for example, Hopwood, *The Isolation of Mutants in Methods in Microbiology*(J. R. Norris and D. W. Ribbons, eds.) pp 363-433, Academic Press, New York, 1970) and transposition (see, for example, Youngman et al., 1983, *Proc. Natl. Acad. Sci. USA* 80: 2305-2309). Modification of the gene may be performed by subjecting the parent strain to mutagenesis and screening for mutant strains in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of a gene.

In a preferred aspect, glaA comprises a nucleotide sequence having at least 70%, preferably at least 75%, more preferably at least 80%, even more preferably at least 85%, most preferably at least 90%, and even most preferably at least 95% identity to SEQ ID NO: 5. In a most preferred aspect, glaA comprises the nucleotide sequence of SEQ ID NO: 5. In another most preferred aspect, glaA consists of the nucleotide sequence of SEQ ID NO: 5.

In another preferred aspect, glaA comprises a nucleotide sequence which hybridizes under very low stringency conditions, preferably low stringency conditions, more preferably medium stringency conditions, more preferably medium-high stringency conditions, even more preferably high stringency conditions, and most preferably very high stringency conditions with SEQ ID NO: 5.

In a preferred aspect, amyA comprises a nucleotide sequence having at least 70%, preferably at least 75%, more preferably at least 80%, even more preferably at least 85%, most preferably at least 90%, and even most preferably at least 95% identity to SEQ ID NO: 21. In a most preferred aspect, amyA comprises the nucleotide sequence of SEQ ID NO: 21. In another most preferred aspect, amyA consists of the nucleotide sequence of SEQ ID NO: 21.

In another preferred aspect, amyA comprises a nucleotide sequence which hybridizes under very low stringency conditions, preferably low stringency conditions, more preferably medium stringency conditions, more preferably medium-high stringency conditions, even more preferably high stringency conditions, and most preferably very high stringency conditions with SEQ ID NO: 21.

In a preferred aspect, amyB comprises a nucleotide sequence having at least 70%, preferably at least 75%, more preferably at least 80%, even more preferably at least 85%, most preferably at least 90%, and even most preferably at least 95% identity to SEQ ID NO: 17. In a most preferred aspect, amyB comprises the nucleotide sequence of SEQ ID NO: 17. In another most preferred aspect, amyB consists of the nucleotide sequence of SEQ ID NO: 17.

In another preferred aspect, amyB comprises a nucleotide sequence which hybridizes under very low stringency conditions, preferably low stringency conditions, more preferably medium stringency conditions, more preferably medium-high stringency conditions, even more preferably high stringency conditions, and most preferably very high stringency conditions with SEQ ID NO: 17.

In a preferred aspect, oah comprises a nucleotide sequence having at least 70%, preferably at least 75%, more preferably at least 80%, even more preferably at least 85%, most preferably at least 90%, and even most preferably at least 95% identity to SEQ ID NO: 23. In a most preferred aspect, oah comprises the nucleotide sequence of SEQ ID NO: 23. In another most preferred aspect, oah consists of the nucleotide sequence of SEQ ID NO: 23.

In another preferred aspect, oah comprises a nucleotide sequence which hybridizes under very low stringency conditions, preferably low stringency conditions, more preferably medium stringency conditions, more preferably medium-high stringency conditions, even more preferably high stringency conditions, and most preferably very high stringency conditions with SEQ ID NO: 23.

In a preferred aspect, prtT comprises a nucleotide sequence having at least 70%, preferably at least 75%, more preferably at least 80%, even more preferably at least 85%, most preferably at least 90%, and even most preferably at least 95% identity to SEQ ID NO:13. In a most preferred aspect, prtT comprises the nucleotide sequence of SEQ ID NO:13. In another most preferred aspect, prtT consists of the nucleotide sequence of SEQ ID NO:13.

In another preferred aspect, prtT comprises a nucleotide sequence which hybridizes under very low stringency conditions, preferably low stringency conditions, more preferably medium stringency conditions, more preferably medium-high stringency conditions, even more preferably high stringency conditions, and most preferably very high stringency conditions with SEQ ID NO:13.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

The nucleotide sequences disclosed herein or a subsequence thereof, as well as the amino acid sequence thereof or a fragment thereof, may be used to design a nucleic acid probe to identify and clone DNA encoding enzymes involved in the biosynthesis of hyaluronic acid from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin).

Thus, a genomic DNA or cDNA library prepared from such other organisms may be screened for DNA which hybridizes with the probes described above and which encodes an enzyme in the biosynthetic pathway of hyaluronic acid. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with the nucleotide sequences disclosed herein or subsequences thereof, the carrier material is used in a Southern blot. For purposes of the present invention, hybridization indicates that the nucleic acid sequence hybridizes to a labeled nucleic acid probe corresponding to the nucleotide sequences disclosed herein, its complementary strand, or a subsequence thereof, under very low to very high stringency conditions. Molecules to which the nucleic acid probe hybridizes under these conditions are detected using X-ray film.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

A nucleotide sequence homologous or complementary to the nucleotide sequences described herein involved in the production of the enzyme of interest may be used from other microbial sources which produce the enzyme to modify the corresponding gene in the *Aspergillus niger* strain of choice.

In a preferred aspect, the modification of a gene involved in the production of an enzyme in the *Aspergillus niger* mutant strain is unmarked with a selectable marker.

Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

It will be understood that the methods of the present invention are not limited to a particular order for obtaining the *Aspergillus niger* mutant strain. The modification of a gene involved in the production of an enzyme may be introduced into the parent strain at any step in the construction of the strain for the production of a biological substance. It is preferred that the *Aspergillus niger* mutant strain has already been made enzyme-deficient prior to the introduction of a gene encoding a heterologous biological substance.

In a further aspect of the present invention, the mutants of *Aspergillus niger* strains may contain additional modifications, e.g., deletions or disruptions, of other genes, which may encode substances detrimental to the production, recovery or application of a particular biological substance.

In a preferred aspect, the *Aspergillus niger* strain further comprises a modification, e.g., disruption or deletion, of one or more genes encoding a proteolytic activity. In a more preferred aspect, the proteolytic activity is selected from the group consisting of an aminopeptidase, dipeptidylaminopeptidase, tripeptidylaminopeptidase, carboxypeptidase, aspergillopepsin, serine protease, metalloprotease, cysteine protease, and vacuolar protease.

In another preferred aspect, the *Aspergillus niger* strain further comprises a modification, e.g., disruption or deletion, of one or more genes encoding an enzyme selected from the group consisting of a carbohydrase, carboxypeptidase, catalase, cellulase, chitinase, cutinase, cyclodextrin glycosyltransferase, deoxyribonuclease, esterase, galactosidase, beta-galactosidase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, ribonuclease, transferase, alpha-1,6-transglucosidase, alpha-1,6-transglucosidase, transglutaminase, and xylanase.

In the methods of the present invention, the *Aspergillus niger* mutant strain preferably produces at least the same amount of the biological substance as the corresponding parent *Aspergillus niger* strain when cultured under identical production conditions. In a more preferred aspect, the mutant strain produces at least 25% more, preferably at least 50% more, more preferably at least 75% more, and most preferably at least 100% more of the biological substance than the corresponding parent *Aspergillus niger* strain when cultured under identical production conditions.

The *Aspergillus niger* mutant strains are cultivated in a nutrient medium suitable for production of the heterologous biological substance using methods known in the art. For example, the strain may be cultivated by shake flask cultivation, small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted biological substance can be recovered directly from the medium. If the biological substance is not secreted, it may be obtained from cell lysates.

The biological substances may be detected using methods known in the art that are specific for the biological substances. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

The resulting biological substance may be isolated by methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989). A metabolite of interest may be isolated from a cultivation medium by, for example, extraction, precipitation, or differential solubility, or any method known in the art. The isolated metabolite may then be further purified using methods suitable for metabolites.

The heterologous biological substance may be any biopolymer or metabolite. The biological substance may be encoded by a single gene or a series of genes composing a biosynthetic or metabolic pathway. Thus, the term "first nucleotide sequence encoding the heterologous biological substance" will be understood to encompass one or more genes involved in the production of the biological substance. The term "heterologous biological substance" is defined herein as a biological substance which is not native to the host strain; a native biological substance in which structural modifications have been made to alter the native biological substance, e.g., the protein sequence of a native polypeptide; or a native biological substance whose expression is quantitatively altered as a result of a manipulation of the nucleotide sequence or host strain by recombinant DNA techniques, e.g., a stronger promoter.

In the methods of the present invention, the biopolymer may be any biopolymer. The term "biopolymer" is defined herein as a chain (or polymer) of identical, similar, or dissimilar subunits (monomers). The biopolymer may be, but is not limited to, a nucleic acid, polyamine, polyol, polypeptide (or polyamide), or polysaccharide.

In a preferred aspect, the biopolymer is a polypeptide. The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include hybrid polypeptides, which comprise a combination of partial or complete polypeptide sequences obtained from at least two different polypeptides wherein one or more may be heterologous to the *Aspergillus niger* strain. Polypeptides further include naturally occurring allelic and engineered variations of the above-mentioned polypeptides and hybrid polypeptides.

Preferably, the heterologous polypeptide is an antibody, antigen, antimicrobial peptide, enzyme, growth factor, hormone, immunodilator, neurotransmitter, receptor, reporter protein, structural protein, or transcription factor.

In a preferred aspect, the heterologous polypeptide is an oxidoreductase, transferase, hydrolase, lyase, isomerase, or ligase. In a more preferred aspect, the polypeptide is an alpha-glucosidase, aminopeptidase, alpha-amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred aspect, the polypeptide is a collagen or gelatin.

In a preferred aspect, the biopolymer is a polysaccharide. The polysaccharide may be any polysaccharide, including, but not limited to, a mucopolysaccharide or a nitrogen-containing polysaccharide. In a more preferred aspect, the polysaccharide is hyaluronic acid. "Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. In another more preferred aspect, the polysaccharide is chitin. In another more preferred aspect, the polysaccharide is heparin.

In the methods of the present invention, the metabolite may be any metabolite. The metabolite may be encoded by one or more genes. The term "metabolite" encompasses both primary and secondary metabolites. Primary metabolites are products of primary or general metabolism of a strain, which are concerned, for example, with energy metabolism, growth, and structure. Secondary metabolites are products of secondary metabolism (see, for example, R. B. Herbert, *The Biosynthesis of Secondary Metabolites*, Chapman and Hall, New York, 1981).

The primary metabolite may be, but is not limited to, an amino acid, fatty acid, nucleoside, nucleotide, sugar, triglyceride, or vitamin.

The secondary metabolite may be, but is not limited to, an alkaloid, coumarin, flavonoid, polyketide, quinine, steroid, peptide, or terpene. In a preferred aspect, the secondary metabolite is an antibiotic, antifeedant, attractant, bacteriocide, fungicide, hormone, insecticide, or rodenticide.

In the methods of the present invention, the mutant of the *Aspergillus niger* strain is a recombinant strain, comprising a nucleotide sequence encoding a heterologous biological substance, e.g., polypeptide, which is advantageously used in the recombinant production of the biological substance. The strain is preferably transformed with a vector comprising the nucleotide sequence encoding the heterologous biological substance followed by integration of the vector into the chromosome. "Transformation" means introducing a vector comprising the nucleotide sequence into a host strain so that the vector is maintained as a chromosomal integrant or as a self-replicating extra-chromosomal vector. Integration is generally considered to be an advantage as the nucleotide sequence is more likely to be stably maintained in the strain. Integration of the vector into the chromosome can occur by homologous recombination, non-homologous recombination, or transposition.

The nucleotide sequence encoding a heterologous biological substance may be obtained from any prokaryotic, eukaryotic, or other source, e.g., archaeabacteria. For purposes of the present invention, the term "obtained from" as used herein in connection with a given source shall mean that the biological substance is produced by the source or by a strain in which a gene from the source has been inserted.

In the methods of the present invention, the mutants of *Aspergillus niger* strains may also be used for the recombinant production of biological substances which are native to the *Aspergillus niger* strain. The native biological substance may be produced by recombinant means by, for example, placing a gene encoding the biological substance under the control of a different promoter to enhance expression of the substance, expediting its export outside the strain by use of, for example, a signal sequence, or increasing the copy number of a gene encoding the biological substance normally produced by the *Aspergillus niger* strain. Thus, the present invention also encompasses, within the scope of the term "heterologous biological substances," such recombinant production of native biological substances, to the extent that such expression involves the use of genetic elements not native to the *Aspergillus niger* strain, or use of native elements which have been manipulated to function in a manner that do not normally occur in the host strain.

The techniques used to isolate or clone a nucleotide sequence encoding a biological substance are known in the art and include isolation from genomic DNA, preparation from cDNA, or a combination thereof. The cloning of a nucleotide sequence from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleotide sequence encoding the biological substance, insertion of the fragment into a vector molecule, and incorporation of the recombinant vector into an *Aspergillus niger* strain where multiple copies or clones of the nucleotide sequence will be replicated. The nucleotide sequence may be of genomic, cDNA, RNA, semisynthetic, synthetic origin, or any combinations thereof.

In the methods of the present invention, the biological substance may also be a fused polypeptide in which another polypeptide is fused at the N-terminus or the C-terminus of the polypeptide or fragment thereof. A fused polypeptide is produced by fusing a nucleotide sequence (or a portion thereof) encoding one polypeptide to a nucleotide sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence. The term "coding sequence" is defined herein as a sequence which is transcribed into mRNA and translated into a biological substance of interest when placed under the control of the below mentioned control sequences. The boundaries of the coding sequence are generally determined by an open reading frame, which usually begins with the ATG start codon or alternative start codons such as GTG and TTG. A coding sequence can include, but is not limited to, DNA, cDNA, and recombinant nucleotide sequences.

An isolated nucleotide sequence encoding a biological substance may be manipulated in a variety of ways to provide for expression of the biological substance. Manipulation of the nucleotide sequence prior to its insertion into a vector may be desirable or necessary depending on the expression vector or *Aspergillus niger* host strain. The techniques for modifying nucleotide sequences utilizing cloning methods are well known in the art.

A nucleic acid construct comprising a nucleotide sequence encoding a biological substance may be operably linked to one or more control sequences capable of directing the expression of the coding sequence in a mutant *Aspergillus niger* strain of the present invention under conditions compatible with the control sequences.

The term "control sequences" is defined herein to include all components which are necessary or advantageous for expression of the coding sequence of a nucleotide sequence. Each control sequence may be native or foreign to the nucleotide sequence encoding the biological substance. Such control sequences include, but are not limited to, a leader, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a biological substance.

The control sequence may be an appropriate promoter sequence, which is recognized by an *Aspergillus niger* strain for expression of the nucleotide sequence. The promoter sequence contains transcription control sequences which mediate the expression of the biological substance. The promoter may be any nucleic acid sequence which shows transcriptional activity in the mutant *Aspergillus niger* strain and may be obtained from genes encoding extracellular or intracellular biological substances either homologous or heterologous to the *Aspergillus niger* strain.

Examples of suitable promoters for directing the transcription of the nucleic acid constructs in the methods of the present invention are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof. Particularly preferred promoters are the glucoamylase, TAKA alpha-amylase, and NA2-tpi promoters.

The control sequence may also be a suitable transcription terminator sequence, a sequence recognized by an *Aspergillus niger* strain to terminate transcription. The terminator sequence is operably linked to the 3' terminus of the nucleotide sequence encoding the heterologous biological substance. Any terminator which is functional in an *Aspergillus niger* strain may be used in the present invention.

Preferred terminators are obtained from the genes encoding *Aspergillus oryzae* TAKA alpha-amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of a mRNA which is important for translation by a *Aspergillus niger* strain. The leader sequence is operably linked to the 5' terminus of the nucleotide sequence encoding the heterologous biological substance. Any leader sequence which is functional in the *Aspergillus niger* strain may be used in the present invention.

Preferred leaders are obtained from the genes encoding *Aspergillus oryzae* TAKA alpha-amylase and *Aspergillus nidulans* triose phosphate isomerase.

The control sequence may also be a polyadenylation sequence, a sequence which is operably linked to the 3' terminus of the nucleotide sequence and which, when transcribed, is recognized by an *Aspergillus niger* strain as a signal to add polyadenosine residues to transcribed mRNA. Any polyadenylation sequence which is functional in the *Aspergillus niger* strain may be used in the present invention.

Preferred polyadenylation sequences are obtained from the genes encoding *Aspergillus oryzae* TAKA alpha-amylase, *Aspergillus niger* glucoamylase, *Aspergillus nidulans* anthranilate synthase, and *Aspergillus niger* alpha-glucosidase.

The control sequence may also be a signal peptide coding region that codes for an amino acid sequence linked to the amino terminus of the heterologous polypeptide and directs the encoded polypeptide into the strain's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed heterologous polypeptide into the secretory pathway of an *Aspergillus niger* strain may be used in the present invention.

Effective signal peptide coding regions for *Aspergillus niger* host strains are the signal peptide coding regions obtained from the genes for *Aspergillus oryzae* TAKA alpha-amylase, *Aspergillus niger* neutral alpha-amylase, *Aspergillus niger* glucoamylase, *Rhizomucor miehei* aspartic proteinase, *Humicola insolens* cellulase, and *Humicola lanuginosa* lipase.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature, active polypeptide by catalytic or autocatalytic cleavage of the propeptide from the propolypeptide. The propeptide coding region may be obtained from the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

The nucleic acid constructs may also comprise one or more nucleotide sequences which encode one or more factors that are advantageous for directing the expression of the heterologous biological substance, e.g., a transcriptional activator (e.g., a trans-acting factor), a chaperone, and a processing protease. Any factor that is functional in an *Aspergillus niger* strain may be used in the present invention. The nucleic acids encoding one or more of these factors are not necessarily in tandem with the nucleotide sequence encoding the heterologous biological substance.

It may also be desirable to add regulatory sequences which allow regulation of the expression of a heterologous biological substance relative to the growth of the *Aspergillus niger* strain. Examples of regulatory systems are those which cause the expression of the gene to be turned on or off in response to a chemical or physical stimulus, including the presence of a regulatory compound. The TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification, e.g., the metallothionein genes which are amplified with heavy metals. In these cases, the nucleotide sequence encoding the heterologous biological substance would be operably linked with the regulatory sequence.

In the methods of the present invention, a recombinant expression vector comprising a nucleotide sequence, a promoter, and transcriptional and translational stop signals may be used for the recombinant production of a polypeptide or other biological substance. The various nucleic acids and control sequences described above may be joined together to produce a recombinant expression vector which may include one or more convenient restriction sites to allow for insertion or substitution of the nucleotide sequence encoding the polypeptide or biological substance at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector which can be conveniently subjected to recombinant DNA procedures and can bring about the expression of the nucleotide sequence. The choice of the vector will typically depend on the compatibility of the vector with the *Aspergillus niger* strain into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the *Aspergillus niger* strain, is integrated into the genome and replicated together with the chromosome(s) into which it has been integrated. The vector system may be a single vector or plasmid or two or more vectors or plasmids which together contain the total DNA to be introduced into the genome of the *Aspergillus niger* strain, or a transposon.

The vectors may be integrated into the strain's genome when introduced into an *Aspergillus niger* strain. For integration into the genome of a mutant *Aspergillus niger* strain of the present invention, the vector may rely on the nucleotide sequence encoding the heterologous biological substance or any other element of the vector for stable integration of the vector into the genome by homologous or nonhomologous recombination. Alternatively, the vector may contain additional nucleotide sequences for directing integration by homologous recombination into the genome of the *Aspergillus niger* strain. The additional nucleotide sequences enable the vector to be integrated into the genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequences that are homologous with the target sequence in the genome of the *Aspergillus niger*. Furthermore, the integrational elements may be non-encoding or encoding nucleotide sequences. On the other hand, the vector may be integrated into the genome of the strain by non-homologous recombination.

For autonomous replication, the vector may further comprise an origin of replication enabling the vector to replicate autonomously in the *Aspergillus niger* in question.

The various nucleic acids and control sequences described above may be joined together to produce a recombinant expression vector which may include one or more convenient restriction sites to allow for insertion or substitution of the nucleotide sequence encoding the heterologous biological substance at such sites. Alternatively, the nucleotide sequence encoding the heterologous biological substance may be expressed by inserting the sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The vectors preferably contain one or more selectable markers which permit easy selection of transformed *Aspergillus niger* strains. A selectable marker is a gene the product of which provides for biocide or viral resistance, resistance to heavy metals, prototrophy to auxotrophs, and the like. A selectable marker for use in an *Aspergillus niger* host strain may be selected from the group including, but not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus niger* strain are the amdS and pyrG genes of *Aspergillus nidulans* or *Aspergillus oryzae* and the bar gene of *Streptomyces hygroscopicus*.

The vectors preferably contain an element(s) that permits stable integration of the vector into the genome or autonomous replication of the vector in the strain independent of the genome of the strain.

"Introduction" means introducing a vector comprising the nucleotide sequence into an *Aspergillus niger* strain so that the vector is maintained as a chromosomal integrant or as a self-replicating extra-chromosomal vector. Integration is generally considered to be an advantage as the nucleotide sequence is more likely to be stably maintained in the strain. Integration of the vector into the chromosome occurs by homologous recombination, non-homologous recombination, or transposition.

The introduction of an expression vector into an *Aspergillus niger* host strain may involve a process consisting of protoplast formation, transformation of the protoplasts, and regeneration of the strain wall in a manner known per se. Suitable procedures for transformation of *Aspergillus* host strains are described in EP 238 023 and Yelton et al., 1984, *Proceedings of the National Academy of Sciences USA* 81: 1470-1474.

The procedures used to ligate the elements described herein to construct the recombinant expression vectors are well known to one skilled in the art (see, e.g., J. Sambrook, E. F. Fritsch, and T. Maniatus, 1989, *Molecular Cloning, A Laboratory Manual*, 2d edition, Cold Spring Harbor, N.Y.).

In another aspect of the present invention, the mutant *Aspergillus niger* strain may further contain modifications of one or more third nucleotide sequences which encode substances that may be detrimental to the production, recovery, and/or application of the heterologous biological substance of interest. The modification reduces or eliminates expression of the one or more third nucleotide sequences resulting in a mutant strain which may produce more of the heterologous biological substance than the mutant strain without the modification of the third nucleotide sequence when cultured under identical conditions.

The third nucleotide sequence may, for example, encode an enzyme. For example, the enzyme may be an aminopeptidase, alpha-amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, or xylanase. The third nucleotide sequence preferably encodes a proteolytic enzyme, e.g., an aminopeptidase, carboxypeptidase, or protease.

The present invention also relates to methods of obtaining a mutant of a parent *Aspergillus niger* strain, comprising: (a) introducing into the *Aspergillus niger* strain a first nucleotide sequence comprising a modification of glaA and at least one of the genes selected from the group consisting of asa, amyA, amyB, prtT and oah, which are involved in the production of glucoamylase, protease, oxalic acid hydrolase, acid stable alpha-amylase, neutral alpha-amylase A, and neutral alpha-amylase B, respectively; and (b) identifying the mutant strain from step (a) comprising the modified nucleotide sequence, wherein the mutant strain is deficient in the production of glucoamylase and at least one enzyme selected from the group consisting of acid stable alpha-amylase, neutral alpha-amylase A, and neutral alpha-amylase B, protease, and oxalic acid hydrolase compared to the parent *Aspergillus niger* strain when cultivated under identical conditions.

The present invention further relates to mutants of a parent *Aspergillus niger* strain, comprising a first nucleotide sequence encoding a heterologous biological substance and one or more second nucleotide sequences comprising a modification of glaA and at least one of the genes selected from the group consisting of asa, amyA, amyB, prtT and oah, which are involved in the production of glucoamylase, protease, oxalic acid hydrolase, acid stable alpha-amylase, neutral alpha-amylase A, and neutral alpha-amylase B, respectively, wherein the mutant strain is deficient in the production of glucoamylase and at least one enzyme selected from the group consisting of acid stable alpha-amylase, neutral alpha-amylase A, and neutral alpha-amylase B, protease, and oxalic acid hydrolase compared to the parent *Aspergillus niger* strain when cultivated under identical conditions.

The present invention is further described by the following examples which should not be construed as limiting the scope of the invention.

EXAMPLES

All primers and oligos were supplied by MWG Biotech, Inc., High Point, N.C.

DNA sequencing was conducted with an ABI 3700 Sequencing (Applied Biosystems, Inc., Foster City, Calif.).

Strains

All strains are derived from *Aspergillus niger* Bo-1 (DSM 12665). *Aspergillus niger* Bo-1 comprises a mutation of the alpha-1,6-transglucosidase gene resulting in no alpha-1,6-transglucosidase activity.

Media and Solutions

Minimal media was composed per liter of 6 g of $NaNO_3$, 0.52 g of KCl, 1.52 g of $KH_2PO_4$, 20 g of Noble Agar, 10 g of glucose, 0.5 g of $MgSO_4.7H_2O$, and 1 ml of Cove trace elements.

Cove plates were composed per liter of 342.3 g of sucrose, 20 ml of Cove salts (50×), 10 mM acetamide, 15 mM CsCl, and 25 g of Noble agar.

50× Cove salt solution was composed per liter of 26 g of KCl, 26 g of $MgSO_4$, 76 g of $KH_2PO_4$, and 50 ml of Cove trace elements.

Cove trace elements solution was composed per liter of 0.004 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

AMG trace metals solution was composed per liter of 14.3 g of $ZnSO_4.7H_2O$, 2.5 g of $CuSO_4.5H_2O$, 0.5 g of $NiCl_2$, 13.8 g of $FeSO_4$, 8.5 g of $MnSO_4$, and 3.0 g of citric acid.

YP medium was composed per liter of 10 g of yeast extract and 20 g of Bacto peptone.

STC is composed of 0.8 M sorbitol, 50 mM Tris, pH 8, and 50 mM $CaCl_2$.

SPTC was composed per liter of 40% PEG 4000, 0.8 M sorbitol, 50 mM Tris, pH 8, 50 mM $CaCl_2$.

SPC was composed per liter of 40% PEG 4000, 0.8 M sorbitol, and 50 mM $CaCl_2$ pH 4.5.

Casein plates was composed per liter of 7 g of $NaH_2PO_4.H_2O$, 0.5 g of KCl, 0.2 g of $MgSO_4.7H_2O$, 2 g of yeast extract, 10 g of glucose, 0.5 g of Triton X-100, 20 g of Noble agar, and 10 g of casein.

Starch azure plates were composed per liter of 0.1 g of glucose, 1 g of $KH_2PO_4$, 0.5 g of $MgSO_4$, 0.5 g of KCl, 3 g of $NaNO_3$, 0.1 g of yeast extract, 1 ml of Cove trace elements, 5 g of starch azure, 15 g of Noble agar, and 100 mM glycine pH 2.9.

Example 1

Transformation Procedure

Twenty micrograms of each of the disruption cassettes described in the following Examples were digested with a restriction enzyme and the fragment to be used for disruption was excised and purified from a 1% agarose-50 mM Tris base-50 mM borate-0.1 mM disodium EDTA buffer (TBE) gel using a QIAEX II Gel Extraction Kit (QIAGEN, Inc., Chatsworth, Calif.). The total volume was brought to 20 µl in sterile glass distilled water and split between four transformations.

Protoplasts were prepared using the following protocol. Shake flasks containing 20 ml of YP medium supplemented with 5% glucose were inoculated with *Aspergillus niger* conidia at a density of ca. $10^6$-$10^8$ per ml. Following an overnight (15-17 hours) incubation at 34° C. (200 rpm), the mycelia were collected by filtration with sterile Miracloth™ (Calbiochem, San Diego, Calif.) and transferred to a solution of 3-5 mg of Novozym™ 234 per ml in 10-20 ml of 1.2 M sorbitol (*Aspergillus niger* strains JRoy3, SMO110, and MBin111 through MBin114, see Examples 6-9) or 1 M $MgSO_4$ (*Aspergillus niger* strains MBin115 through MBin120, see Examples 9-12). Digestions with Novozym™ 234 were typically conducted for 30-45 minutes at 37° C. with gentle shaking at 80-100 rpm. The protoplasts were filtered through sterile Miracloth™, rinsed with 1.2 M sorbitol (*Aspergillus niger* strains MBin111 through MBin114) or 2 M sorbitol (*Aspergillus niger* strains MBin115 through MBin120), and centrifuged at 3000×g for 10 minutes. *Aspergillus niger* strains JRoy3, SMO110 and MBin111 through MBin114 were washed twice with 10 ml of 1.2 M sorbitol and once with 10 ml of 1.2 M sorbitol-50 mM $CaCl_2$, and then resuspended at a concentration of $3\times10^7$-$1\times10^8$ protoplasts per ml of 1.2 M sorbitol. *Aspergillus niger* strains MBin115 through MBin120 were washed once with 30 ml of 1 M sorbitol and once with 30 ml of STC, and then resuspended in STC:SPTC:DMSO (8:2:0.1 v/v) to achieve a concentration of $3\times10^7$-$1\times10^8$ protoplasts per ml. The *Aspergillus niger* protoplasts were either used directly for subsequent transformation or frozen at −80° C.

Prior to transformation of the protoplasts, selective overlay was melted and placed at 50° C. The overlay for pyrG selection was composed per liter of 20 ml of Cove salts, 273.8 g of sucrose, 8 g of Noble agar, 6 g of $NaNO_3$, and 1 g of NZAmine casamino acids, pH 5.5. The pyrG selection overlay was used for the creation of all gene disruptions. The overlay for amdS selection was composed per liter of 20 ml of Cove salts (50×), 273.8 g of sucrose, 8 g of Noble agar, 10 mM acetamide, and 15 mM CsCl. The amdS selection overlay was used when any expression plasmid was transformed.

DNA plus 5 µl of heparin (5 mg/ml of STC) was added to 100 µl of protoplasts and placed on ice for 30 minutes. *Aspergillus niger* strains prior to *Aspergillus niger* MBin115 in the lineage did not receive heparin. SPC was added (250 µl for *Aspergillus niger* strains JRoy3, SMO110 and MBin111 through MBin114 and 1 ml for the remaining strains) and mixed gently before incubation at room temperature for 30 minutes. A 10 ml volume of overlay (50° C.) was added and immediately poured onto a selective plate. The selection for gene disruptions using pyrG as the selectable marker was minimal medium supplemented with 1 M sucrose. In generating the *Aspergillus niger* MBin111 strain, minimal medium plates composed per liter of 1 M sucrose, 1 g of 5-fluoroorotic acid (5-FOA), and 10 mM uridine were used. Cove plates were used to select for transformants containing an expression plasmid. The plates were incubated at 34° C. for 3-7 days.

Example 2

Southern Analysis

*Aspergillus niger* mycelia were harvested from 15 mm plates containing 5 ml of YP medium supplemented with 5% glucose (and 10 mM uridine when applicable), filtered and rinsed with 10 mM Tris pH 7.4-0.1 mM EDTA pH 8 (TE) using a sidearm flask and porcelain filter, and finally placed in a microfuge tube to dry for 1 hour under a speed vacuum.

DNA was isolated using a Qiagen DNeasy Plant Mini Kit (QIAGEN, Inc., Chatsworth, Calif.). Five micrograms of the isolated DNA was digested for two hours (40 µl total volume, 4 U of specified restriction endonuclease/µl DNA) and electrophoresed on a 1% agarose gel using TBE buffer. The DNA was fragmented in the gel by treating with 0.25 M HCl, denatured with 1.5 M NaCl-0.5 M NaOH, and neutralized with 1.5 M NaCl-1 M Tris, pH 8, and then transferred in 20×SSC to a MSI MagnaGraph nylon transfer membrane (Micron Separations, Inc., Westborough, Mass.). The DNA was UV crosslinked to the membrane and prehybridized for 1 hour at 60° C. in 20 ml of DIG Easy Hyb (Roche Diagnostics Corporation, Indianapolis, Ind.).

Probes were prepared with the PCR DIG Probe Synthesis Kit as described by the manufacturer (Roche Diagnostics Corporation, Indianapolis, Ind.), electrophoresed, and excised from a 1% low melt agarose gel. Prior to use, the gel was melted and the probe denatured by boiling for 10 minutes. Ten percent of the total gel volume was added to the hybridization buffer. The denatured probe was added directly to the DIG Easy Hyb buffer and an overnight hybridization at 60° C. was performed. Following post hybridization washes (twice in 2×SSC, once in 0.4×SSC, 60° C., 10 minutes each), chemiluminescent detection using the DIG detection system and CPD-Star (Roche Diagnostics Corporation, Indianapolis, Ind.) was performed. The DIG-labeled DNA Molecular Weight Marker III (Roche Diagnostics Corporation, Indianapolis, Ind.) was used as a standard.

Example 3

Construction of *Aspergillus niger* Genomic Lambda Library

*Aspergillus niger* Bo-1 DNA was isolated by lysis in guanidine hydrochloride according to the procedure of Wahleithner et al., 1996, *Current Genetics*. 29: 395-403, followed by purification on a Qiagen Maxiprep column (QIAGEN, Inc., Chatsworth, Calif.) as described by manufacturer. A genomic library of *Aspergillus niger* Bo-1 was created in EMBL4 (Clonetech, Palo Alto, Calif.) according to the manufacturer's instructions. *Aspergillus niger* Bo-1 genomic DNA was partially digested with Sau3A. After digestion, the DNA was electrophoresed on a preparative low-melting-point agarose gel, and the region containing 8 to 23-kb DNA was sliced from the gel. The DNA was extracted from the gel with beta-agarase (New England Biolabs, Waltham, Mass.). The isolated DNA was ligated with EMBL4 arms (Clonetech, Palo Alto, Calif.) as described in the supplier's directions. The ligation was packaged in vitro with a Gigapack Gold II Packaging Kit (Stratagene, La Jolla, Calif.). The titer of the library was determined, and the library was amplified with *E. coli* K802 cells (American Type Culture Collection, Rockville, Md.). The unamplified library was estimated to contain 26,500 independent recombinants.

Example 4

Construction of pyrG Cassette

Approximately 26,500 plaques from the genomic library of *Aspergillus niger* Bo-1 contained in EMBL4 were replica plated onto nylon filters and probed with a 1.4 kb fragment from the pyrG gene of *Aspergillus nidulans*. Several positive clones were purified and propagated as described by the manufacturer. Phage DNA from the positive clones was isolated using a Qiagen lambda Mini Prep Kit (QIAGEN, Inc., Chatsworth, Calif.). Phage DNA was digested with several restriction enzymes followed by Southern analysis to identify fragments containing the pyrG gene. One clone designated clone 7b contained the *Aspergillus niger* pyrG gene (SEQ ID NOs: 1 [DNA sequence] and 2 [deduced amino acid sequence]), including both the promoter and terminator sequences, on a 3.5 kb XbaI fragment.

The pyrG gene fragment was subcloned from clone 7b into pUC118 (Roche Diagnostics Corporation, Mannheim, Germany) as a 3.5 kb XbaI fragment resulting in pJRoy10 (FIG. 1). The pyrG gene, including both the promoter and terminator sequences, was isolated from pJRoy10 by digestion with KspI and SpeI. The fragment, containing a KspI site at the 5' end and a SpeI site at the 3' end, was isolated using a QIAEX II Gel Extraction Kit following electrophoresis on a 1% agarose-TBE gel and purified.

A 582 bp fragment of the pyrG terminator sequence was PCR amplified from pJRoy10, such that SpeI and KspI sites were added to the 5' and 3' ends of the fragment, respectively. Primer 1 was used to create the SpeI site and primer 2 added the KspI site.

```
Primer 1:
5'-GGGACTAGTGGATCGAAGTTCTGATGGTTA-3' (SEQ ID NO: 3)

Primer 2:
5'-ATACCGCGGGTTTCAAGGATGGAGATAGGA-3' (SEQ ID NO: 4)
```

PCR amplification was conducted in 50 µl reactions composed of 10 ng of pJRoy10 plasmid DNA, 50 pmol of each primer, 2.5 mM each of dATP, dCTP, dGTP, and dTTP, 1×PCR Buffer (Applied Biosystems, Inc., Foster City, Calif.) with 2.5 mM $MgCl_2$, and 2.5 units of Taq DNA polymerase (Roche Diagnostics Corporation, Indianapolis, Ind.). The reactions were performed in a RoboCycler 40 thermacycler (Stratagene, La Jolla, Calif.) programmed for 1 cycle at 95° C. for 3 minutes; 30 cycles each at 95° C. for 1 minute, 60° C. for 1 minute, and 72° C. for 1.5 minutes; and 1 cycle at 72° C. for 5 minutes.

The 582 bp PCR product was digested with SpeI and KspI and used directly as described below.

Figure 2:
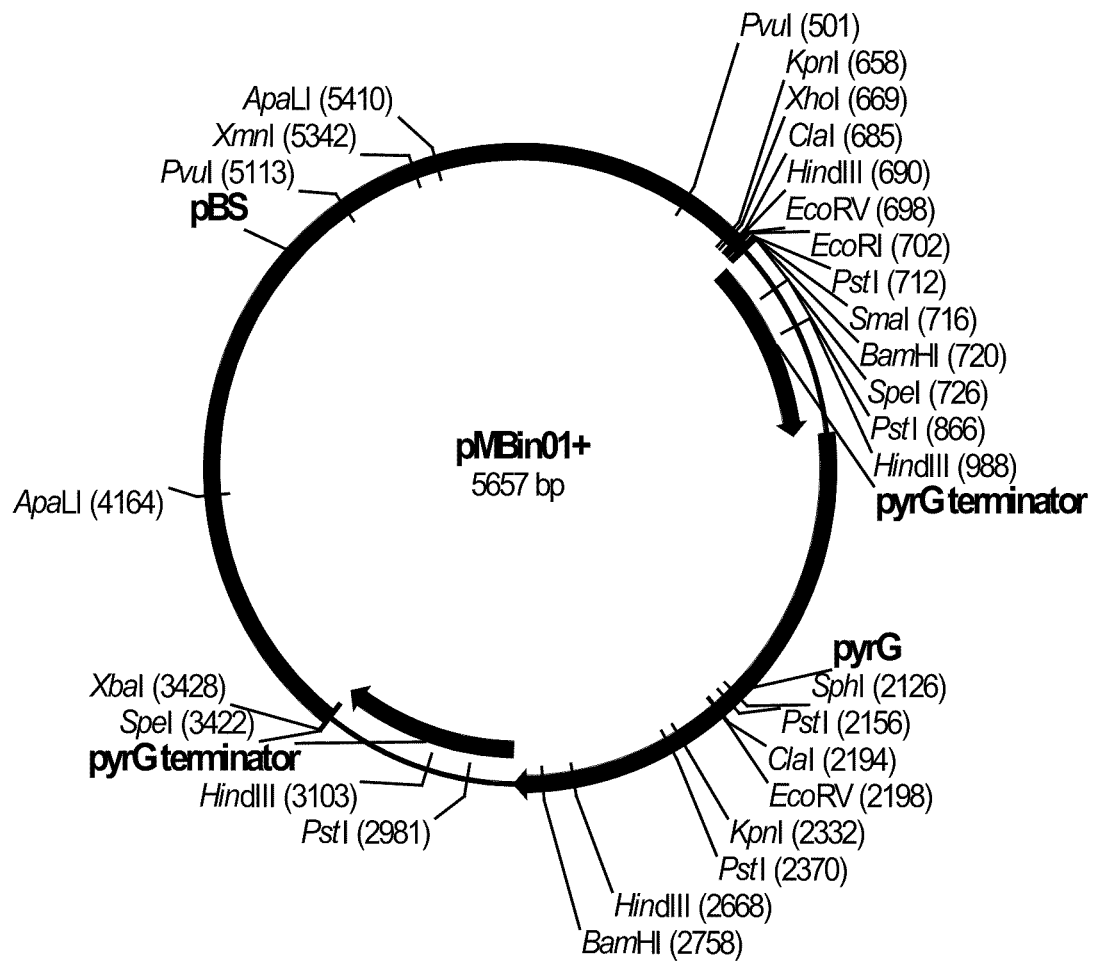
FIG. 2 shows a restriction map of pMBin01+.

Plasmid pMBin01+ (FIG. 2) was constructed by ligating the *Aspergillus niger* pyrG gene fragment and the *Aspergillus niger* pyrG terminator fragment into the SpeI site of pBluescript SK– (Stratagene, La Jolla, Calif.), such that pyrG was flanked by 582 bp of terminator sequence on both sides. A 2696 bp SpeI fragment was isolated from pMBin01+ and purified using a QIAEX II Gel Extraction Kit following electrophoresis on a 1% agarose-TBE gel. Plasmid DNA was isolated using Qiagen QiaPrep8 Miniprep or Maxiprep Kits (QIAGEN, Inc., Chatsworth, Calif.). The 2696 bp SpeI fragment was then used to construct all disruption cassettes.

Example 5

Creation of Uridine Auxotrophs

Gene disruptions described in the following Examples utilized the *Aspergillus niger* pyrG gene as a selectable marker. The pyrG gene encodes orotodine-5'-phosphate decarboxylase which enables an uridine auxotroph to grow without the addition of uridine. The repetitive use of pyrG was made possible by the addition of repeat sequence to the ends of the marker as described in Example 4. Excision of pyrG occurred by homologous recombination between the direct repeats upon selection on 5-FOA (d'Enfert, 1996, *Current Genetics* 30: 76-82).

As described in Example 4, the disruption cassettes contained the pyrG gene flanked by 582 bp of repetitive pyrG terminator sequence. Following gene disruption, each strain was passaged once on minimal medium containing 10 mM uridine in order to remove selection for the pyrG gene. Spores were collected from plates containing 10 mM uridine and transferred to minimal medium plates containing 10 mM uridine and 1 g of 5-FOA per liter. *Aspergillus niger* cells in which the pyrG gene was lost grow in the presence of 5-FOA while those that retain the gene convert 5-FOA to 5-fluoro-UMP, a toxic intermediate. Colonies that grew more quickly and sporulated were picked out of the lawn of slower growing non-sporulating colonies and isolated by passaging twice on minimal medium plates containing 10 mM uridine and 1 g of 5-FOA per liter and selecting for single, sporulating colonies. Southern analysis was performed as described in Example 2 to ensure that the pyrG gene had been excised. One copy of the pyrG terminator was left at the site of disruption.

Example 6

Construction of *Aspergillus niger* SMO110 (Δgla)

Figure 3:
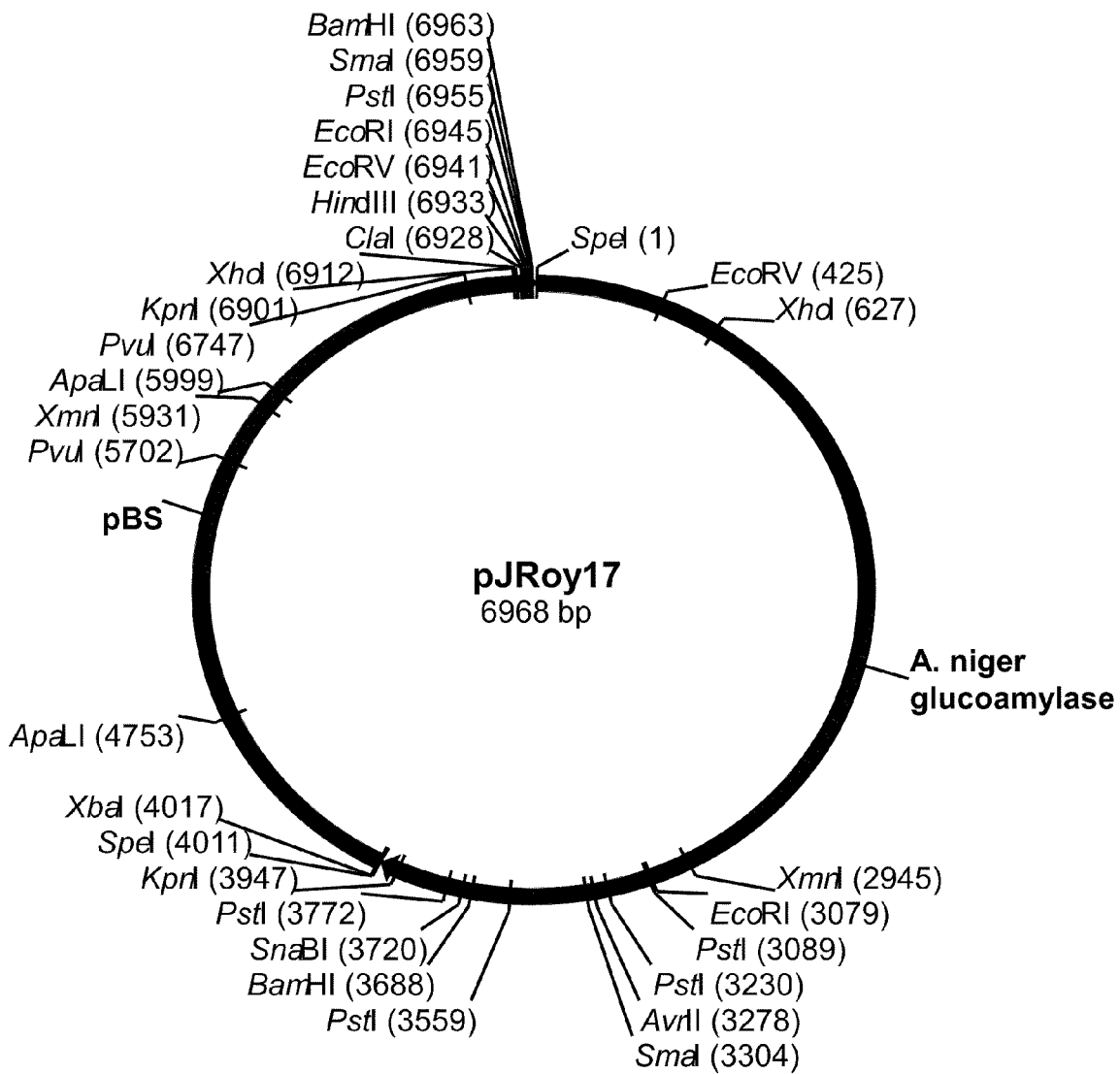
FIG. 3 shows a restriction map of pJRoy17.

The *Aspergillus niger* glucoamylase (gla) gene (SEQ ID NOs: 5 [DNA sequence] and 6 [deduced amino acid sequence]) was isolated from the genomic lambda library described in Example 3 as an 8 kb fragment and subcloned into pUC118 (Roche Diagnostics Corporation, Mannheim, Germany) to generate pJRoy13. A 4 kb SpeI fragment from pJRoy13 containing the *Aspergillus niger* glucoamylase gene and 1.8 kb of flanking DNA was inserted into pBluescriptSK+ (Stratagene, La Jolla, Calif.) to generate pJRoy17 (FIG. 3)

Figure 4:
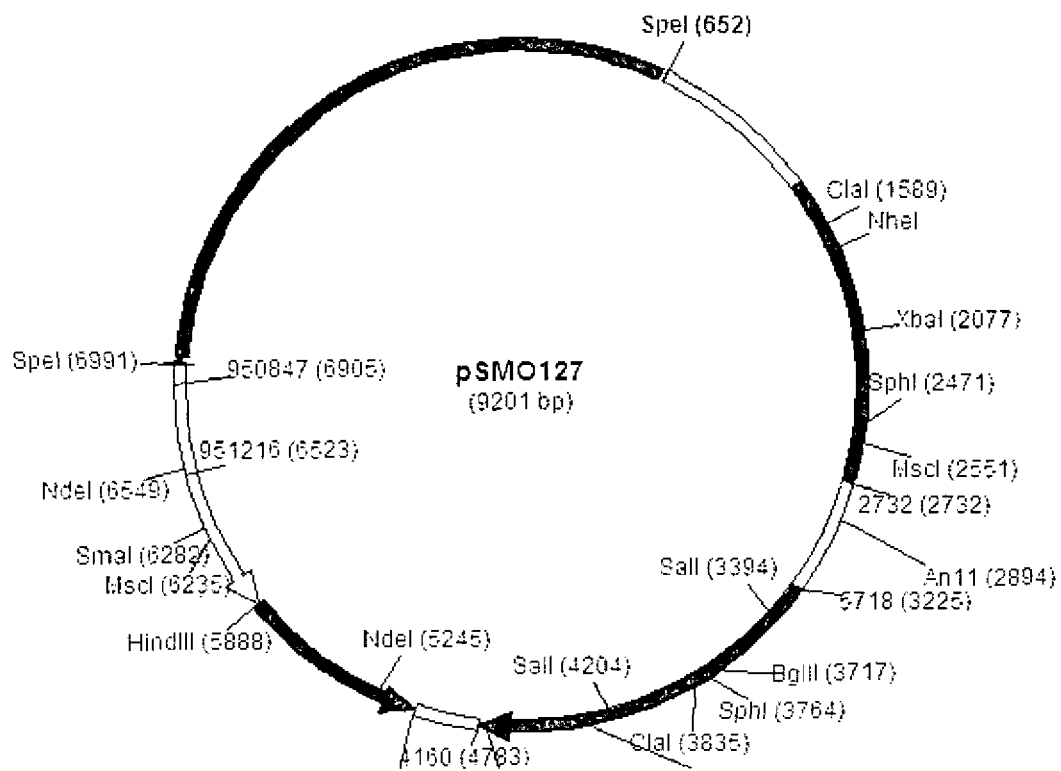
FIG. 4 shows a restriction map of pSMO127.

A 2.3 kb SpeI/XhoI fragment containing the pyrG gene was isolated from pJRoy10 using a QIAEX II Gel Extraction Kit following electrophoresis on a 1% agarose-TBE gel. The restricted ends were filled in with Klenow (Roche Diagnostics Corporation, Indianapolis, Ind.) and the fragment was inserted into the BglII site within the glucoamylase gene coding region of pJRoy17 to create plasmid pSMO127 (FIG. 4). Between two SpeI sites of pSMO127 was 2.3 kb of pyrG gene flanked by 2.2 kb and 2.3 kb of 5' and 3' glucoamylase gene sequence, respectively.

Plasmid pSMO127 was digested with SpeI and a 6 kb fragment consisting of the linear disruption cassette was isolated and used to transform a pyrG deleted strain, *Aspergillus niger* JRoy3, using the transformation procedure described in Example 1. *Aspergillus niger* JRoy3 was obtained from

*Aspergillus niger* Bo-1 using the procedure described in Example 5. Approximately 700 transformants were obtained.

A 1100 bp fragment containing the glucoamylase gene promoter was PCR amplified from the *Aspergillus niger* glucoamylase gene locus (1113 bp directly preceding the start codon) and used as a probe in Southern blot analysis. The probe was generated with primers 3 and 4 where primer 3 hybridized to a SpeI site at the 5' end and primer 4 added a SphI site to the 3' end.

```
Primer 3:
5'-ACTAGTGGCCCTGTACCCAGA-3'        (SEQ ID NO: 7)

Primer 4:
5'-GCATGCATTGCTGAGGTGTAATGATG-3'   (SEQ ID NO: 8)
```

PCR amplification of the glucoamylase gene promoter was conducted in 50 µl reactions composed of 10 ng of pJRoy17 plasmid DNA, 50 pmol of each primer, 2.5 mM each of dATP, dCTP, dGTP, and dTTP, 1×PCR Buffer with 2.5 mM $MgCl_2$, and 2.5 units of Taq DNA polymerase. The reactions were performed in a RoboCycler 40 thermacycler programmed for 1 cycle at 95° C. for 3 minutes; 30 cycles each at 95° C. for 1 minute, 55° C. for 1 minute, and 72° C. for 2 minutes; and 1 cycle at 72° C. for 5 minutes.

The glucoamylase gene promoter probe was isolated and labeled as described in Example 2.

Genomic DNA was prepared from 200 of the 700 transformants as described in Example 2. The genomic DNA was digested with SpeI and then submitted to Southern analysis with the above probe using the protocol described in Example 2. A gene replacement of the disruption cassette into the glucoamylase gene locus resulted in an increase of the wild type 4 kb glucoamylase gene band to 6.3 kb, an increase due to the 2.3 kb pyrG gene. One such transformant was identified and designated *Aspergillus niger* SMO110.

Example 7

Construction of *Aspergillus niger* MBin111 (ΔpyrG, Δgla)

The *Aspergillus niger* glucoamylase gene terminator was amplified from pJRoy17 as a 800 bp fragment with primer 5 which hybridized to the SpeI site at the 3' end and primer 6 that added a SphI site to the 5' end.

```
Primer 5:
                                    (SEQ ID NO: 9)
5'-GAGGTCGACGGTATCGATAAG-3'

Primer 6:
                                    (SEQ ID NO: 10)
5'-GCATGCAGATCTCGAGAATACACCGTTCCTCAG-3'
```

PCR amplification of the gla gene terminator was conducted in 50 µl reactions composed of 10 ng of pJRoy17 plasmid DNA, 50 pmol of each primer, 2.5 mM each of dATP, dCTP, dGTP, and dTTP, 1×PCR Buffer with 2.5 mM $MgCl_2$, and 2.5 units of Taq DNA polymerase. The reactions were performed in a RoboCycler 40 thermacycler programmed for 1 cycle at 95° C. for 3 minutes; 30 cycles each at 95° C. for 1 minute, 55° C. for 1 minute, and 72° C. for 2 minutes; and 1 cycle at 72° C. for 5 minutes.

The 800 bp fragment containing the glucoamylase gene terminator was purified and used directly as described below.

Figure 5:
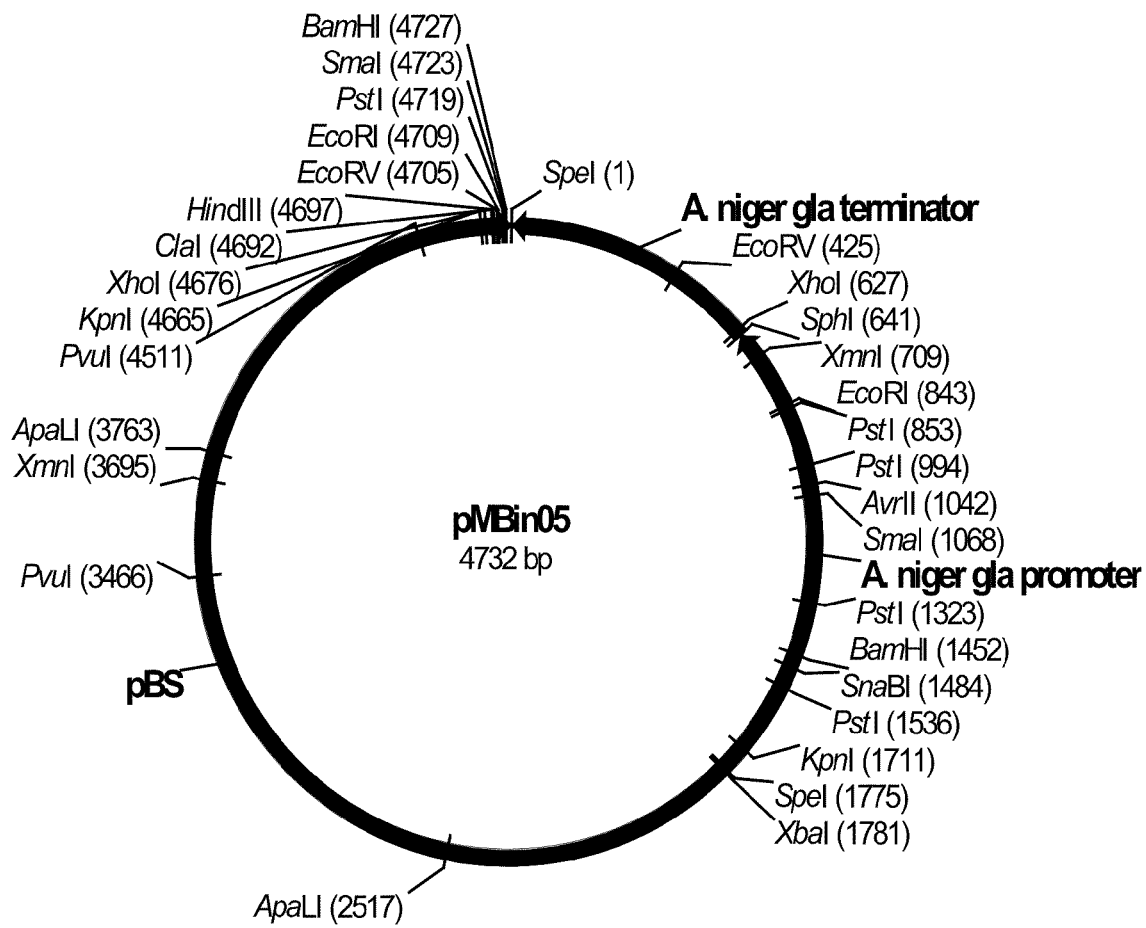
FIG. 5 shows a restriction map of pMBin05.

The glucoamylase gene promoter (Example 7) and terminator PCR products were subcloned into a pCR2.1 vector using a TOPO-TA Cloning Kit (Invitrogen, Carlsbad, Calif.) according to the manufacturer's instructions. A 1.1 kb SpeI/SphI fragment containing the glucoamylase gene promoter was isolated using a QIAEX II Gel Extraction Kit following electrophoresis on a 1% agarose-TBE gel. The glucoamylase gene terminator was isolated in the same manner, however, digestion with SpeI/SphI resulted in a 554 bp fragment due to an internal SphI site. The promoter and terminator were ligated into the SpeI site of pBluescript SK-(Stratagene, La Jolla, Calif.) resulting in pMBin05 (FIG. 5).

A SpeI fragment was removed from pMBin05 by restriction enzyme digestion and isolated using a QIAEX II Gel Extraction Kit following electrophoresis on a 1% agarose-TBE gel. The isolated fragment was transformed into *Aspergillus niger* SMO110 (Example 6) to delete the pyrG disrupted glucoamylase locus using the transformation procedure described in Example 1. Prior to plating the transformation on 5-FOA to select for the pyrG minus phenotype (see Example 5), an outgrowth was performed to allow more time for recombination prior to selection. The outgrowth was conducted in 5 ml of YP medium supplemented with 5% glucose, 0.9 M sucrose, and 10 mM uridine for 24 hours at 37° C. and 100 rpm.

Nine transformants were obtained and one maintained the pyrG-phenotype when transferred to selective media described in Example 5. The transformant maintaining the pyrG-phenotype was designated *Aspergillus niger* MBin111.

Probes were generated to the *Aspergillus niger* glucoamylase and pyrG genes. Primers 3 and 5 above were used to PCR amplify the gla gene (including promoter and terminator) from pJRoy17 and primers 1 and 2 (see Example 4) were used to amplify the pyrG terminator sequence from pJRoy10 using the same procedure described in Example 4. The probes were isolated and labeled as described in Example 2.

Genomic DNA was isolated from *Aspergillus niger* strains JRoy3, SMO110, and MBin111 as described in Example 2, digested with SpeI, and probed with the *Aspergillus niger* glucoamylase gene according to the protocol described in Example 2 for Southern analysis. A 4 kb band representing the undisrupted gla gene locus was observed in *Aspergillus niger* JRoy3 and a 6.3 kb band, due to the insertion of the disruption cassette, was obtained from *Aspergillus niger* SMO110. No hybridization was detected with genomic DNA from *Aspergillus niger* MBin111, indicating that the glucoamylase gene had been deleted. Moreover, DNA digested with SpeI was probed with the pyrG terminator sequence and again no hybridization was observed in the *Aspergillus niger* MBin111 strain, but *Aspergillus niger* SMO110 maintained the 6.3 kb band. These results indicated that the entire glucoamylase gene locus and pyrG gene were deleted in *Aspergillus niger* MBin111.

Example 8

Construction of *Aspergillus niger* MBin112 (Δasa, ΔpyrG, Δgla)

Figure 6:
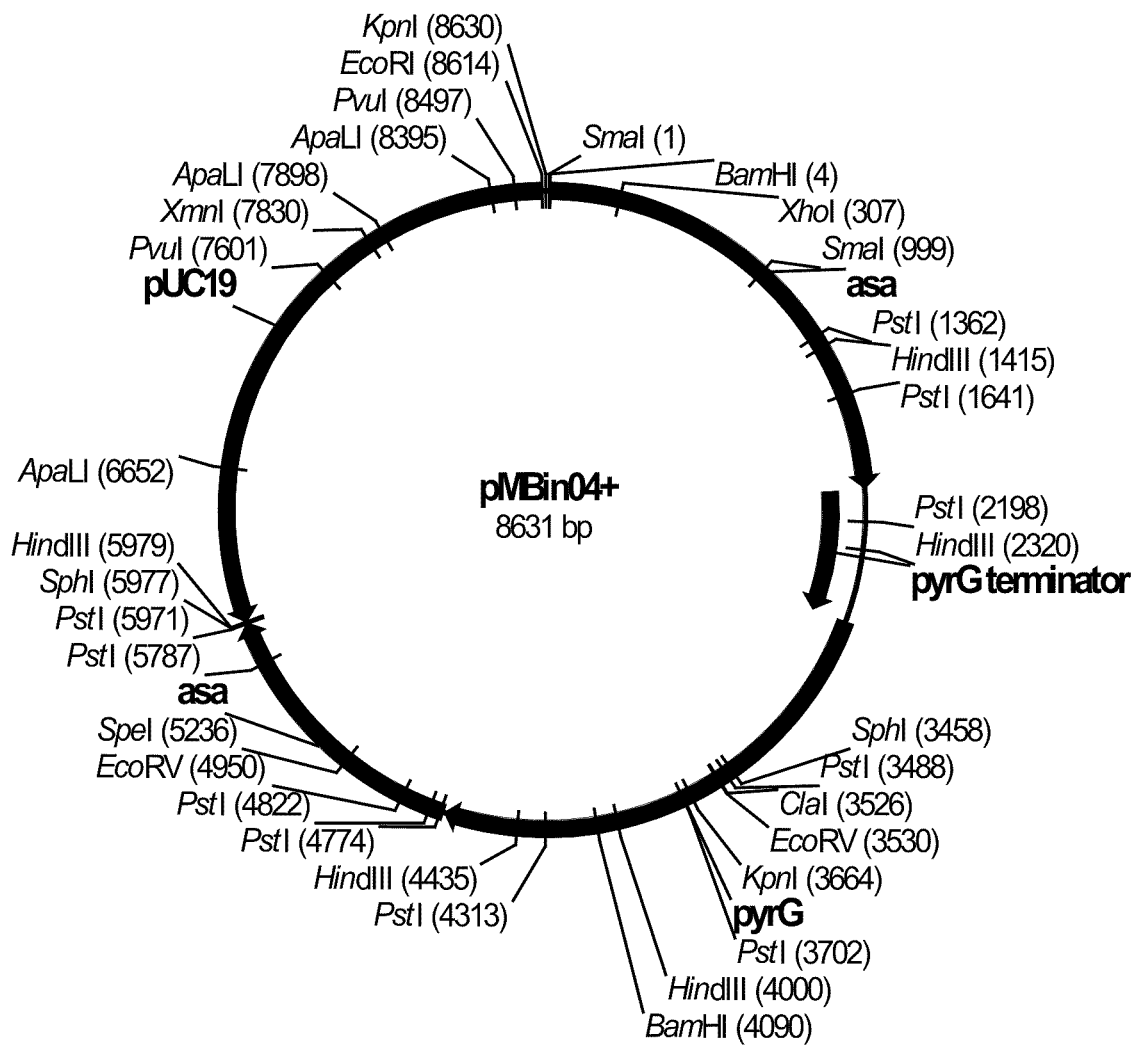
FIG. 6 shows a restriction map of pMBin04+.

A portion of the *Aspergillus niger* acid stable alpha-amylase gene (asa) was isolated and cloned into pUC19 (Roche Diagnostics Corporation, Mannheim, Germany) as described in U.S. Pat. No. 5,252,726. A 101 bp fragment, 346 bp upstream of the start codon of the portion of the acid stable alpha-amylase gene, was excised from pUC19 containing the portion of the acid stable alpha-amylase gene by digestion with HpaI and the SpeI fragment from pMBin01 (Example 4) was inserted into this site by blunt end ligation to create pMBin04+ (FIG. 6). A double digest of pMBin04+ was performed with SmaI and SpeI and a 4237 bp SmaI/SpeI fragment was isolated using a QIAEX II Gel Extraction Kit following electrophoresis on a 1% agarose-TBE gel. The 4237 bp SmaI/SpeI fragment consisted of the 5' end of acid stable alpha-amylase gene, the pyrG terminator, the entire pyrG gene (including the terminator), and the 3' end of the acid stable alpha-amylase gene.

*Aspergillus niger* strain MBin111 was transformed with the SmaI/SpeI fragment from pMBin04+ using the transformation procedure described in Example 1. Totally, 160 transformants were obtained on minimal medium. The transformants were then transferred to starch azure plates to screen for those lacking acid stable alpha-amylase activity. Sixteen transformants produced little or no clearing zones and were single colony isolated twice on minimal medium supplemented with 10 mM uridine.

A 522 bp fragment was PCR amplified from the acid stable alpha-amylase gene locus and used as a probe in Southern blot analysis. The probe was generated with primers 7 and 8.

```
Primer 7:
5'-CTCATTGGCCGAAACTCCGAT-3'    (SEQ ID NO: 11)

Primer 8:
5'-AGCAGACGATGTCCTGAGCTG-3'    (SEQ ID NO: 12)
```

PCR amplification of the 522 bp fragment was conducted in 50 µl reactions composed of 10 ng of pUC19/HW360 plasmid DNA, 50 pmol of each primer, 2.5 mM each of dATP, dCTP, dGTP, and dTTP, 1×PCR Buffer with 2.5 mM $MgCl_2$, and 2.5 units of Taq DNA polymerase. The reactions were performed in a RoboCycler 40 thermacycler programmed for 1 cycle at 95° C. for 3 minutes; 30 cycles each at 95° C. for 1 minute, 55° C. for 1 minute, and 72° C. for 1 minute; and 1 cycle at 72° C. for 5 minutes.

The 522 bp probe was isolated and labeled as described in Example 2.

Genomic DNA was isolated as described in Example 2 from the 16 transformants and untransformed *Aspergillus niger* strain MBin111 as a control. The genomic DNA was then digested with XhoI and SpeI and submitted to Southern hybridization as described in Example 2 using the probe above. The intact acid stable alpha-amylase gene locus was visualized as a 2.3 kb band and the disrupted locus was 5.3 kb in size. This size difference is due to the insertion of the 3 kb pMBin01+SpeI fragment described in Example 4. Five transformants containing an acid stable alpha-amylase gene disruption were obtained and one was designated *Aspergillus niger* MBin112. The loop-out of the disruption cassette, resulting in *Aspergillus niger* strain MBin113, left behind the pyrG terminator and created a 2.8 kb band. The loop-out was performed as described in Example 5 and resulted in *Aspergillus niger* MBin113.

Example 9

Construction of *Aspergillus niger* MBin114 (ΔprtT, Δasa, ΔpyrG, Δgla)

Figure 7:
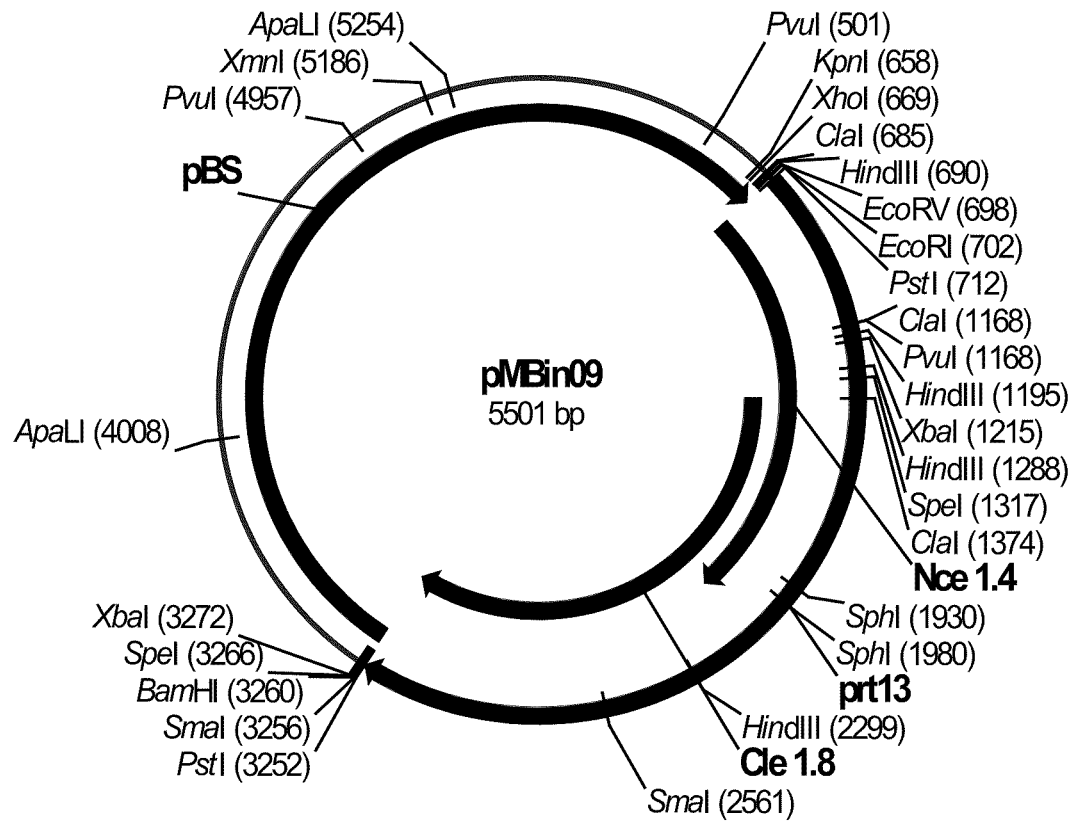
FIG. 7 shows a restriction map of pMBin09.

The *Aspergillus niger* prtT gene (SEQ ID NOs: 13 [DNA sequence] and 14 [deduced amino acid sequence]) was constructed (pMBin09, FIG. 7) using two overlapping clones, NcE 1.4 and CIE 1.8, described in WO 00/20596. NcE 1.4, CIE 1.8, and pZeRO-2 (Invitrogen, Carlsbad, Calif.) were digested with PstI, generating PstI sites at the 5' and 3' ends of the clones respectively and linearizing pZeRO-2 at the multiple cloning site. Utilizing a SspI site in a shared region of both prtT clones, a three way ligation was performed by ligating the PstI/SspI clone fragments into pZeRO-2 at the PstI site, resulting in pMBin09.

Figure 8:
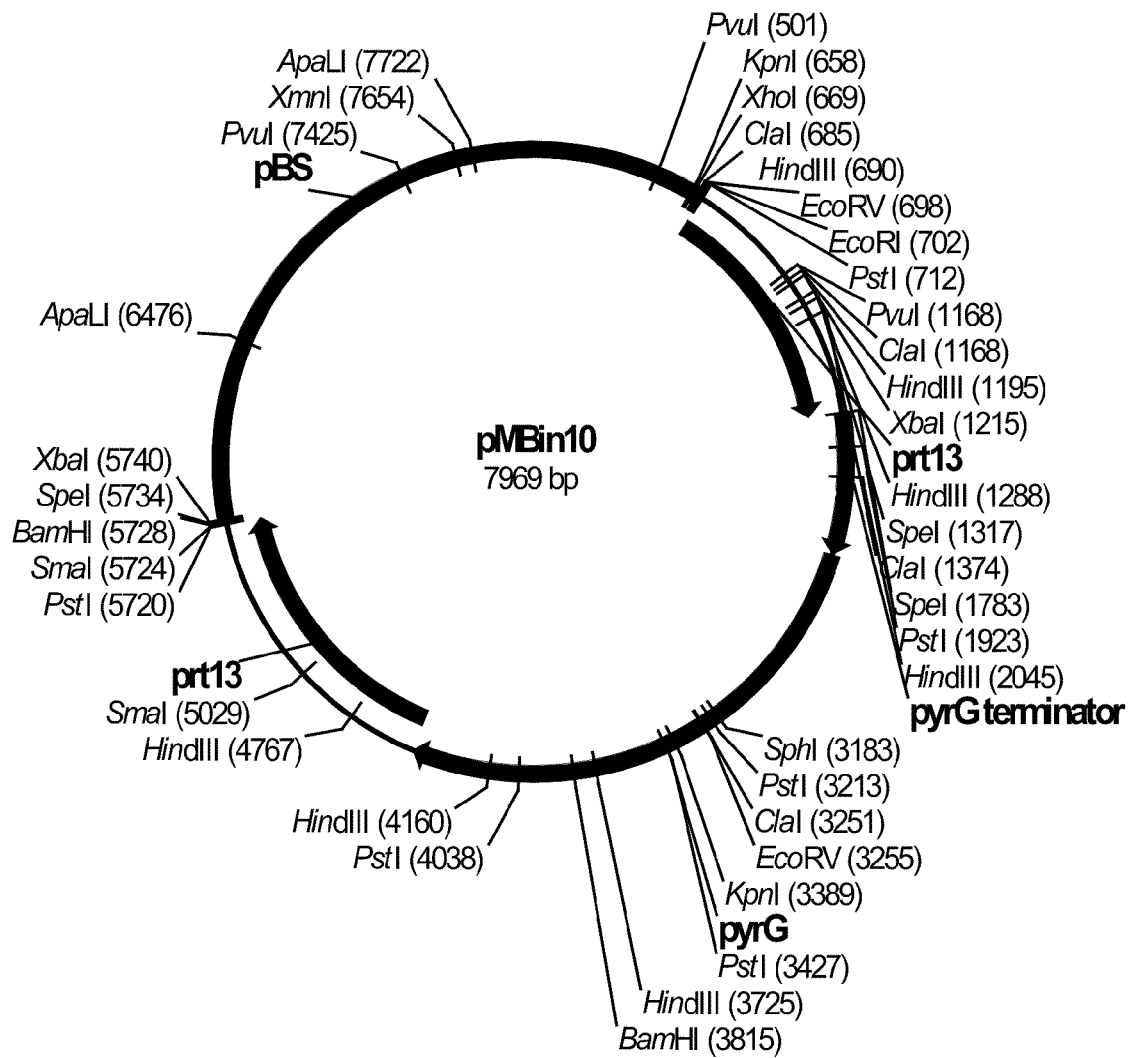
FIG. 8 shows a restriction map of pMBin10.

A 233 bp deletion of the prtT coding sequence was first made by digestion of pMBin09 with Bst1107I/SspI and the pMBin01 SpeI fragment described in Example 4 was inserted as a blunt fragment into the digested pMBin09 to create pMBin10 (FIG. 8). The prtT disruption was performed using the DraIII/NheI fragment from pMBin10 which was isolated using a QIAEX II Gel Extraction Kit following electrophoresis on a 1% agarose-TBE gel.

*Aspergillus niger* MBin113 was transformed with the DraIII/NheI fragment from pMBin10 using the transformation procedure described in Example 1. One hundred and two transformants were screened on casein plates. Nine transformants showed little or no clearing and were single colony isolated twice on minimal medium supplemented with 10 mM uridine.

A 232 bp fragment of the prtT coding sequence was PCR amplified from the prtT locus in pMBin10 and used as a probe in Southern blot analysis. The fragment was generated using primers 9 and 10.

```
Primer 9:
5'-TGTGATTGAGGTGATTGGCG-3'    (SEQ ID NO: 15)

Primer 10:
5'-TCAGCCACACCTGCAAAGGC-3'    (SEQ ID NO: 16)
```

PCR amplification was conducted in 50 µl reactions composed of 10 ng of pMBin10 plasmid DNA, 50 pmol of each primer, 2.5 mM each of dATP, dCTP, dGTP, and dTTP, 1×PCR Buffer with 2.5 mM $MgCl_2$, and 2.5 units of Taq DNA polymerase. The reactions were performed in a RoboCycler 40 thermacycler programmed for 1 cycle at 95° C. for 3 minutes; 30 cycles each at 95° C. for 1 minute, 60° C. for 1 minute, and 72° C. for 1 minute; and 1 cycle at 72° C. for 5 minutes.

The probe was isolated and labeled as described in Example 2 and contained 232 bp of the prtT coding sequence downstream of the disruption.

Genomic DNA was isolated as described in Example 2 from the 9 transformants, as well as *Aspergillus niger* Bo-1 and *Aspergillus niger* MBin112 as controls, and submitted to Southern analysis as described in Example 2. The genomic DNA was digested with PstI and a 2.5 kb band, corresponding to the undisrupted prtT gene, was observed in the control strains. A band at 1.3 kb, corresponding to a prtT gene disruption, was observed when the probe hybridized to a PstI fragment containing 132 bp of the pyrG terminator and 1198 bp of the prtT gene. One disruptant was chosen and designated *Aspergillus niger* MBin114. The pyrG gene was looped out as described in Example 5 resulting in *Aspergillus niger* MBin115.

Example 10

Construction of *Aspergillus niger* MBin116 (ΔamyB, ΔprtT, Δasa, ΔpyrG, Δgla)

The *Aspergillus niger* neutral alpha-amylase genes, amyA and amyB, were cloned as disclosed in U.S. Pat. No. 5,252,726 (NA1=amyA and NA2=amyB).

Figure 9:
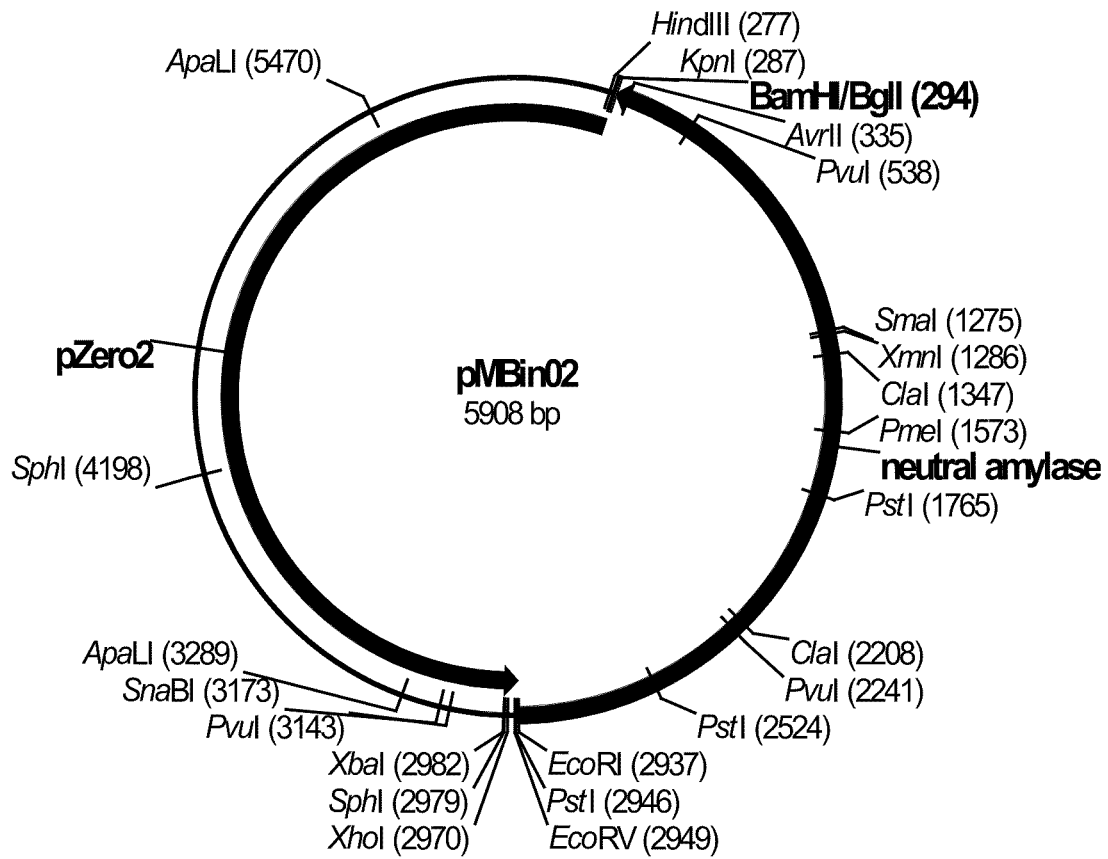
FIG. 9 shows a restriction map of pMBin02.
Figure 10:
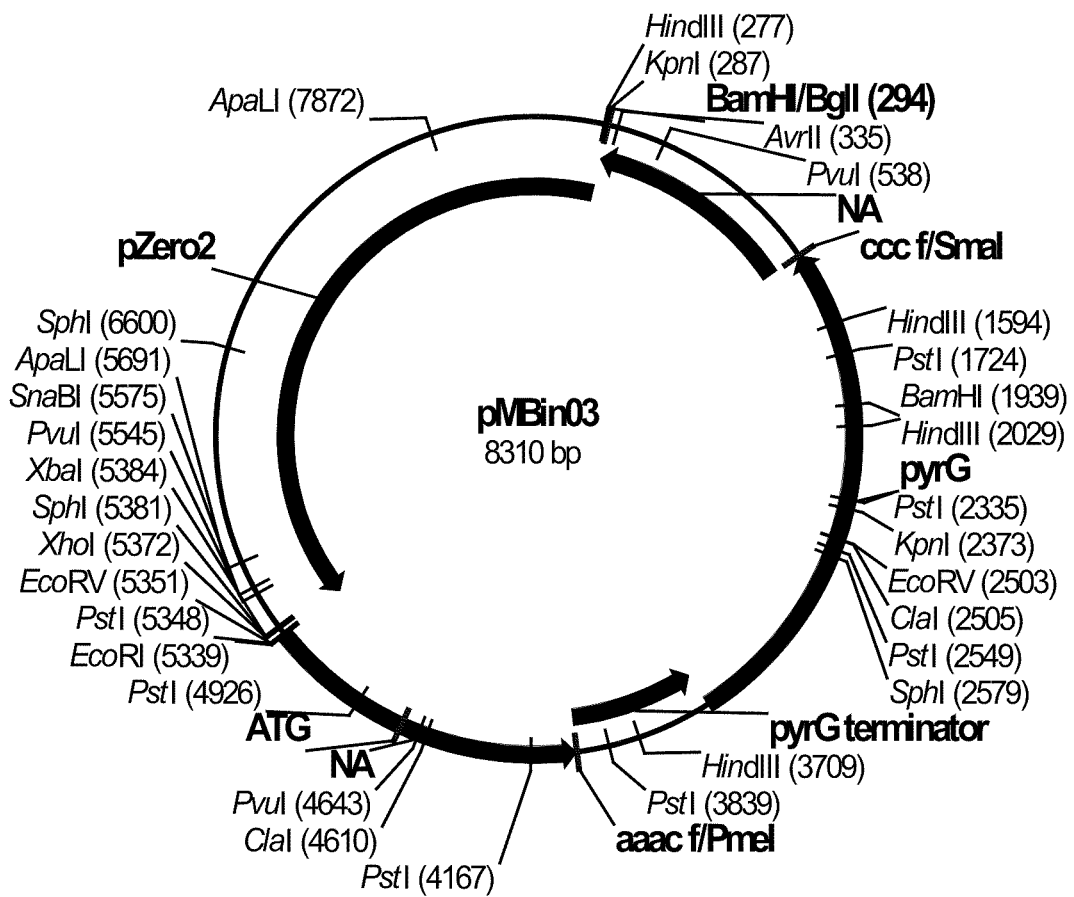
FIG. 10 shows a restriction map of pMBin03.

A 2.6 kb fragment of the *Aspergillus niger* neutral alpha-amylase gene (amyB) (SEQ ID NOs: 17 [DNA sequence] and 18 [deduced amino acid sequence]) was isolated from pTaka17 (U.S. Pat. No. 5,536,661) by EcoRI/BglII digestion and isolated using a QIAEX II Gel Extraction Kit following electrophoresis on a 1% agarose-TBE gel. The 2.6 kb fragment was inserted into the EcoRI/BamHI site of pZero2.0 (Invitrogen, Carlsbad, Calif.) to create pMBin02 (FIG. 9). A 298 bp deletion that removed 186 bp from the fifth exon and 52 bp from the sixth exon of the homologous amyB gene was made in pMBin02 by PmeI/SmaI digestion and the pMBin01 2696 bp SpeI fragment (described in Example 4) was inserted by blunt end ligation to create pMBin03 (FIG. 10).

*Aspergillus niger* MBin115 was transformed using the protocol described in Example 1 with an EcoRI/AvdII fragment isolated from pMBin03. One hundred and ninety two transformants were obtained and transferred to starch azure plates as described in Example 8 with the following changes: the starch azure plates lacked glycine and the pH was at 5. Eight transformants showed reduced clearing zones and were single colony isolated twice on minimal medium supplemented with 10 mM uridine.

A probe with a sequence corresponding to 295 bp of the *Aspergillus niger* amyA or amyB coding sequence, 450 bp downstream of the ATG site (the amyA and amyB sequences are identical in this region), was generated by PCR amplification using primers 11 and 12.

```
Primer 11:
5'-GGCAGCAGGATATGTAAGTCG-3'    (SEQ ID NO: 19)

Primer 12:
5'-CACTGTAATCGACTGAGCTAC-3'    (SEQ ID NO: 20)
```

PCR amplification was conducted in 50 µl reactions composed of 10 ng of pMBin03 plasmid DNA, 50 pmol of each primer, 2.5 mM each of dATP, dCTP, dGTP, and dTTP, 1×PCR Buffer with 2.5 mM MgCl$_2$, and 2.5 units of Taq DNA polymerase. The reactions were performed in a RoboCycler 40 thermacycler programmed for 1 cycle at 95° C. for 3 minutes; 30 cycles each at 95° C. for 1 minute, 60° C. for 1 minute, and 72° C. for 1 minute; and 1 cycle at 72° C. for 5 minutes.

The probe was isolated and labeled as described in Example 2. Genomic DNA was isolated as described in Example 2 from the 8 transformants and untransformed *Aspergillus niger* MBin115 as a control and digested with EcoRI and BspLU11I. The digested genomic DNA was submitted to Southern analysis using the procedure described in Example 2. There was an EcoRI site 616 bp upstream of the start codon and a BspLu11I site 99 bp downstream of the stop codon. The wildtype *Aspergillus niger* strain Bo-1 amyB gene band was 2659 bp. Disruption of the amyB gene resulted in the disappearance of the 2659 bp band and the appearance of a band at 5359 bp due to the insertion of the pMBin01 SpeI fragment.

One transformant contained a clean disruption and was designated *Aspergillus niger* MBin116. The pyrG gene was excised from *Aspergillus niger* MBin116 as described in Example 5 and the strain was designated *Aspergillus niger* MBin117.

Example 11

Construction of *Aspergillus niger* MBin118 (ΔamyA, ΔamyB, ΔprtT, Δasa, ΔpyrG, Δgla)

Since the *Aspergillus niger* amyA gene sequence is essentially identical to amyB, except at the 3' end (Korman et al., 1990, *Current Genetics* 17: 203-212), the disruption construct and protocol used in Example 10 was applied. *Aspergillus niger* MBin117 was transformed according the protocol described in Example 1 with the EcoRI/AvrII fragment from pMBin03 in order to disrupt the amyA gene (SEQ ID NOs: 21 [DNA sequence] and 22 [deduced amino acid sequence]).

Three hundred and fifty six transformants were obtained and transferred to starch azure plates as described in Example 10. Four transformants producing no clearing zones on the starch azure plates were single colony isolated twice on minimal medium supplemented with 10 mM uridine.

Genomic DNA was isolated from the 4 transformants and *Aspergillus niger* MBin117 as a control and submitted to Southern analysis using the procedures described in Example 2. The genomic DNA was digested with EcoRI and BspLU11I and probed as described in Example 10. A 2.7 kb band corresponding to the amyB gene and a slightly larger band representing the amyA gene were present in the wild type *Aspergillus niger* Bo-1 strain. The exact size of the amyA band was not known since BspLU11I cuts at an unknown site downstream of the amyA gene. In one of the transformants analyzed, a band corresponding to the amyA gene was no longer visible with the probe indicating that a deletion of the amyA gene encompassing the location of the probe had occurred. The transformant was designated *Aspergillus niger* MBin118. The pyrG gene was excised from *Aspergillus niger* MBin118 as described in Example 5 and the strain was designated *Aspergillus niger* MBin119.

Example 12

Construction of *Aspergillus niger* MBin120 (Δoxa, ΔamyA, ΔamyB, ΔprtT, Δasa, ΔpyrG, Δgla)

An *Aspergillus niger* oxalic acid hydrolase (oah) gene (SEQ ID NOs: 23 [DNA sequence] and 24 [deduced amino acid sequence]) was cloned according to the procedure described in WO 00/50576. Plasmid pHP1 was constructed as described in WO 00/50576.

Figure 11:
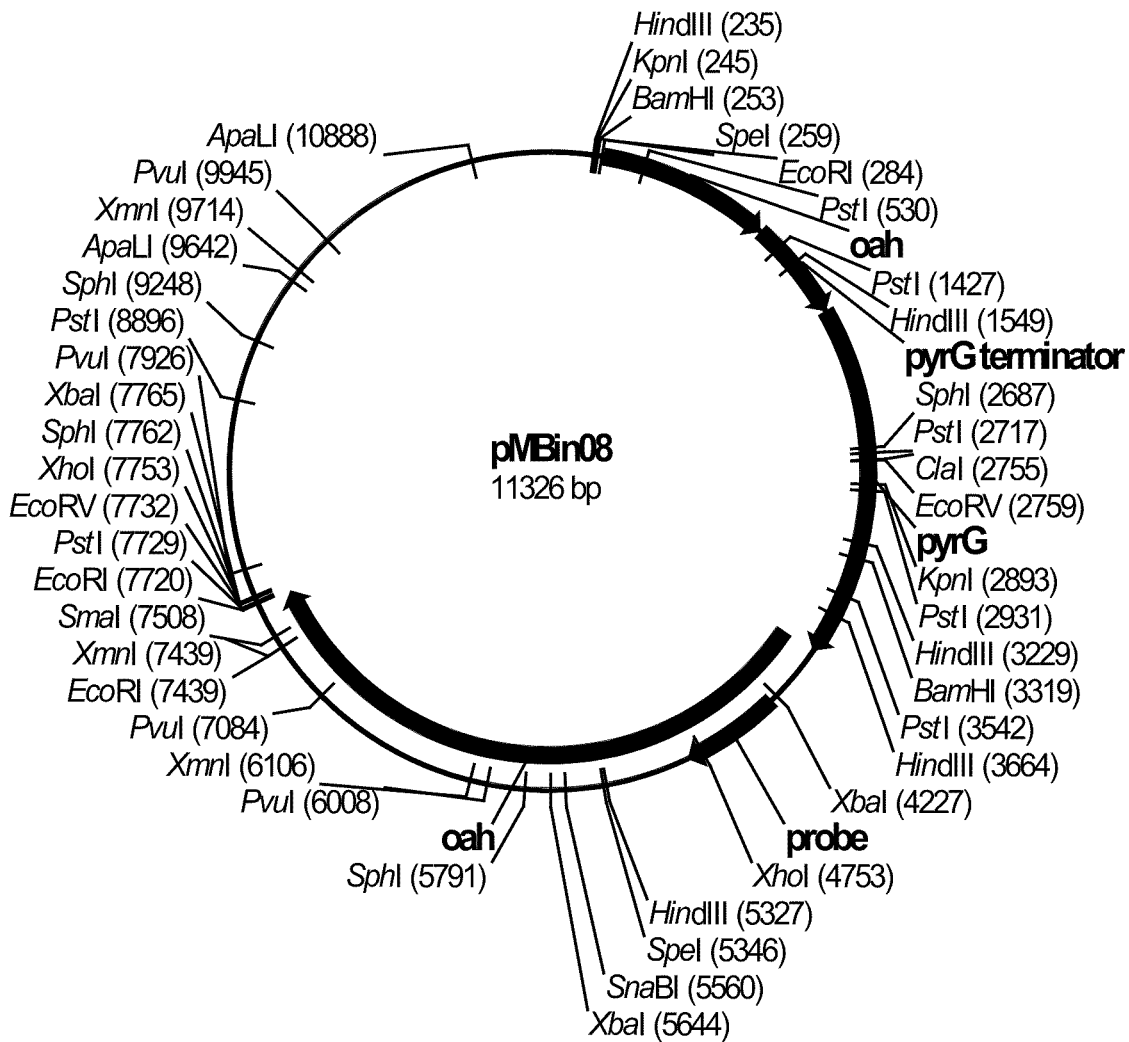
FIG. 11 shows a restriction map of pMBin08.

A 285 bp deletion, which included 156 bp of the promoter and 129 bp of the oxalic acid hydrolase gene coding sequence, was removed by digesting pHP1 with BstEII. The pMBin01 SpeI fragment described in Example 4 was blunt end ligated into this site to create pMBin08 (FIG. 11). Plasmid pMBin08 was digested with NotI and a fragment of 7155 bp was isolated using a QIAEX II Gel Extraction Kit following electrophoresis on a 1% agarose-TBE gel. The NotI fragment from pMBin08 was used to disrupt the oxalic acid hydrolase gene in *Aspergillus niger* MBin119.

*Aspergillus niger* MBin119 was transformed with the NotI fragment from pMBin08 using the transformation procedure described in Example 1. Forty-nine transformants were obtained and screened for oxalate production using a Sigma Oxalate Kit (number 591, Sigma Diagnostics, St. Louis, Mo.). The transformants were cultivated in shake flasks by inoculating conidia of transformants at a density of ca. $10^4$ per ml into 125 ml shake flasks containing 20 ml of YP medium supplemented with 5% glucose. The shake flasks were incubated 3 to 6 days at 37° C. and 200 rpm. Samples of 5 µl of the shake flask cultures were removed at day 3 and centrifuged to produce supernatants for enzyme assay. The day 3 supernatants were added to wells in a 96 well plate followed by the oxalate kit reagents as specified by the manufacturer, but at 1/10th of the volume. Production of oxalate was measured spectrophotometrically at 590 nm. One transformant produced no detectable oxalate and was single colony isolated twice on minimal medium supplemented with 10 mM uridine.

A fragment comprising 579 bp of sequence from within the oxalic acid hydrolase gene (404 bp downstream of the start codon) was PCR amplified for use as a probe in Southern blot analysis using primers 13 and 14.

```
Primer 13:
5'-CTACGACATGAAGACCAACGC-3'    (SEQ ID NO: 25)

Primer 14:
5'-GCACCGTTCTCCACCATGTTG-3'    (SEQ ID NO: 26)
```

PCR amplification was conducted in 50 µl reactions composed of 10 ng of pMBin08 plasmid DNA, 50 pmol of each primer, 2.5 mM each of dATP, dCTP, dGTP, and dTTP, 1×PCR Buffer with 2.5 mM MgCl$_2$, and 2.5 units of Taq DNA polymerase. The reactions were performed in a RoboCycler 40 thermacycler programmed for 1 cycle at 95° C. for 3 minutes; 30 cycles each at 95° C. for 1 minute, 60° C. for 1 minute, and 72° C. for 1 minute; and 1 cycle at 72° C. for 5 minutes.

The probe was isolated and labeled as described in Example 2. Genomic DNA from the transformant, as well as *Aspergillus niger* Bo-1 and *Aspergillus niger* MBin118 as controls, was isolated as described in Example 2 and digested with NdeI and SspI. Southern analysis of *Aspergillus niger* control strains Bo-1 and MBin118 with the probe above revealed a 2.5 kb band corresponding to the undisrupted oxalic acid hydrolase gene. The transformant had a 4.9 kb band consistent with the insertion of the disruption cassette at the oxalic acid hydrolase gene locus. The transformant was designated *Aspergillus niger* MBin120.

Example 13

Expression Analysis of *Aspergillus niger* General Host Strains

The ability of the general host *Aspergillus niger* strains to produce glucoamylase, acid stable alpha-amylase, neutral alpha-amylase, and protease was evaluated by cultivating the strains in shake flasks and/or fermentors. *Aspergillus niger* Bo-1 was run as a control.

Conidia of the *Aspergillus niger* strains at a density of ca. 10$^4$ per ml were inoculated into 125 ml shake flasks containing 20 ml of YP medium supplemented with 5% glucose. The shake flasks were incubated 3 to 6 days at 37° C. and 200 rpm. Samples of the shake flask cultures were removed at days 3-6 and centrifuged to produce supernatants for enzyme assay.

*Aspergillus niger* strains were also inoculated into 2 liter fermentors containing 1.8 liters of medium composed per liter of 2 g of MgSO$_4$.7H$_2$O, 2 g of KH$_2$PO$_4$, 2 g of citric acid, 2 g of K$_2$SO$_4$, 0.5 ml of AMG trace metals solution, 300 g of high maltose syrup, 1.8 g of CaCl$_2$.2H$_2$O, and 1.8 ml of pluronic acid. The fermentation medium was fed with a medium composed per liter of 50 g of urea and 5 ml of pluronic acid. The conditions of the fermentations were 34° C. at pH 4.5+/−0.05, 1.0 vvm aeration, and 1000 rpm for 8 days. Samples of the fermentations were removed at days 1-8 and centrifuged to produce supernatants for enzyme assay.

Glucoamylase activity was measured at 25° C. in 0.1 M sodium acetate at pH 4.3 using maltose as the substrate. Glucose was measured using the Sigma Trinder color reagent (Sigma reagent kit 315-100, Sigma Chemical Co., St. Louis, Mo.) at 490 nm according to the manufacturer's instructions. AMG™ (Novozymes A/S, Bagsværd, Denmark; batch 7-195) was used as a standard with glucoamylase activity measured in AGU/ml.

*Aspergillus niger* SMO110 was determined to produce no detectable glucoamylase activity (less than 0.5 AGU/ml in day 4 shake flask samples). *Aspergillus niger* MBin111 was determined to produce no detectable glucoamylase activity (less than 0.5 AGU/ml in day 4 shake flask or fermentation samples).

Acid stable and neutral alpha-amylase activity was measured at pH 4.5 and pH 7.0, respectively, using a Sigma alpha-amylase substrate (Sigma Kit #577, Sigma Chemical Co., St. Louis, Mo.) at 30° C. Detection was at 405 nm. Fungamyl™ was used as a standard and activity was reported in FAU/ml.

Acid stable alpha-amylase activity was found to be barely detectable with *Aspergillus niger* MBin113, MBin116, and MBin118 (>0.1 FAU/ml in both day 3 shake flask or fermentation samples) compared to *Aspergillus niger* Bo-1 (51 FAU/ml in day 5 fermentation samples). Neutral alpha-amylase activity was substantially reduced with *Aspergillus niger* MBin114 (not detectable from day 3 shake flask samples and 5.7 FAU/ml in day 5 fermentation samples) and barely detectable with *Aspergillus niger* MBin118 (0.5 FAU/ml in day 5 fermentation samples) compared to *Aspergillus niger* Bo-1 in fermentation samples.

General protease activity was determined using FITC-casein as substrate (Sigma Chemical Co., St. Louis, Mo.). The assay was conducted by mixing 40 µl of FITC-casein substrate (stock solution: 1:1 with 0.1 M potassium phosphate pH 6.0 or 0.1 M sodium citrate pH 5.0) with 10 µl of culture sample diluted appropriately in 0.1 M potassium phosphate pH 6.0 or 0.1 M sodium citrate pH 5.0 and incubating the solution for 1 hour at 37° C. After the 1 hour incubation, the reaction was quenched with 150 µl of 5% trichloroacetic acid and incubated in a cold room for 1 hour. The quenched reaction was transferred to an Eppendorf tube and centrifuged for 10 minutes. A 10 µl aliquot of the supernatant was transferred to a test tube containing 1 ml of 0.5 M borate pH 9.0 and mixed. A 200 µl aliquot of the solution was transferred to a black "U" bottom 96 well plate (ThermoLabsystems, Franklin, Mass.). Fluorescence was measured using a Fluorolite 1000 instrument (ThermoLabsystems, Franklin, Mass.) using reference channel 3 and a setting of 1176. Activity was measured in protease fluorescent units.

With the deletion of the prtT gene in *Aspergillus niger* MBin114, total protease activity dropped to about 20% of *Aspergillus niger* Bo-1. Day 6 fermentation samples of MBin114 had a protease activity of 692 while Bo-1 was at 3953 fluorescent units/ml.

Example 14

Expression of *Candida antarctica* Lipase B in *Aspergillus niger* MBin114, MBin118 and MBin120

The *Candida antarctica* lipase B gene (SEQ ID NOs: 27 [DNA sequence] and 28 [deduced amino acid sequence]) was cloned as described in U.S. Pat. No. 6,020,180. Plasmid pMT1335 containing the lipase B gene was constructed as described by Hoegh et al., in *Can. J. Bot.* 73 (Suppl. 1): S869-S875 (1995). Plasmid pTOC90 containing an *Aspergillus nidulans* amdS gene was constructed as described in WO 91/17243. Plasmids pMT1335 and pTOC90 were co-transformed into *Aspergillus niger* MBin114 according to the protocol described in Example 1 and transformants were selected on acetamide.

Thirty transformants were isolated by streaking to acetamide plates. Conidia were collected from the transformants and used to inoculate shake flasks as described in Example 13. Samples of the shake flask cultures were removed at days 3-6 and centrifuged to produce supernatants for enzyme assay.

In order to assess the effect disruption of the prtT gene had on the total level of protease activity and the yield of *Candida antarctica* lipase B (CLB), both protease and lipase B activities were determined. Several transformants produced lipase B and the highest producer was evaluated by fermentation.

*Aspergillus niger* MBin114 and *Aspergillus niger* Bo-1, as a control, were cultivated in 2 liter fermentors as described in Example 13.

General protease activity was measured as described in Example 9.

Lipase B assays were performed at pH 7 with a p-nitrophenyl butyrate (Sigma Chemical Co., St. Louis, Mo.) as substrate. Culture supernatants were diluted as appropriate in 0.1 M MOPS-4 mM $CaCl_2$ pH 7.0. A 100 μl aliquot of a culture supernatant was added to 100 μl of p-nitrophenyl butyrate substrate solution in wells of a 96 well microplate. The p-nitrophenyl butyrate substrate solution was composed of 10 μl of p-nitrophenyl butyrate, 990 μl of DMSO, and 4 ml of 0.1 M MOPS-4 mM $CaCl_2$ pH 7.0. Lipase activity was measured spectrophotometrically at 405 nm using a *Candida antarctica* lipase B standard (Novozymes Japan Ltd., Chiba-shi, Japan) to calculate LU/ml.

Figure 12:
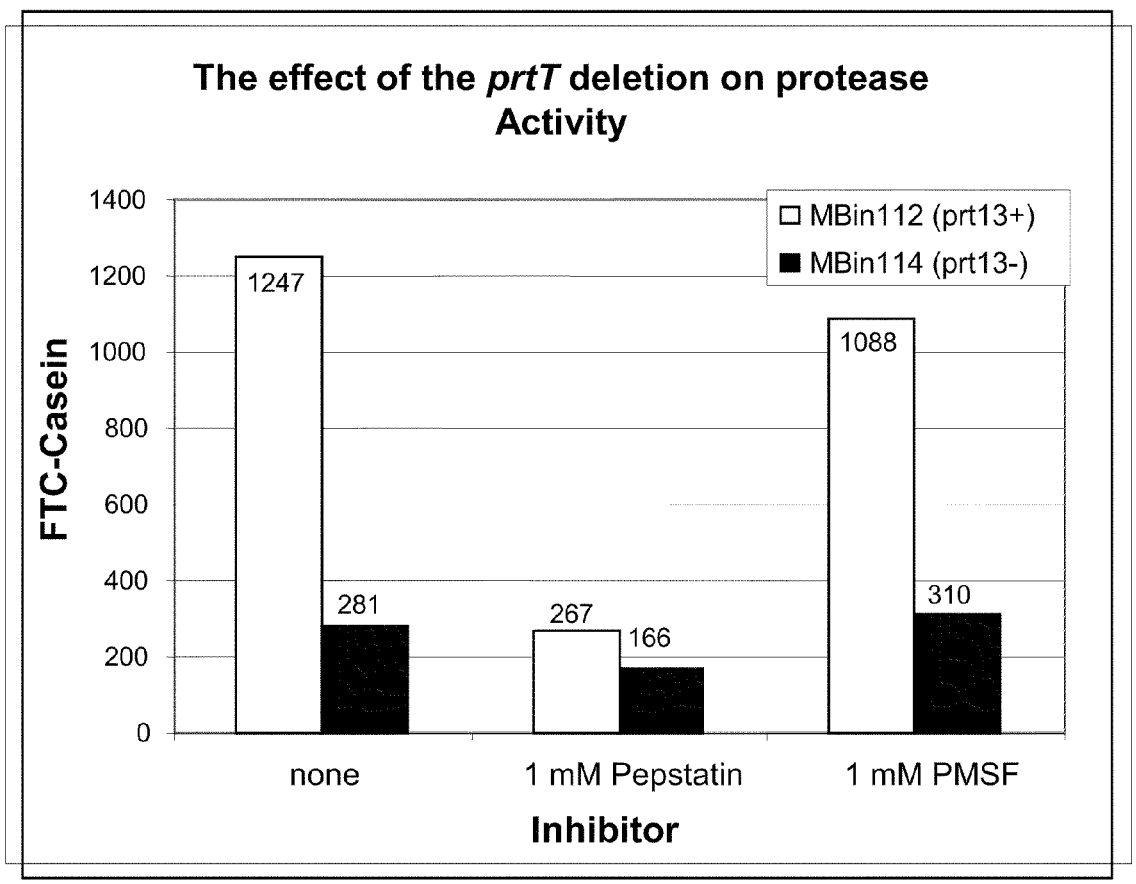
FIG. 12 shows the effect of the prtT deletion on protease activity.
Figure 13:
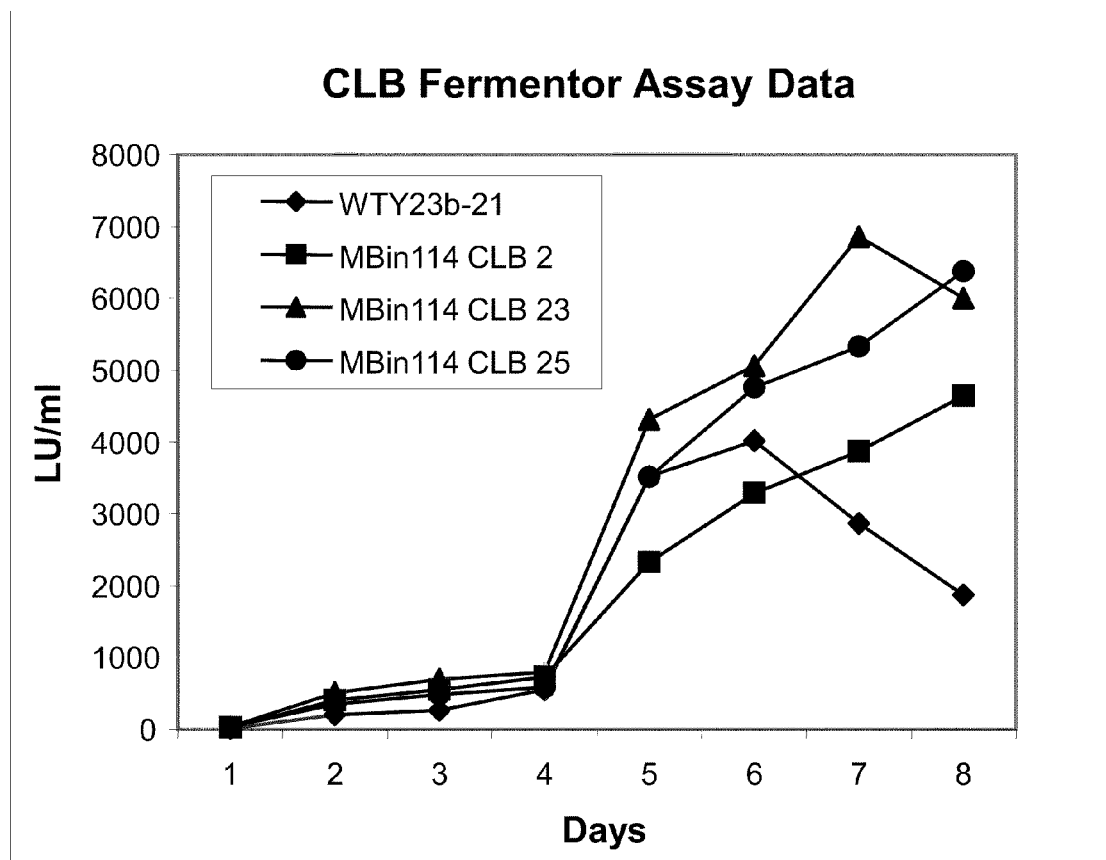
FIG. 13 shows the effect of the prtT deletion on *Candida antarctica* lipase B activity.
Figure 14:
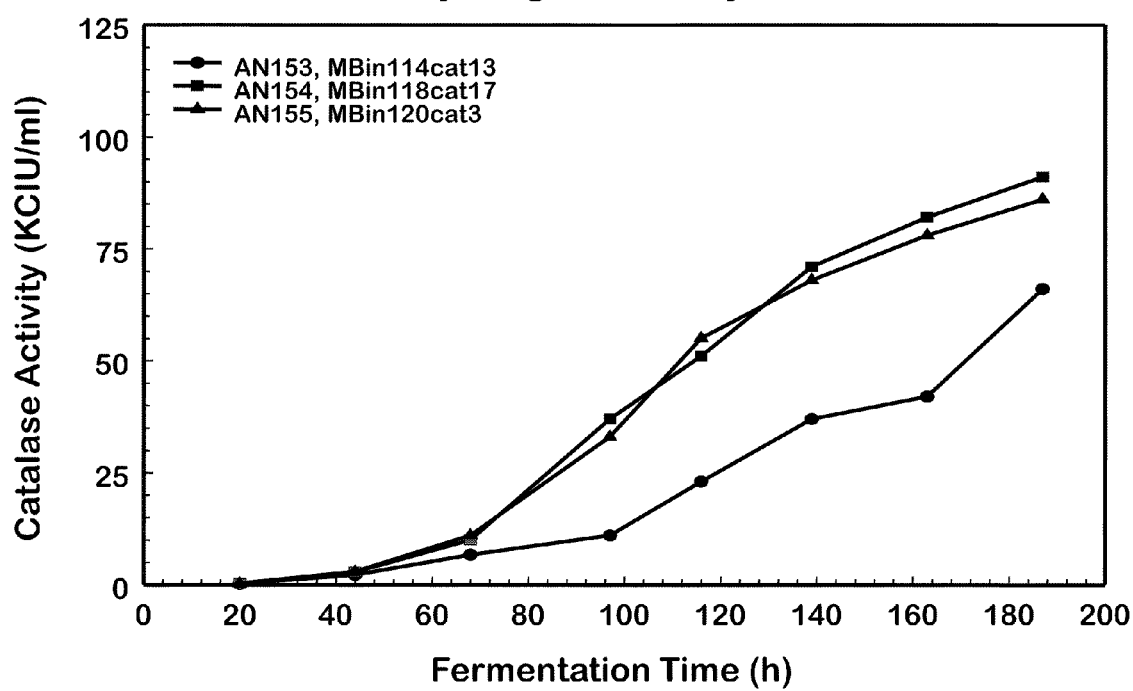
FIG. 14 shows a comparison of *Scytalidium thermophilum* catalase production in *Aspergillus niger* general host strains MBin114, MBin118 and MBin120.

FIGS. 14 and 15 show the results of these assays. Total protease activity dropped to about 20% of wildtype (see Example 13, FIG. 12) and lipase B activity rose steadily throughout the fermentation (FIG. 13).

Example 15

Expression of *Scytalidium thermophilum* Catalase in *Aspergillus niger MBin*114, MBin118 and MBin120

The *Scytalidium thermophilum* catalase gene (SEQ ID NOs: 29 [DNA sequence] and 30 [deduced amino acid sequence]) was cloned as described in U.S. Pat. No. 5,646, 025. Plasmid pDM153 containing the catalase gene was constructed as described in U.S. Pat. No. 5,646,025. Plasmid pDM153 was transformed into *Aspergillus niger* strains MBin114, MBin118, and MBin120 according to the protocol described in Example 1.

Forty transformants were selected and cultivated in 24 well plates containing 1.5 ml of a 1:4 dilution of M400 medium. The plates were incubated for 90 hours at 34° C. and 125 rpm. Samples for assay were removed at 90 hours. The three transformants that produced the highest level of catalase activity were evaluated in fermentors.

Catalase activity was measured at 25° C. in 10 mM phosphate pH 7 buffer containing 18.2 μl of a stock hydrogen peroxide solution. The stock hydrogen peroxide solution was composed of 30% hydrogen peroxide per 10 ml of 10 mM potassium phosphate pH 7. A 25 μl aliquot of culture supernatant was added to 25 μl of hydrogen peroxide stock solution in wells of a 96 well microplate. Following 5 minutes of incubation, 200 μl of titanium reagent was added and the absorbance was read at 405 nm. The titanium reagent was composed of 1.0 g of titanium oxide and 10 g of $K_2SO_4$, which was digested for 2-3 hours with 150 ml of concentrated $H_2SO_4$ at 180-220° C., allowed to cool, and then diluted with 1.5 liters of deionized water. The catalase activity was measured spectrophotometrically at 405 nm using Catazyme™ (Novozymes A/S, Bagsværd, Denmark, batch 31-2197) as a standard and reported in KCIU/ml.

*Aspergillus niger* strains MBin114, MBin118, and MBin120 were cultivated in 2 liter fermentors as described in Example 13.

FIG. 15 shows a comparison of *Scytalidium thermophilum* catalase production in *Aspergillus niger* general host strains MBin114, MBin118 and MBin120. No obvious change in enzyme production was observed in any of the strains tested.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A mutant of a parent *Aspergillus niger* strain, comprising a first nucleotide sequence encoding a heterologous polypeptide and one or more second nucleotide sequences comprising a modification of glaA, asa, amyA, amyB, and oah, wherein the mutant strain is deficient in glucoamylase, acid stable alpha-amylase, neutral alpha-amylase A, neutral alpha-amylase B, and oxalic acid hydrolase compared to the parent *Aspergillus niger* strain when cultivated under identical conditions.

2. The mutant strain of claim 1, wherein the heterologous polypeptide encoded by the first nucleotide sequence is an antibody, antigen, antimicrobial peptide, enzyme, growth factor, hormone, immunodilator, neurotransmitter, receptor, reporter protein, structural protein, or transcription factor.

3. The mutant strain of claim 2, wherein the enzyme is an oxidoreductase, transferase, hydrolase, lyase, isomerase, or ligase.

4. The mutant strain of claim 1, which produces at least 25% less enzyme for each of glucoamylase, acid stable alpha-amylase, neutral alpha-amylase A, neutral alpha-amylase B, and oxalic acid hydrolase compared to the parent *Aspergillus niger* strain when cultured under identical conditions.

5. The mutant strain of claim 1, which is completely deficient in glucoamylase, acid stable alpha-amylase, neutral alpha-amylase A, neutral alpha-amylase B, and oxalic acid hydrolase compared to the parent *Aspergillus niger* strain when cultured under identical conditions.

6. The mutant strain of claim 1, which further comprises a modification of one or more genes which encode an enzyme having proteolytic activity, which is selected from the group consisting of an aminopeptidase, dipeptidylaminopeptidase, tripeptidylaminopeptidase, carboxypeptidase, aspergillopepsin, serine protease, metalloprotease, cysteine protease, and vacuolar protease.

7. A method for obtaining the mutant of claim 1, comprising:
(a) introducing into a parent *Aspergillus niger* strain a first nucleotide sequence encoding a heterologous polypeptide and one or more second nucleotide sequences comprising a modification of glaA, asa, amyA, amyB, and oah; and (b) identifying the mutant strain from step (a) comprising the modified nucleotide sequence, wherein the mutant strain is deficient in the production of glucoamylase, acid stable alpha-amylase, neutral alpha-amylase A, neutral alpha-amylase B, and oxalic acid hydrolase compared to the parent *Aspergillus niger* strain when cultivated under identical conditions.

8. The method of claim 7, wherein the heterologous polypeptide encoded by the first nucleotide sequence is an antibody, antigen, antimicrobial peptide, enzyme, growth factor, hormone, immunodilator, neurotransmitter, receptor, reporter protein, structural protein, or transcription factor.

9. The method of claim 8, wherein the enzyme is an oxidoreductase, transferase, hydrolase, lyase, isomerase, or ligase.

10. The method of claim 7, wherein the mutant strain produces at least 25% less enzyme for each of glucoamylase, acid stable alpha-amylase, neutral alpha-amylase A, neutral alpha-amylase B, and oxalic acid hydrolase compared to the parent *Aspergillus niger* strain when cultured under identical conditions.

11. The method of claim 7, wherein the mutant strain is completely deficient in glucoamylase, acid stable alpha-amylase, neutral alpha-amylase A, neutral alpha-amylase B, and oxalic acid hydrolase compared to the parent *Aspergillus niger* strain when cultured under identical conditions.

* * * * *

SEQUENCE LISTING

<160> NUMBER OF SEQ ID NOS: 30

<210> SEQ ID NO 1
<211> LENGTH: 1517
<212> TYPE: DNA
<213> ORGANISM: Aspergillus niger

<400> SEQUENCE: 1

```
gcagggaaaa atacgagctc caatgaacct gggtgtggca acttcaatgg aaaggaactg      60
cctttgcagg tgtggctgaa ccccacggtt ccggtcggag gcggcgaaat cacccgatgt     120
ggctggtgcg tggagggtcg cgatgattta ctgagctcct cttttgctcg acattgaatg     180
tgcattgttc acctcatata agggccagtc gctgctaaat tattcggtag tatttgcgca     240
tctctggatc taccaattag ggcctatcag tcgaaactcc aagctactca tattgcacaa     300
gcctctttca tccccgcatt aaccccctcca ccgacaccat gtcctccaag tcgcaattga     360
cctacactgc ccgtgccagc aagcacccca atgctctggc caagcggctg ttcgaaattg     420
```

```
ctgaggccaa gaagaccaat gtgaccgtct ctgccgacgt taccaccact aaggagctac    480
tagatcttgc tgaccgtagg ccgacccgcc attctgcctg tttatgctgc atacaaactt    540
attaacggtg ataccggact gaggtctcgg tccctacatc gccgtgatca aacccacat     600 cgatatcctc tctgacttca gcgacgagac cattgagggc ctcaaggctc ttgcgcagaa    660
gcacaacttc ctcatcttcg aggaccgcaa attcatcgac attggcaaca ctgtccagaa    720
gcaataccac cgtggtaccc tccgcatctc agaatgggcc catatcatca actgcagcat    780
cctgcctggc gagggtatcg tcgaggctct cgctcagacg gcgtctgcac cggacttctc    840
ctacggcccc gaacgtggtc tgttgatctt ggcggaaatg acctctaagg gttccttggc    900
caccggccag tacactactt cttcggttga ttatgcccgg aaatacaaga acttcgtcat    960
gggatttgtg tcgacccgct cgttgggtga ggtgcagtcg gaagtcagct ctccttcgga   1020
tgaggaggac tttgtggtct tcacgactgg tgtgaacatt tcgtccaagg gagataagct   1080
cggtcagcag taccagactc ccgcatcggc tatcggtcgg ggtgctgact tcattatcgc   1140
gggtcgcggt atctacgccg cgccggaccc ggtgcaggct gcgcaacagt accagaagga   1200
aggttgggag gcgtacctgg cccgtgtcgg cggaaactaa tactataaaa tgaggaaaaa   1260
agttttgatg gttatgaatg atatagaaat gcaacttgcc gctacgatac gcatacaaac   1320
taatgtcgag cacgggtagt cagactgcgg catcggatgt caaaacggta ttgatcctgc   1380
aggctattat agggtggcac gggattaatg cggtacgacg atttgatgca gataagcagg   1440
ctgcgaagta cttagtcctg taactcttgc gtagagcaaa tggcgacggg tggctgataa   1500
gggacggtga taagctt                                                  1517

<210> SEQ ID NO 2
<211> LENGTH: 277
<212> TYPE: PRT
<213> ORGANISM: Aspergillus niger

<400> SEQUENCE: 2

Met Ser Ser Lys Ser Gln Leu Thr Tyr Thr Ala Arg Ala Ser Lys His
 1               5                  10                  15

Pro Asn Ala Leu Ala Lys Arg Leu Phe Glu Ile Ala Glu Ala Lys Lys
            20                  25                  30

Thr Asn Val Thr Val Ser Ala Asp Val Thr Thr Lys Glu Leu Leu
        35                  40                  45

Asp Leu Ala Asp Arg Leu Gly Pro Tyr Ile Ala Val Ile Lys Thr His
    50                  55                  60

Ile Asp Ile Leu Ser Asp Phe Ser Asp Glu Thr Ile Glu Gly Leu Lys
65                  70                  75                  80

Ala Leu Ala Gln Lys His Asn Phe Leu Ile Phe Glu Asp Arg Lys Phe
                85                  90                  95

Ile Asp Ile Gly Asn Thr Val Gln Lys Gln Tyr His Arg Gly Thr Leu
            100                 105                 110

Arg Ile Ser Glu Trp Ala His Ile Ile Asn Cys Ser Ile Leu Pro Gly
        115                 120                 125

Glu Gly Ile Val Glu Ala Leu Ala Gln Thr Ala Ser Ala Pro Asp Phe
    130                 135                 140

Ser Tyr Gly Pro Glu Arg Gly Leu Leu Ile Leu Ala Glu Met Thr Ser
145                 150                 155                 160

Lys Gly Ser Leu Ala Thr Gly Gln Tyr Thr Thr Ser Ser Val Asp Tyr
                165                 170                 175

Ala Arg Lys Tyr Lys Asn Phe Val Met Gly Phe Val Ser Thr Arg Ser
```

```
                      180                 185                 190
Leu Gly Glu Val Gln Ser Glu Val Ser Ser Pro Ser Asp Glu Glu Asp
        195                 200                 205

Phe Val Val Phe Thr Thr Gly Val Asn Ile Ser Ser Lys Gly Asp Lys
    210                 215                 220

Leu Gly Gln Gln Tyr Gln Thr Pro Ala Ser Ala Ile Gly Arg Gly Ala
225                 230                 235                 240

Asp Phe Ile Ile Ala Gly Arg Gly Ile Tyr Ala Ala Pro Asp Pro Val
                245                 250                 255

Gln Ala Ala Gln Gln Tyr Gln Lys Glu Gly Trp Glu Ala Tyr Leu Ala
            260                 265                 270

Arg Val Gly Gly Asn
        275

<210> SEQ ID NO 3
<211> LENGTH: 30
<212> TYPE: DNA
<213> ORGANISM: Aspergillus niger

<400> SEQUENCE: 3
gggactagtg gatcgaagtt ctgatggtta                                        30

<210> SEQ ID NO 4
<211> LENGTH: 30
<212> TYPE: DNA
<213> ORGANISM: Aspergillus niger

<400> SEQUENCE: 4
ataccgcggg tttcaaggat ggagatagga                                        30

<210> SEQ ID NO 5
<211> LENGTH: 2103
<212> TYPE: DNA
<213> ORGANISM: Aspergillus niger

<400> SEQUENCE: 5 tccctttag gcgcaactga gagcctgagc ttcatcccca gcatcattac acctcagcaa         60
tgtcgttccg atctctactc gccctgagcg gcctcgtctg cacagggttg caaatgtga       120 tttccaagcg cgcgaccttg gattcatggt tgagcaacga agcgaccgtg gctcgtactg      180
ccatcctgaa taacatcggg gcggacggtg cttgggtgtc gggcgcggac tctggcattg      240
tcgttgctag tccagcacg gataacccgg actacttcta cacctggact cgcgactctg       300
gtctcgtcct caagacccctc gtcgatctct ccgaaatgg agataccagt ctcctctcca      360
ccattgagaa ctacatctcc gcccaggcaa ttgtccaggg tatcagtaac ccctctggtg      420
atctgtccag cggcgctggt ctcggtgaac ccaagttcaa tgtcgatgag actgcctaca      480
ctggttcttg gggacggccg cagcgagatg gtccggctct gagagcaact gctatgatcg      540
gcttcgggca gtggctgctt gacaatggct acaccagcac cgcaacggac attgtttggc      600
ccctcgttag gaacgacctg tcgtatgtgg ctcaatactg gaaccagaca ggatatgatc      660
tctgggaaga agtcaatggc tcgtctttct ttacgattgc tgtgcaacac cgcgcccttg      720
tcgaaggtag tgccttcgcg acggccgtcg gctcgtcctg ctcctggtgt gattctcagg      780
cacccgaaat tctctgctac ctgcagtcct tctggaccgg cagcttcatt ctggccaact      840
tcgatagcag ccgttccggc aaggacgcaa acacctcct gggaagcatc acacctttg       900 atcctgaggc cgcatgcgac gactccacct tccagccctg ctcccgcgc gcgctcgcca      960
```

```
accacaagga ggttgtagac tctttccgct caatctatac cctcaacgat ggtctcagtg    1020
acagcgaggc tgttgcggtg ggtcggtacc ctgaggacac gtactacaac ggcaacccgt    1080
ggttcctgtg caccttggct gccgcagagc agttgtacga tgctctatac cagtgggaca    1140 agcagggtc gttggaggtc acagatgtgt cgctggactt cttcaaggca ctgtacagcg    1200
atgctgctac tggcacctac tcttcgtcca gttcgactta tagtagcatt gtagatgccg    1260
tgaagacttt cgccgatggc ttcgtctcta ttgtggaaac tcacgccgca agcaacggct    1320
ccatgtccga gcaatacgac aagtctgatg gcgagcagct ttccgctcgc gacctgacct    1380
ggtcttatgc tgctctgctg accgccaaca accgtcgtaa ctccgtcgtg cctgcttctt    1440
ggggcgagac ctctgccagc agcgtgcccg gcacctgtgc ggccacatct gccattggta    1500
cctacagcag tgtgactgtc acctcgtggc cgagtatcgt ggctactggc ggcaccacta    1560
cgacggctac ccccactgga tccggcagcg tgacctcgac cagcaagacc accgcgactg    1620
ctagcaagac cagcaccagt acgtcatcaa cctcctgtac cactcccacc gccgtggctg    1680
tgactttcga tctgacagct accaccacct acggcgagaa catctacctg gtcggatcga    1740
tctctcagct gggtgactgg gaaaccagcg acggcatagc tctgagtgct gacaagtaca    1800
cttccagcga cccgctctgg tatgtcactg tgactctgcc ggctggtgag tcgtttgagt    1860
acaagtttat ccgcattgag agcgatgact ccgtggagtg ggagagtgat cccaaccgag    1920
aatacaccgt tcctcaggcg tgcggaacgt cgaccgcgac ggtgactgac acctggcggt    1980
gacaatcaat ccatttcgct atagttaaag gatggggatg agggcaattg gttatatgat    2040
catgtatgta gtgggtgtgc ataatagtag tgaaatggaa gccaagtcat gtgattgtaa    2100
tcg                                                                 2103
```

<210> SEQ ID NO 6
<211> LENGTH: 662
<212> TYPE: PRT
<213> ORGANISM: Aspergillus niger

<400> SEQUENCE: 6

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Phe Thr Ile
        35                  40                  45

Gly Ala Asp Gly Ala Trp Val Ser Gly Ala Asp Ser Gly Ile Val Val
    50                  55                  60

Ala Ser Pro Ser Thr Asp Asn Pro Asp Tyr Phe Tyr Thr Trp Thr Arg
65                  70                  75                  80

Asp Ser Gly Leu Val Leu Lys Thr Leu Val Asp Leu Phe Arg Asn Gly
                85                  90                  95

Asp Thr Ser Leu Leu Ser Thr Ile Glu Asn Phe Thr Tyr Ile Ser Ala
            100                 105                 110

Gln Ala Ile Val Gln Gly Ile Ser Asn Pro Ser Gly Asp Leu Ser Ser
        115                 120                 125

Gly Ala Gly Leu Gly Glu Pro Lys Phe Asn Val Asp Glu Thr Ala Tyr
    130                 135                 140

Thr Gly Ser Trp Gly Arg Pro Gln Arg Asp Gly Pro Ala Leu Arg Ala
145                 150                 155                 160

Thr Ala Met Ile Gly Phe Gly Phe Thr Gln Trp Leu Leu Asp Asn Gly
                165                 170                 175
```

```
Tyr Thr Ser Thr Ala Thr Asp Ile Val Trp Pro Leu Val Arg Asn Asp
            180                 185                 190

Leu Ser Tyr Val Ala Gln Tyr Trp Asn Gln Thr Gly Tyr Asp Leu Trp
            195                 200                 205

Glu Glu Val Asn Gly Ser Ser Phe Phe Thr Ile Ala Val Gln His Arg
210                 215                 220

Ala Leu Val Glu Phe Thr Gly Ser Ala Phe Ala Thr Ala Val Gly Ser
225                 230                 235                 240

Ser Cys Ser Trp Cys Asp Ser Gln Ala Pro Glu Ile Leu Cys Tyr Leu
                245                 250                 255

Gln Ser Phe Trp Thr Gly Ser Phe Ile Leu Ala Asn Phe Asp Ser Ser
            260                 265                 270

Arg Ser Gly Lys Asp Ala Asn Thr Leu Leu Gly Ser Ile His Thr Phe
            275                 280                 285

Asp Phe Thr Pro Glu Ala Ala Cys Asp Asp Ser Thr Phe Gln Pro Cys
            290                 295                 300

Ser Pro Arg Ala Leu Ala Asn His Lys Glu Val Val Asp Ser Phe Arg
305                 310                 315                 320

Ser Ile Tyr Thr Leu Asn Asp Gly Leu Ser Asp Ser Glu Ala Val Ala
                325                 330                 335

Val Gly Arg Tyr Pro Glu Asp Thr Tyr Tyr Asn Gly Asn Pro Phe Thr
            340                 345                 350

Trp Phe Leu Cys Thr Leu Ala Ala Ala Glu Gln Leu Tyr Asp Ala Leu
            355                 360                 365

Tyr Gln Trp Asp Lys Gln Gly Ser Leu Glu Val Thr Asp Val Ser Leu
370                 375                 380

Asp Phe Phe Lys Ala Leu Tyr Ser Asp Ala Ala Thr Gly Thr Tyr Ser
385                 390                 395                 400

Ser Ser Ser Ser Thr Tyr Ser Ser Ile Val Asp Phe Thr Ala Val Lys
                405                 410                 415

Thr Phe Ala Asp Gly Phe Val Ser Ile Val Glu Thr His Ala Ala Ser
            420                 425                 430

Asn Gly Ser Met Ser Glu Gln Tyr Asp Lys Ser Asp Gly Glu Gln Leu
            435                 440                 445

Ser Ala Arg Asp Leu Thr Trp Ser Tyr Ala Ala Leu Leu Thr Ala Asn
450                 455                 460

Asn Arg Arg Asn Ser Val Val Pro Phe Thr Ala Ser Trp Gly Glu Thr
465                 470                 475                 480

Ser Ala Ser Ser Val Pro Gly Thr Cys Ala Ala Thr Ser Ala Ile Gly
                485                 490                 495

Thr Tyr Ser Ser Val Thr Val Thr Ser Trp Pro Ser Ile Val Ala Thr
            500                 505                 510

Gly Gly Thr Thr Thr Thr Ala Thr Pro Thr Gly Ser Gly Ser Val Thr
            515                 520                 525

Ser Thr Ser Lys Thr Thr Phe Thr Thr Ala Thr Ala Ser Lys Thr Ser Thr
530                 535                 540

Ser Thr Ser Ser Thr Ser Cys Thr Thr Pro Thr Ala Val Ala Val Thr
545                 550                 555                 560

Phe Asp Leu Thr Ala Thr Thr Thr Tyr Gly Glu Asn Ile Tyr Leu Val
                565                 570                 575

Gly Ser Ile Ser Gln Leu Gly Asp Trp Glu Thr Ser Asp Gly Ile Ala
            580                 585                 590

Leu Ser Phe Thr Ala Asp Lys Tyr Thr Ser Ser Asp Pro Leu Trp Tyr
```

```
              595               600              605
Val Thr Val Thr Leu Pro Ala Gly Glu Ser Phe Glu Tyr Lys Phe Ile
    610               615              620

Arg Ile Glu Ser Asp Asp Ser Val Glu Trp Glu Ser Asp Pro Asn Arg
625              630               635              640

Glu Tyr Thr Val Pro Gln Ala Cys Gly Thr Ser Thr Ala Thr Val Phe
             645              650              655

Thr Thr Asp Thr Trp Arg
        660

<210> SEQ ID NO 7
<211> LENGTH: 21
<212> TYPE: DNA
<213> ORGANISM: Aspergillus niger

<400> SEQUENCE: 7
actagtggcc ctgtacccag a                                        21

<210> SEQ ID NO 8
<211> LENGTH: 26
<212> TYPE: DNA
<213> ORGANISM: Aspergillus niger

<400> SEQUENCE: 8
gcatgcattg ctgaggtgta atgatg                                   26

<210> SEQ ID NO 9
<211> LENGTH: 21
<212> TYPE: DNA
<213> ORGANISM: Aspergillus niger

<400> SEQUENCE: 9
gaggtcgacg gtatcgataa g                                        21

<210> SEQ ID NO 10
<211> LENGTH: 33
<212> TYPE: DNA
<213> ORGANISM: Aspergillus niger

<400> SEQUENCE: 10
gcatgcagat ctcgagaata caccgttcct cag                           33

<210> SEQ ID NO 11
<211> LENGTH: 21
<212> TYPE: DNA
<213> ORGANISM: Aspergillus niger

<400> SEQUENCE: 11
ctcattggcc gaaactccga t                                        21

<210> SEQ ID NO 12
<211> LENGTH: 21
<212> TYPE: DNA
<213> ORGANISM: Aspergillus niger

<400> SEQUENCE: 12
agcagacgat gtcctgagct g                                        21

<210> SEQ ID NO 13
<211> LENGTH: 4098
<212> TYPE: DNA
<213> ORGANISM: Aspergillus niger
```

```
<400> SEQUENCE: 13
ttggtgctgg aaagcccatt taagggatct tataaggtaa ttgccaatgt tcagtcgcct      60
atggtctttg tcgagagaaa ctcttttctcg ttaagatcta catgatcgct tttgattttc    120
tctgggttca cgcggtactt tctccccgtc aatcccaac cgctgttgtg cctgaccatc     180
aatgtggaac ggataagggg acaagagaaa ttgaaggagc gatcataaaa agctaatttt    240
ggtttattat ttttttttct tataaaactc aaaaagaaa acgaaaacga aaaggaaaa     300
aagaaaaggt aaaatggaaa aagaaaggcg gtcatcactt ccaataacca tcagccaaag    360
atacagacga gttactgacc ttcttatcct ggacttccgc ccgatccata tcttcatgat    420
aagcagggaa ccgaacaaat caacgccaac ttcagcggca gttcctcact aatttcccac    480
ttcccaccgg cgtcattttg gtcccaaccc cctccctgga agcagcggga tttagttacg    540
atccggttta catcggagac tcggaaaata ccatagcgca tgccaatcaa aacccctccc    600
agggtgactg gccagtatca cgacccattg tttctatctt tctagaagac ctgcagggac    660
atggattggc tggccgccgt gctgccgtcc attagcgtct accccaggtc aagaacggac    720
tggacggacc cataaccaat ctaaccaaag ccaatttcgt caattcccag ctggcgagca    780
caatcccatt cccagggttg gccgccaact gttaaaaggc actatgtgtc tctccacctg    840
cccgcccccc tcgatggcct gcgcgtaata actattctac tgcttttgc ctcttacttg    900
cctcattatt agtattttac tctactctcc agattgcctg ccagcaattg gtccaaagtg    960
gactttgttt gatgacatga ctcgaaccgt ggacgagatc aaatacgaaa cgccttcttc   1020
atgggagcac aagagcttgg acgttgccga ggatggcagg cgactagctc cccattccga   1080
cactgctcgt ccgaaaggcc gcatacgacg atcgatgact gcctgtcaca catgtcggaa   1140
gcttaaaact agatgtgatc tagatccgcg cggtcatgcg tgccgtcgct gtctatctct   1200
aaggtcagag gcactaccta cctgccagtt gaagctttgt ccttctgaac gcgacatgat   1260
actagtcgtg gaatataact gtcccaactt tgctgacagt ccacaatatc tttagaatcg   1320
attgtaagct gcctgaaacg accgaccgct tccaagacag tgctgcgatg tggccagacg   1380
ccacctcggc aattccctcc atcgaggagc gcctcacctc cctagaaaga tgcatgaggg   1440
agatgacggg catgatgcga cagatgctag atcactcccc aggtttcgca aatgcctcgg   1500
ttccgcattt gaccaaaagc atcatcacgg atgaaaccgc ctcgatggag ggaagcccgt   1560
cgtcccccctt cctgcctaag cccgttcgcc tcattcagga cctccagtcc gacttcttcg   1620
gagaagcaga gacttccccc gttgactccc ctctctccag cgatggtaac gccaagggcg   1680
ctatcgactc taagctatcc ctcaaattgt tgcaaacgta tgggtatacc tgattgacaa   1740
ttaccaaaaa gctgctaatc cttggcgcaa atcaggtttg tcgatcactt tggcgcttgc   1800
gtttccattt acaatctctc cgacatccac aacgacatga aagcccccga ctctttactg   1860
tataatactg catgccttct agcttcacgc tatgtaccgg ggataccgac atctaccgtg   1920
catgctatat accttcaagt gcgacatgca gtagtcaata ttttgtggga aaaccaccc    1980
ctgaagtatg agaccctcca agcacttgca cttctctgtc tctggccagc aaccgcccag   2040
aaagagccac ccatggacag ctggctgctg agtggtatct caattaacca tgcaattatc   2100
gcgctcgatt tcctaaacta tgcgcccctcg gaagtcatgg tggacaatga aacgcgctgcg   2160
cagctgcggc tatggaatac atattgcttg acacagctac agtgggtttc atctaagatc   2220
tcccgtccag aagatagcta acaagcttta gttttgcggt cgggaatgcg cgtcctttcc   2280
atatccagca aagataccctt gaccactgcc cacggatact ggagcaccca gcagcaactc   2340
```

```
tggaggacgc aagggttgta gcagaaatac agttgtattt gatgacattg cggctccaga    2400
gcaatagcag tcgaatgcgg ttggcggacc ttgactatga ggaaatagag cgatggaaga    2460
gggagtgggc tcaccttttc tgtaagaagc ctgttcttgt ttcccgggga ctaccactga    2520
cgagagcaac agctggggaa agttccacat tggagctgag cctttggttc tgccagacac    2580
tccttcaccg cacagcaatg aggcttcagc ccagatccga caggctcgca tctgaggttc    2640
tgcaaacctc acgtctgata atatcgcggt tcctccagat ccggtactct accgcattaa    2700
gccttgtcga ccaagtctat ttcattgtcg gctacgctgc actgaatctg tgcgatttca    2760
atcttatgga cccgcttatc gagcaagtgc agatgttcct gctgcatctc tccccgaacg    2820
aagaccacat cgcctaccgg ttttcgtgca tggtcgccga gttcaagcgg cgatgtggca    2880
gtgcggaatg caatgaccca tcatccactg tcaaggggtc tccgttatca tcctacggcg    2940
acagtcgtaa gatgagcatg gggcaagcac cgttcatgcc accgctcatg gatggcatga    3000
tcgagggta cggcttcgag caactgatgc cagaagtcat gccgagttcc tttccggatg    3060
ggatactcaa cggaatgcct gtgactgggc tagcagcgta tcggtcagcg acgctgtaag    3120
taatcgagat cggggttggaa aggacatgag tgggggtggt ggtggtagta gcagtaacac    3180
cagggatgat aacctgcagc ggtggtttag ttcctgccca tgggctgaac taaaaccccg    3240
aacctagcat gatgacgtgc aacgaaagga tcataaccaa ggccaagtaa atactaaaat    3300
aaaataatat aattccacac gatccactac caccaccacc accggatcca tcaggttgcc    3360
ttcctgcaca ggcctatta gttagagggc ccgtgccacg aaacatacg taattgagcg    3420
cttttgcttc cttgcaactt aaacaacccc atagacactc tcacattcac atgccaaact    3480
actaactcct actgaccacc agctgcagga agccagccag ccaccatttc ctaatcggat    3540
atatctccga aacgtacgct ttcctccttt gttcggaccg ttccgtgcct ccgcggagag    3600
ttgaacgagt cagaacacat tcttttcgtt tctatcgttt cttttccaag gcagcagaga    3660
gacgaacaag tcagtgcttg ctaactaact taccctcag catttagta aactactatt    3720
taggaaagag taatcattca tcgaagacaa gatgtttatt tctccgatcg accaaacaaa    3780
aacgttcagg tagactaagt agtagtagta gtatgtcttt gaccccttta ctccactatc    3840
cgttgactgc acatagtagt aagtaactat ctaaccagtt gccgaggaga ggaaagtgag    3900
tgggtgggag ccggaggatg ccgccgagaa ttattaagtc gatcattgct agttagttat    3960
cttttcatga tgaggagagg aaggagaggg gggacgggat tagagaaata aacttttctc    4020
tccaattaat tatctggatt aattaaaact tggagaggag ggtaggggag ttgggtattg    4080
gtatgttgct gtgaatgt                                                  4098
```

<210> SEQ ID NO 14
<211> LENGTH: 666
<212> TYPE: PRT
<213> ORGANISM: Aspergillus niger

<400> SEQUENCE: 14

```
Met Thr Arg Thr Val Asp Glu Ile Lys Tyr Glu Thr Pro Ser Ser Trp
1               5                   10                  15

Glu His Lys Ser Leu Asp Val Ala Glu Asp Gly Arg Arg Leu Ala Pro
            20                  25                  30

His Ser Asp Thr Ala Arg Pro Lys Gly Arg Ile Arg Arg Ser Met Thr
        35                  40                  45

Ala Cys His Thr Cys Arg Lys Leu Lys Thr Arg Cys Asp Leu Asp Pro
    50                  55                  60
```

```
Arg Gly His Ala Cys Arg Cys Leu Ser Leu Arg Ile Asp Cys Lys
 65                  70                  75                  80

Leu Pro Glu Thr Thr Asp Arg Phe Gln Asp Ser Ala Ala Met Trp Pro
                 85                  90                  95

Asp Ala Thr Ser Ala Ile Pro Ser Ile Glu Glu Arg Leu Thr Ser Leu
                100                 105                 110

Glu Arg Cys Met Arg Glu Met Thr Gly Met Met Arg Gln Met Leu Asp
            115                 120                 125

His Ser Pro Gly Phe Ala Asn Ala Ser Val Pro His Leu Thr Lys Ser
        130                 135                 140

Ile Ile Thr Asp Glu Thr Ala Ser Met Glu Gly Ser Pro Ser Ser Pro
145                 150                 155                 160

Phe Leu Pro Lys Pro Val Arg Leu Ile Gln Asp Leu Gln Ser Asp Phe
                165                 170                 175

Phe Gly Glu Ala Glu Thr Ser Pro Val Asp Ser Pro Leu Ser Ser Asp
            180                 185                 190

Gly Asn Ala Lys Gly Ala Ile Asp Ser Lys Leu Ser Leu Lys Leu Leu
        195                 200                 205

Gln Thr Phe Val Asp His Phe Gly Ala Cys Val Ser Ile Tyr Asn Leu
210                 215                 220

Ser Asp Ile His Asn Asp Met Lys Ala Pro Asp Ser Leu Leu Tyr Asn
225                 230                 235                 240

Thr Ala Cys Leu Leu Ala Ser Arg Tyr Val Pro Gly Ile Pro Thr Ser
                245                 250                 255

Thr Val His Ala Ile Tyr Leu Gln Val Arg His Ala Val Val Asn Ile
            260                 265                 270

Leu Trp Glu Lys Pro Pro Leu Lys Tyr Glu Thr Leu Gln Ala Leu Ala
        275                 280                 285

Leu Leu Cys Leu Trp Pro Ala Thr Ala Gln Lys Glu Pro Pro Met Asp
290                 295                 300

Ser Trp Leu Leu Ser Gly Ile Ser Ile Asn His Ala Ile Ile Ala Leu
305                 310                 315                 320

Asp Phe Leu Asn Tyr Ala Pro Ser Glu Val Met Val Asp Asn Glu Thr
                325                 330                 335

Ala Ala Gln Leu Arg Leu Trp Asn Thr Tyr Cys Leu Thr Gln Leu His
            340                 345                 350

Phe Ala Val Gly Asn Ala Arg Pro Phe His Ile Gln Gln Arg Tyr Leu
        355                 360                 365

Asp His Cys Pro Arg Ile Leu Glu His Pro Ala Ala Thr Leu Glu Asp
370                 375                 380

Ala Arg Val Val Ala Glu Ile Gln Leu Tyr Leu Met Thr Leu Arg Leu
385                 390                 395                 400

Gln Ser Asn Ser Ser Arg Met Arg Leu Ala Asp Leu Asp Tyr Glu Glu
                405                 410                 415

Ile Glu Arg Trp Lys Arg Glu Trp Ala His Leu Phe Cys Lys Lys Pro
            420                 425                 430

Val Leu Val Ser Arg Gly Leu Pro Leu Thr Arg Ala Thr Ala Gly Glu
        435                 440                 445

Ser Ser Thr Leu Glu Leu Ser Leu Trp Phe Cys Gln Thr Leu Leu His
450                 455                 460

Arg Thr Ala Met Arg Leu Gln Pro Arg Ser Asp Arg Leu Ala Ser Glu
465                 470                 475                 480

Val Leu Gln Thr Ser Arg Leu Ile Ile Ser Arg Phe Leu Gln Ile Arg
                485                 490                 495
```

```
Tyr Ser Thr Ala Leu Ser Leu Val Asp Gln Val Tyr Phe Ile Val Gly
            500                 505                 510

Tyr Ala Ala Leu Asn Leu Cys Asp Phe Asn Leu Met Asp Pro Leu Ile
            515                 520                 525

Glu Gln Val Gln Met Phe Leu His Leu Ser Pro Asn Glu Asp His
530                 535                 540

Ile Ala Tyr Arg Phe Ser Cys Met Val Ala Glu Phe Lys Arg Arg Cys
545                 550                 555                 560

Gly Ser Ala Glu Cys Asn Asp Pro Ser Ser Thr Val Lys Gly Ser Pro
                565                 570                 575

Leu Ser Ser Tyr Gly Asp Ser Arg Lys Met Ser Met Gly Gln Ala Pro
            580                 585                 590

Phe Met Pro Pro Leu Met Asp Gly Met Ile Glu Gly Tyr Gly Phe Glu
            595                 600                 605

Gln Leu Met Pro Glu Val Met Pro Ser Ser Phe Pro Asp Gly Ile Leu
610                 615                 620

Asn Gly Met Pro Val Thr Gly Leu Ala Ala Tyr Arg Ser Ala Thr Leu
625                 630                 635                 640

Ser Ser Asn Thr Arg Asp Asp Asn Leu Gln Arg Trp Phe Ser Ser Cys
                645                 650                 655

Pro Trp Ala Glu Leu Lys Pro Arg Thr Pro
            660                 665

<210> SEQ ID NO 15
<211> LENGTH: 20
<212> TYPE: DNA
<213> ORGANISM: Aspergillus niger

<400> SEQUENCE: 15
tgtgattgag gtgattggcg                                              20

<210> SEQ ID NO 16
<211> LENGTH: 20
<212> TYPE: DNA
<213> ORGANISM: Aspergillus niger

<400> SEQUENCE: 16
tcagccacac ctgcaaaggc                                              20

<210> SEQ ID NO 17
<211> LENGTH: 2443
<212> TYPE: DNA
<213> ORGANISM: Aspergillus niger
<220> FEATURE:
<221> NAME/KEY: misc_feature
<222> LOCATION: (10)..(10)
<223> OTHER INFORMATION: n=a,c,g or t

<400> SEQUENCE: 17
ctgcagaatn aatttaaact cttctgcgaa tcgcttggat tccccgcccc tggccgtaga    60
gcttaaagta tgtcccttgt cgatgcgatg tatcacaaca tataaatact agcaagggat   120
gccatgcttg gaggatagca accgacaaca tcacatcaag ctctcccttc tctgaacaat   180
aaacccacac gaaggcattt atgatggtcg cgtggtggtc tctatttctg tacggccttc   240
aggtcgcggc acctgctttg ctgcaacgc tgcggactg gcgatcgcaa tccatttatt   300
tccttctcac ggatcgattt gcaaggacgg atgggtcgac gactgcgact tgtaatactg   360
cggatcaggt gtgttgttac ctactagctt tcagaaagag gaatgtaaac tgacttgata   420
```

```
tagaaatact gtggtggaac atggcagggc atcatcgaca aggtaaattg ccccttttatc    480 aaaaaaaaag aaggaaaagc agaagaaaaa taaaataaaa agaactctag tcctaaccat    540
cacatagttg gactatatcc agggaatggg cttcacagcc atctggatca ccccgttac    600 agcccagctg ccccagacca ccgcatatgg agatgcctac catggctact ggcagcagga    660
tatgtaagtc gatttcttta aatatctacc tgtcatcttt tacatcaata tgaactaact    720
tgatggtttt agatactctc tgaacgaaaa ctacggcact gcagatgact tgaaggcgct    780
ctcttcggcc cttcatgaga ggggatgta tcttatggtc gatgtggttg ctaaccatat    840
ggttcgtggt cctttgcaac tgacttcgcg gatatggttc atttcagtac tgacaatgag    900
taatatcagg gctatgatgg agcgggtagc tcagtcgatt acagtgtgtt taaaccgttc    960
agttcccaag actacttcca cccgttctgt ttcattcaaa actatgaaga tcagactcag   1020
gttgaggatt gctggctagg agataacact gtctccttgc ctgatctcga taccaccaag   1080
gatgtggtca agaatgaatg gtacgactgg gtgggatcat tggtatcgaa ctactccagt   1140
aagatatttc tccctcattc tacaacttgg ctgatcgatg atacttacga aatcagttga   1200
cggcctccgt atcgacacag taaaacacgt ccagaaggac ttctggcccg ggtacaacaa   1260
agccgcaggc gtgtactgta tcggcgaggt gctcgacggt gatccggcct acacttgtcc   1320
ctaccagaac gtcatggacg gcgtactgaa ctatcccatg tatggttcct ccaaccatga   1380
gccttcttgc aagtctcatc tcctaacgaa acggctaaaa ccagttacta tccactcctc   1440
aacgccttca gtcaacctc cggcagcatg gacgacctct acaacatgat caacaccgtc   1500
aaatccgact gtccagactc aacactcctg ggcacattcg tcgagaacca cgacaaccca   1560
cggttcgctt cgtaagtctt ccctttatt ttccgttccc aatttccaca cagaaccca   1620 cctaacaaga gcaaagttac accaacgaca tagccctcgc caagaacgtc gcagcattca   1680
tcatcctcaa cgacggaatc cccatcatct acgccggcca agaacagcac tacgccggcg   1740
gaaacgaccc cgcgaaccgc gaagcaacct ggctctcggg ctacccgacc gacagcgagc   1800
tgtacaagtt aattgcctcc cggaacgcaa tccggaacta tgccattagc aaagatacag   1860
gattcgtgac ctacaaggta agcacaacct ctaagcatac cctaatggcc tatcttcaga   1920
gtatctgaca caagagacta atcactggca atacagaact ggcccatcta caaagacgac   1980
acaacgatcc cgatgcgcaa gggcacagat gggtcgcaga tcgtgactat cttgtccaac   2040
aagggtgctt cgggtgattc gtataccctc tccttgagtg gtgcgggtta cacagccggc   2100
cagcaattga cggaggtcat tggctgcacg accgtgacgg ttggttcgga tggaaatgtg   2160
cctgttccta tggcaggtgg gctacctagg gtattgtatc cgactgagaa gttggcaggt   2220
agcaagatct gtagtagctc gtgaagggtg gagagtatat gatggtactg ctattcaatc   2280
tggcattgga cagcgagatt gaatgtggtg gacgtaacct acgttgtgtc tgtagaatat   2340
atacatgtaa gatacatgag cttcggtgat ataatacaga agtaccatac agtaccgcgt   2400
tatggaatcg aactactaca gggctttcc tataatagac tag                      2443
```

<210> SEQ ID NO 18
<211> LENGTH: 499
<212> TYPE: PRT
<213> ORGANISM: Aspergillus niger

<400> SEQUENCE: 18

Met Met Val Ala Trp Trp Ser Leu Phe Leu Tyr Gly Leu Gln Val Ala
1               5                   10                  15

Ala Pro Ala Leu Ala Ala Thr Pro Ala Asp Trp Arg Ser Gln Ser Ile

```
            20                  25                  30
Tyr Phe Leu Leu Thr Asp Arg Phe Ala Arg Thr Asp Gly Ser Thr Thr
            35                  40                  45
Ala Thr Cys Asn Thr Ala Asp Gln Lys Tyr Cys Gly Gly Thr Trp Gln
        50                  55                  60
Gly Ile Ile Asp Lys Leu Asp Tyr Ile Gln Gly Met Gly Phe Thr Ala
65                  70                  75                  80
Ile Trp Ile Thr Pro Val Thr Ala Gln Leu Pro Gln Thr Thr Ala Tyr
                85                  90                  95
Gly Asp Ala Tyr His Gly Tyr Trp Gln Gln Asp Ile Tyr Ser Leu Asn
                100                 105                 110
Glu Asn Tyr Gly Thr Ala Asp Asp Leu Lys Ala Leu Ser Ser Ala Leu
            115                 120                 125
His Glu Arg Gly Met Tyr Leu Met Val Asp Val Val Ala Asn His Met
            130                 135                 140
Gly Tyr Asp Gly Ala Gly Ser Ser Val Asp Tyr Ser Val Phe Lys Pro
145                 150                 155                 160
Phe Ser Ser Gln Asp Tyr Phe His Pro Phe Cys Phe Ile Gln Asn Tyr
                165                 170                 175
Glu Asp Gln Thr Gln Val Glu Asp Cys Trp Leu Gly Asp Asn Thr Val
                180                 185                 190
Ser Leu Pro Asp Leu Asp Thr Thr Lys Asp Val Val Lys Asn Glu Trp
            195                 200                 205
Tyr Asp Trp Val Gly Ser Leu Val Ser Asn Tyr Ser Ile Asp Gly Leu
            210                 215                 220
Arg Ile Asp Thr Val Lys His Val Gln Lys Asp Phe Trp Pro Gly Tyr
225                 230                 235                 240
Asn Lys Ala Ala Gly Val Tyr Cys Ile Gly Glu Val Leu Asp Gly Asp
                245                 250                 255
Pro Ala Tyr Thr Cys Pro Tyr Gln Asn Val Met Asp Gly Val Leu Asn
                260                 265                 270
Tyr Pro Ile Tyr Tyr Pro Leu Leu Asn Ala Phe Lys Ser Thr Ser Gly
            275                 280                 285
Ser Met Asp Asp Leu Tyr Asn Met Ile Asn Thr Val Lys Ser Asp Cys
            290                 295                 300
Pro Asp Ser Thr Leu Leu Gly Thr Phe Val Glu Asn His Asp Asn Pro
305                 310                 315                 320
Arg Phe Ala Ser Tyr Thr Asn Asp Ile Ala Leu Ala Lys Asn Val Ala
                325                 330                 335
Ala Phe Ile Ile Leu Asn Asp Gly Ile Pro Ile Ile Tyr Ala Gly Gln
                340                 345                 350
Glu Gln His Tyr Ala Gly Gly Asn Asp Pro Ala Asn Arg Glu Ala Thr
            355                 360                 365
Trp Leu Ser Gly Tyr Pro Thr Asp Ser Glu Leu Tyr Lys Leu Ile Ala
            370                 375                 380
Ser Arg Asn Ala Ile Arg Asn Tyr Ala Ile Ser Lys Asp Thr Gly Phe
385                 390                 395                 400
Val Thr Tyr Lys Asn Trp Pro Ile Tyr Lys Asp Asp Thr Thr Ile Pro
                405                 410                 415
Met Arg Lys Gly Thr Asp Gly Ser Gln Ile Val Thr Ile Leu Ser Asn
                420                 425                 430
Lys Gly Ala Ser Gly Asp Ser Tyr Thr Leu Ser Leu Ser Gly Ala Gly
            435                 440                 445
```

Tyr Thr Ala Gly Gln Gln Leu Thr Glu Val Ile Gly Cys Thr Thr Val
            450                 455                 460

Thr Val Gly Ser Asp Gly Asn Val Pro Val Pro Met Ala Gly Gly Leu
465                 470                 475                 480

Pro Arg Val Leu Tyr Pro Thr Glu Lys Leu Ala Gly Ser Lys Ile Cys
                485                 490                 495

Ser Ser Ser

<210> SEQ ID NO 19
<211> LENGTH: 21
<212> TYPE: DNA
<213> ORGANISM: Aspergillus niger

<400> SEQUENCE: 19
ggcagcagga tatgtaagtc g                                           21

<210> SEQ ID NO 20
<211> LENGTH: 21
<212> TYPE: DNA
<213> ORGANISM: Aspergillus niger

<400> SEQUENCE: 20
cactgtaatc gactgagcta c                                           21

<210> SEQ ID NO 21
<211> LENGTH: 2520
<212> TYPE: DNA
<213> ORGANISM: Aspergillus niger
<220> FEATURE:
<221> NAME/KEY: misc_feature
<223> OTHER INFORMATION: n=a,c,g or t
<220> FEATURE:
<221> NAME/KEY: misc_feature
<222> LOCATION: (10)..(10)
<223> OTHER INFORMATION: n=a,c,g or t

<400> SEQUENCE: 21

| | | | | | |
|---|---|---|---|---|---|
| ctgcagaatn | aatttaaact | cttctgcgaa | tcgcttggat | tccccgcccc | tggccgtaga | 60 |
| gcttaaagta | tgtcccttgt | cgatgcgatg | tatcacaaca | tataaatact | agcaagggat | 120 |
| gccatgcttg | gaggatagca | accgacaaca | tcacatcaag | ctctccctc | tctgaacaat | 180 |
| aaacccaca | gaaggcattt | atgatggtcg | cgtggtggtc | tctatttctg | tacggccttc | 240 |
| aggtcgcggc | acctgctttg | gctgcaacgc | ctgcggactg | gcgatcgcaa | tccatttatt | 300 |
| tccttctcac | ggatcgattt | gcaaggacgg | atgggtcgac | gactgcgact | tgtaatactg | 360 |
| cggatcaggt | gtgttgttac | ctactagctt | tcagaaagag | gaatgtaaac | tgacttgata | 420 |
| tagaaatact | gtggtggaac | atggcagggc | atcatcgaca | aggtaaattg | cccctttatc | 480 |
| aaaaaaaaag | aaggaaaagc | agaagaaaaa | taaaataaaa | agaactctag | tcctaaccat | 540 |
| cacatagttg | gactatatcc | agggaatggg | cttcacagcc | atctggatca | ccccgttac | 600 |
| agcccagctg | ccccagacca | ccgcatatgg | agatgcctac | catggctact | ggcagcagga | 660 |
| tatgtaagtc | gatttcttta | aatatctacc | tgtcatcttt | tacatcaata | tgaactaact | 720 |
| tgatggtttt | agatactctc | tgaacgaaaa | ctacggcact | gcagatgact | tgaaggcgct | 780 |
| ctcttcggcc | cttcatgaga | gggggatgta | tcttatggtc | gatgtggttg | ctaaccatat | 840 |
| ggttcgtggt | cctttgcaac | tgacttcgcg | gatatggttc | atttcagtac | tgacaatgag | 900 |
| taatatcagg | gctatgatgg | agcgggtagc | tcagtcgatt | acagtgtgtt | taaaccgttc | 960 |
| agttcccaag | actacttcca | cccgttctgt | ttcattcaaa | actatgaaga | tcagactcag | 1020 |

-continued

```
gttgaggatt gctggctagg agataacact gtctccttgc ctgatctcga taccaccaag    1080
gatgtggtca agaatgaatg gtacgactgg gtgggatcat tggtatcgaa ctactccagt    1140
aagatatttc tccctcattc tacaacttgg ctgatcgatg atacttacga aatcagttga    1200
cggcctccgt atcgacacag taaaacacgt ccagaaggac ttctggcccg ggtacaacaa    1260
agccgcaggc gtgtactgta tcggcgaggt gctcgacggt gatccggcct acacttgtcc    1320
ctaccagaac gtcatggacg gcgtactgaa ctatcccatg tatggttcct ccaaccatga    1380
gccttcttgc aagtctcatc tcctaacgaa acggctaaaa ccagttacta tccactcctc    1440
aacgccttca gtcaacctc cggcagcatg gacgacctct acaacatgat caacaccgtc    1500
aaatccgact gtccagactc aacactcctg gcacattcg tcgagaacca cgacaaccca    1560
cggttcgctt cgtaagtctt ccctttatt ttccgttccc aatttccaca cagaaccccca    1620 cctaacaaga gcaaagttac accaacgaca tagccctcgc caagaacgtc gcagcattca    1680
tcatcctcaa cgacggaatc cccatcatct acgccggcca agaacagcac tacgccggcg    1740
gaaacgaccc cgcgaaccgc gaagcaacct ggctctcggg ctacccgacc gacagcgagc    1800
tgtacaagtt aattgcctcc cggaacgcaa tccggaacta tgccattagc aaagatacag    1860
gattcgtgac ctacaaggta agcacaacct ctaagcatac cctaatggcc tatcttcaga    1920
gtatctgaca caagagacta atcactggca atacagaact ggcccatcta caaagacgac    1980
acaacgatcc cgatgcgcaa gggcacagat gggtcgcaga tcgtgactat cttgtccaac    2040
aagggtgctt cgggtgattc gtataccctc tccttgagtg gtgcgggtta cacagccggc    2100
cagcaattga cggaggtcat tggctgcacg accgtgacgg ttggttcgga tggaaatgtg    2160
cctgttccta tggcaggtgg gctacctagg gtattgtatc cgactgagaa gttggcaggt    2220
agcaagatct gttacggctg agcagtcaag ctcaagtccc aactgtattg actctgttga    2280
ctattcctgg gtctccttag atgatgcagt tggaggaata tgccaattgg cacttgtcgc    2340
gtgttggccg tgagatttat agagaccata ttaaaaaagc acgtgatgtg gcgttggaaa    2400
atggattaga ccttcaacag gtttcgaagg aagacccaga cttcttcgtc aagcaagggg    2460
tgataattgg tgtcgcacgc cggttcgtta gcgacattag agattgggcc aaccaataca    2520
```

<210> SEQ ID NO 22
<211> LENGTH: 498
<212> TYPE: PRT
<213> ORGANISM: Aspergillus niger

<400> SEQUENCE: 22

Met Met Val Ala Trp Trp Ser Leu Phe Leu Tyr Gly Leu Gln Val Ala
1               5                   10                  15

Ala Pro Ala Leu Ala Ala Thr Pro Ala Asp Trp Arg Ser Gln Ser Ile
            20                  25                  30

Tyr Phe Leu Leu Thr Asp Arg Phe Ala Arg Thr Asp Gly Ser Thr Thr
        35                  40                  45

Ala Thr Cys Asn Thr Ala Asp Gln Lys Tyr Cys Gly Gly Thr Trp Gln
    50                  55                  60

Gly Ile Ile Asp Lys Leu Asp Tyr Ile Gln Gly Met Gly Phe Thr Ala
65                  70                  75                  80

Ile Trp Ile Thr Pro Val Thr Ala Gln Leu Pro Gln Thr Thr Ala Tyr
                85                  90                  95

Gly Asp Ala Tyr His Gly Tyr Trp Gln Gln Asp Ile Tyr Ser Leu Asn
            100                 105                 110

Glu Asn Tyr Gly Thr Ala Asp Asp Leu Lys Ala Leu Ser Ser Ala Leu

```
                    115                 120                 125
His Glu Arg Gly Met Tyr Leu Met Val Asp Val Ala Asn His Met
130                 135                 140

Gly Tyr Asp Gly Ala Gly Ser Ser Val Asp Tyr Ser Val Phe Lys Pro
145                 150                 155                 160

Phe Ser Ser Gln Asp Tyr Phe His Pro Phe Cys Phe Ile Gln Asn Tyr
                165                 170                 175

Glu Asp Gln Thr Gln Val Glu Asp Cys Trp Leu Gly Asp Asn Thr Val
            180                 185                 190

Ser Leu Pro Asp Leu Asp Thr Thr Lys Asp Val Val Lys Asn Glu Trp
        195                 200                 205

Tyr Asp Trp Val Gly Ser Leu Val Ser Asn Tyr Ser Ile Asp Gly Leu
210                 215                 220

Arg Ile Asp Thr Val Lys His Val Gln Lys Asp Phe Trp Pro Gly Tyr
225                 230                 235                 240

Asn Lys Ala Ala Gly Val Tyr Cys Ile Gly Glu Val Leu Asp Gly Asp
                245                 250                 255

Pro Ala Tyr Thr Cys Pro Tyr Gln Asn Val Met Asp Gly Val Leu Asn
            260                 265                 270

Tyr Pro Ile Tyr Tyr Pro Leu Leu Asn Ala Phe Lys Ser Thr Ser Gly
        275                 280                 285

Ser Met Asp Asp Leu Tyr Asn Met Ile Asn Thr Val Lys Ser Asp Cys
290                 295                 300

Pro Asp Ser Thr Leu Leu Gly Thr Phe Val Glu Asn His Asp Asn Pro
305                 310                 315                 320

Arg Phe Ala Ser Tyr Thr Asn Asp Ile Ala Leu Ala Lys Asn Val Ala
                325                 330                 335

Ala Phe Ile Ile Leu Asn Asp Gly Ile Pro Ile Ile Tyr Ala Gly Gln
            340                 345                 350

Glu Gln His Tyr Ala Gly Gly Asn Asp Pro Ala Asn Arg Glu Ala Thr
        355                 360                 365

Trp Leu Ser Gly Tyr Pro Thr Asp Ser Glu Leu Tyr Lys Leu Ile Ala
370                 375                 380

Ser Arg Asn Ala Ile Arg Asn Tyr Ala Ile Ser Lys Asp Thr Gly Phe
385                 390                 395                 400

Val Thr Tyr Lys Asn Trp Pro Ile Tyr Lys Asp Asp Thr Thr Ile Pro
                405                 410                 415

Met Arg Lys Gly Thr Asp Gly Ser Gln Ile Val Thr Ile Leu Ser Asn
            420                 425                 430

Lys Gly Ala Ser Gly Asp Ser Tyr Thr Leu Ser Leu Ser Gly Ala Gly
        435                 440                 445

Tyr Thr Ala Gly Gln Gln Leu Thr Glu Val Ile Gly Cys Thr Thr Val
450                 455                 460

Thr Val Gly Ser Asp Gly Asn Val Pro Val Pro Met Ala Gly Gly Leu
465                 470                 475                 480

Pro Arg Val Leu Tyr Pro Thr Glu Lys Leu Ala Gly Ser Lys Ile Cys
                485                 490                 495

Tyr Gly

<210> SEQ ID NO 23
<211> LENGTH: 3494
<212> TYPE: DNA
<213> ORGANISM: Aspergillus niger
<220> FEATURE:
<221> NAME/KEY: misc_feature
```

<222> LOCATION: (3370)..(3370)
<223> OTHER INFORMATION: n=a,c,g or t

<400> SEQUENCE: 23

```
tgctccctcg gccaagcgcc aataacgtcc gattcatccc attcctcgtc cagctggcga      60
actccggagg ttgattgctc gctcgctctc agttggccac caaacttact cgtccccctc     120
cttcaccctc cctcctctgc caatgctaca gagtacttgg ctaggctact atcttctcag     180
ctgggtgaag aacaacgggc cccgtgcgtg atgagcaaaa gcgtctgaca tgcagcaact     240
gcagtatact ggagcccgcg gctaccgagg aactcgtgct cgtgtgccac cacatcgaag     300
tgagttgatg cgtcttgtcc atgcagtgtc ggcgtggcct aaagtacggg ccaaacctgt     360
ctgacttcat cccacactat taccccctcc ctcattctcc cctgattcgg cccaataagg     420
aaatcactta gtcaatcaat cctgccatta ccggcgcgta atctgaaact acgcgcggac     480
tgtctcttac tcccctcgcg gtgggcggcc cagccagccc catccttact agatttagcg     540
aattactggt cattagccct gtacggggga ggggcggaa acaaaaatg cgaataatag      600
aataaattta ataaagaaaa aagaggggg ggagcttat ctaggccct gctgcattgc       660
attcggacat ttttcgactt gtcacaggca caaatcatag tccgccgatg gcgtcgattg     720
accatttcct tttcttttct cggcgctggg atggtggcca agaaaattga atggcaatgg     780
ttcgttcacc ggagtagggt gtacgtgcat tgtgtggatt gacgatgatt ctcggccaag     840
ggcttgcgtt gcaatcccac caggagggga atgttgcaga cagacagaaa gcaaagaag      900
tattggaggg aaaaaaacaa ttcttgaaaa atgatcttct caggtaatga atattggttg     960
ctggcgggct gatcttctcc cgacacgtct atataaactg gtcaccttct ggcccttcct    1020
ttctatctct tccttctcat catcagtctc aaacaagcct cttctctcc taccttcact     1080
ctccactttc tccttcgaa agggataaaa ctctcctcct cattctcacc tatatatacc     1140
ttgtgctttt ctcgcaatga agttgatac ccccgattct gcttccacca tcagcatgac    1200
caacactatc accatcaccg tagagcagga cggtatctat gagatcaacg gtgcccgtca    1260
agagcccgtg gtcaacctga acatggtcac cggtgcgagc aaactgcgca agcagcttcg    1320
cgagaccaat gagttgctcg tgtgtcctgg tgtgtacgac ggtctgtccg cccgtattgc    1380
catcaacctg ggcttcaagg gcatgtacat ggtatgttgg attccttaga ctacctttcc    1440
ccacagtcaa cacttctccg cttccgcgat ggagaaaaaa gatcatacta acggaaaggt    1500
cagaccggcg ccggtactac cgcgtctaga ctgggcatgg ccgatctggg tctagcccac    1560
atctacgaca tgaagaccaa cgcagagatg atcgcgaacc tggacccca cggtcctccc    1620
ctgatcgcag acatggacac tggctacgga ggtgagaatc ccccatctcc actgtctgcc    1680
aagacataat gatctacccg cgccaaaaag caaaacggca atatagaccc agttccccac    1740
taacaccaaa aaaacaaaaa taggccccct gatggtcgcc cgttccgttc aacaatacat    1800
ccaagccgga gtcgcgggat ccacatcga agatcagatc caaaacaagc gatgcggaca     1860
cctggcaggc aagcgcgtcg tcaccatgga cgaatacttg actcgcatcc gcgccgccaa    1920
gctcaccaag gaccgcctcc gcagcgacat cgtgctgatt gcccgcaccg acgccctcca    1980
gcagcacggc tacgacgagt gcattcgccg ccttaaggcc gcccgcgatc ttggcgccga    2040
tgttggtctc ctcgagggct tcaccagtaa ggagatggca aggcggtgtg tccaggacct    2100
tgcgccttgg ccgcttctgc tcaacatggt ggagaacggt gctgggcggt ttatttccgt    2160
cgatgaggct agggaaatgg gcttccgcat tatgatcttc tcgttcgctt gcattactcc    2220
tgcctatatg gggattaccg ctgctctgga gaggctcaag aaggatggtg tggttgggtt    2280
```

```
gcccgagggg atgggaccga agaagctgtt tgaggtgtgc ggattgatgg actcggtgag    2340
ggttgatacc gaggctggtg gagatgggtt tgctaatggt gtttaattct tttcttttt    2400
tgattcttaa ttccctggtt gttttgttgt gaaagtttct tattttctg gtttgtttta    2460
tttccccttc tggtaactaa ttttgtgtga gaaagagttg ttgagttggg ttgaactgca    2520
ttggatggga ttgatttatt ttcgggatca aagtgaaagg aagggaaggg ggctgtgtta    2580
ttggttttcg agtggggacc gatatattcc tactatacat atcgaagctt gcgtggtaca    2640
tatactagta tctactacat taccaagaat ggaaatgaaa actgggtgtt agatttcagt    2700
tgacaggtct tatgttcgtt taccgataga gtaattcctg cttctcactc catgtgagcc    2760
caatcacaat ggaattgtaa tctggttgcc ttataagtac ttagtactct gtactctgta    2820
ctacttctcg catcacatca aatcttaata cttagtacgt agtttgtttc acccagcaaa    2880
accttattgc cttaacaatc atattctcag taagcacgag acacagaaac gagagaagta    2940
ttctagaccc tgacagaacw ccctgatcga cagtcactta cccaacaaag taagtggtct    3000
ctaccctctg attacagtta aggcaggcag tagtaagcaa gaagaagaaa gaagaataa    3060
ttaactacta agtttctcac tactgcatgc acgaccacgg agtcgccgtg caaaaaaatt    3120
ggtgcgtgct cagctagctg cactctgcac actgccaccc tcgccctaca aagaaacca    3180
tgctgtttct ccactatact gttcccgcga tgaaactagg gccaataacc atgcagttac    3240
tattggtccc actggggtgg gttgggtagc cttatggtat taaaaggagt aggggtcttt    3300
gtcgatcgtt ttctgttttc tttttgkatt tttatttytg ttggwctctg tttgtgttgt    3360
gttgggccgn ttttgttttc tttgggtaac gagggatggg aatatattca tatggaaatg    3420
gaaatggatt atgctattga ttgatgaatg gtgatgatct gcgtggaaat taatgtcaga    3480
gtcttgmtga ttca                                                      3494

<210> SEQ ID NO 24
<211> LENGTH: 341
<212> TYPE: PRT
<213> ORGANISM: Aspergillus niger

<400> SEQUENCE: 24

Met Lys Val Asp Thr Pro Asp Ser Ala Ser Thr Ile Ser Met Thr Asn
1               5                   10                  15

Thr Ile Thr Ile Thr Val Glu Gln Asp Gly Ile Tyr Glu Ile Asn Gly
            20                  25                  30

Ala Arg Gln Glu Pro Val Val Asn Leu Asn Met Val Thr Gly Ala Ser
        35                  40                  45

Lys Leu Arg Lys Gln Leu Arg Glu Thr Asn Glu Leu Leu Val Cys Pro
    50                  55                  60

Gly Val Tyr Asp Gly Leu Ser Ala Arg Ile Ala Ile Asn Leu Gly Phe
65                  70                  75                  80

Lys Gly Met Tyr Met Thr Gly Ala Gly Thr Thr Ala Ser Arg Leu Gly
                85                  90                  95

Met Ala Asp Leu Gly Leu Ala His Ile Tyr Asp Met Lys Thr Asn Ala
            100                 105                 110

Glu Met Ile Ala Asn Leu Asp Pro Tyr Gly Pro Leu Ile Ala Asp
        115                 120                 125

Met Asp Thr Gly Tyr Gly Gly Pro Leu Met Val Ala Arg Ser Val Gln
    130                 135                 140

Gln Tyr Ile Gln Ala Gly Val Ala Gly Phe His Ile Glu Asp Gln Ile
145                 150                 155                 160
```

-continued

```
Gln Asn Lys Arg Cys Gly His Leu Ala Gly Lys Arg Val Val Thr Met
                165                 170                 175
Asp Glu Tyr Leu Thr Arg Ile Arg Ala Ala Lys Leu Thr Lys Asp Arg
            180                 185                 190
Leu Arg Ser Asp Ile Val Leu Ile Ala Arg Thr Asp Ala Leu Gln Gln
        195                 200                 205
His Gly Tyr Asp Glu Cys Ile Arg Arg Leu Lys Ala Ala Arg Asp Leu
    210                 215                 220
Gly Ala Asp Val Gly Leu Leu Glu Gly Phe Thr Ser Lys Glu Met Ala
225                 230                 235                 240
Arg Arg Cys Val Gln Asp Leu Ala Pro Trp Pro Leu Leu Leu Asn Met
                245                 250                 255
Val Glu Asn Gly Ala Gly Pro Val Ile Ser Val Asp Glu Ala Arg Glu
            260                 265                 270
Met Gly Phe Arg Ile Met Ile Phe Ser Phe Ala Cys Ile Thr Pro Ala
        275                 280                 285
Tyr Met Gly Ile Thr Ala Ala Leu Glu Arg Leu Lys Lys Asp Gly Val
    290                 295                 300
Val Gly Leu Pro Glu Gly Met Gly Pro Lys Lys Leu Phe Glu Val Cys
305                 310                 315                 320
Gly Leu Met Asp Ser Val Arg Val Asp Thr Glu Ala Gly Gly Asp Gly
                325                 330                 335
Phe Ala Asn Gly Val
            340

<210> SEQ ID NO 25
<211> LENGTH: 21
<212> TYPE: DNA
<213> ORGANISM: Aspergillus niger

<400> SEQUENCE: 25
ctacgacatg aagaccaacg c                                            21

<210> SEQ ID NO 26
<211> LENGTH: 21
<212> TYPE: DNA
<213> ORGANISM: Aspergillus niger

<400> SEQUENCE: 26
gcaccgttct ccaccatgtt g                                            21

<210> SEQ ID NO 27
<211> LENGTH: 1389
<212> TYPE: DNA
<213> ORGANISM: Candida antarctica

<400> SEQUENCE: 27
atgcgagtgt ccttgcgctc catcacgtcg ctgcttgcgg cggcaacggc ggctgtgctc       60
gcggctccgg cggccgagac gctggaccga cgggcggcgc tgcccaaccc ctacgacgat      120
cccttctaca cgacgccatc caacatcggc acgtttgcca agggcaggt gatccaatct       180 cgcaaggtgc ccacggacat cggcaacgcc aacaacgctg cgtcgttcca gctgcagtac      240
cgcaccacca atacgcagaa cgaggcggtg gccgacgtgg ccaccgtgtg gatcccggcc      300
aagcccgctt cgccgcccaa gatcttttcg taccaggtct acgaggatgc cacggcgctc      360
gactgtgctc cgagctacag ctacctcact ggattggacc agccgaacaa ggtgacggcg      420
gtgctcgaca cgcccatcat catcggctgg gcgctgcagc agggctacta cgtcgtctcg      480
```

```
tccgaccacg aaggcttcaa agccgccttc atcgctggct acgaagaggg catggctatc    540
ctcgacggca tccgcgcgct caagaactac cagaacctgc catccgacag caaggtcgct    600
cttgagggct acagtggcgg agctcacgcc accgtgtggg cgacttcgct tgctgaatcg    660
tacgcgcccg agctcaacat tgtcggtgct tcgcacggcg gcacgcccgt gagcgccaag    720 gacacccttta cattcctcaa cggcggaccc ttcgccggct tgccctggc gggtgtttcg    780 ggtctctcgc tcgctcatcc tgatatggag agcttcattg aggcccgatt gaacgccaag    840
ggtcagcgga cgctcaagca gatccgcggc cgtggcttct gcctgccgca ggtggtgttg    900
acctacccct tcctcaacgt cttctcgctg gtcaacgaca cgaacctgct gaatgaggcg    960
ccgatcgcta gcatcctcaa gcaggagact gtggtccagg ccgaagcgag ctacacggta   1020
tcggtgccca agttcccgcg cttcatctgg catgcgatcc ccgacgagat cgtgccgtac   1080
cagcctgcgg ctacctacgt caaggagcaa tgtgccaagg cgccaacat caattttcg     1140 ccctacccga tcgccgagca cctcaccgcc gagatctttg gtctggtgcc tagcctgtgg   1200
tttatcaagc aagccttcga cggcaccaca cccaaggtga tctgcggcac tcccatccct   1260
gctatcgctg gcatcaccac gccctcggcg gaccaagtgc tgggttcgga cctggccaac   1320
cagctgcgca gcctcgacgg caagcagagt gcgttcggca agcctttgg ccccatcaca   1380 ccaccttag                                                          1389

<210> SEQ ID NO 28
<211> LENGTH: 462
<212> TYPE: PRT
<213> ORGANISM: Candida antarctica

<400> SEQUENCE: 28

Met Arg Val Ser Leu Arg Ser Ile Thr Ser Leu Leu Ala Ala Ala Thr
1               5                   10                  15

Ala Ala Val Leu Ala Ala Pro Ala Glu Thr Leu Asp Arg Arg Ala
            20                  25                  30

Ala Leu Pro Asn Pro Tyr Asp Asp Pro Phe Tyr Thr Thr Pro Ser Asn
        35                  40                  45

Ile Gly Thr Phe Ala Lys Gly Gln Val Ile Gln Ser Arg Lys Val Pro
    50                  55                  60

Thr Asp Ile Gly Asn Ala Asn Asn Ala Ala Ser Phe Gln Leu Gln Tyr
65                  70                  75                  80

Arg Thr Thr Asn Thr Gln Asn Glu Ala Val Ala Asp Val Ala Thr Val
                85                  90                  95

Trp Ile Pro Ala Lys Pro Ala Ser Pro Pro Lys Ile Phe Ser Tyr Gln
            100                 105                 110

Val Tyr Glu Asp Ala Thr Ala Leu Asp Cys Ala Pro Ser Tyr Ser Tyr
        115                 120                 125

Leu Thr Gly Leu Asp Gln Pro Asn Lys Val Thr Ala Val Leu Asp Thr
    130                 135                 140

Pro Ile Ile Ile Gly Trp Ala Leu Gln Gln Gly Tyr Tyr Val Val Ser
145                 150                 155                 160

Ser Asp His Glu Gly Phe Lys Ala Ala Phe Ile Ala Gly Tyr Glu Glu
                165                 170                 175

Gly Met Ala Ile Leu Asp Gly Ile Arg Ala Leu Lys Asn Tyr Gln Asn
            180                 185                 190

Leu Pro Ser Asp Ser Lys Val Ala Leu Glu Gly Tyr Ser Gly Gly Ala
        195                 200                 205
```

```
His Ala Thr Val Trp Ala Thr Ser Leu Ala Glu Ser Tyr Ala Pro Glu
        210                 215                 220

Leu Asn Ile Val Gly Ala Ser His Gly Gly Thr Pro Val Ser Ala Lys
225                 230                 235                 240

Asp Thr Phe Thr Phe Leu Asn Gly Gly Pro Phe Ala Gly Phe Ala Leu
            245                 250                 255

Ala Gly Val Ser Gly Leu Ser Leu Ala His Pro Asp Met Glu Ser Phe
                260                 265                 270

Ile Glu Ala Arg Leu Asn Ala Lys Gly Gln Arg Thr Leu Lys Gln Ile
            275                 280                 285

Arg Gly Arg Gly Phe Cys Leu Pro Gln Val Val Leu Thr Tyr Pro Phe
290                 295                 300

Leu Asn Val Phe Ser Leu Val Asn Asp Thr Asn Leu Leu Asn Glu Ala
305                 310                 315                 320

Pro Ile Ala Ser Ile Leu Lys Gln Glu Thr Val Val Gln Ala Glu Ala
                325                 330                 335

Ser Tyr Thr Val Ser Val Pro Lys Phe Pro Arg Phe Ile Trp His Ala
                340                 345                 350

Ile Pro Asp Glu Ile Val Pro Tyr Gln Pro Ala Ala Thr Tyr Val Lys
            355                 360                 365

Glu Gln Cys Ala Lys Gly Ala Asn Ile Asn Phe Ser Pro Tyr Pro Ile
370                 375                 380

Ala Glu His Leu Thr Ala Glu Ile Phe Gly Leu Val Pro Ser Leu Trp
385                 390                 395                 400

Phe Ile Lys Gln Ala Phe Asp Gly Thr Thr Pro Lys Val Ile Cys Gly
                405                 410                 415

Thr Pro Ile Pro Ala Ile Ala Gly Ile Thr Thr Pro Ser Ala Asp Gln
            420                 425                 430

Val Leu Gly Ser Asp Leu Ala Asn Gln Leu Arg Ser Leu Asp Gly Lys
                435                 440                 445

Gln Ser Ala Phe Gly Lys Pro Phe Gly Pro Ile Thr Pro Pro
        450                 455                 460

<210> SEQ ID NO 29
<211> LENGTH: 2794
<212> TYPE: DNA
<213> ORGANISM: Scytalidum thermophilum

<400> SEQUENCE: 29
atgaacagag tcacgaatct cctcgcctgg gccggcgcga tagggctcgc ccaagcaaca      60
tgtccctttg cggaccctgc cgctctgtat agtcgtcaag atactaccag cggccagtcg     120
ccacttgcag catacgaggt ggatgacagc accggatacc tgacctccga tgttggcggg     180
cccattcagg accagaccag cctcaaggca ggcatccggg gtccgaccct tcttgaggac     240
tttatgttcc gccagaagat ccagcacttc gaccatgaac gggtaaggac ataatgctca     300
cacgagcggc tgcgtgccca cctatttccg agacattggg ctggctggct ggctgtgact     360
gcttgagttt ggggacatac ggagtaccct actgacgcgc tgaaccactc caggttcccg     420
aaagggcggt ccatgctcga ggcgctggag cacacgggac cttcacgagt tacgccgact     480
ggagtaacat caccgcggcg tcctttctga acgccactgg aaagcagacg ccggtgtttg     540
tccggttctc gaccgttgct gggtctcgag ggagcgcaga cacggcgaga acgttcatg      600 gtttcgcgac gcggtttgta agttttgttg tgtttcattc gttccggtct gtagaggagg     660
gttaggatat gagctaacgt gtgtgtgtgt gtgaagtaca ctgatgaagg caactttgta     720
```

```
cgtcccacgc atggtcctca attctcttat ctggcagcca tgtggtcatt gtcgacgttg    780
ctaacttgcg taggatatcg tcggaaacaa catcccggta ttcttcattc aagatgcaat    840
ccagttccct gaccttatcc actcggtcaa gccgcgtccc gacaacgaga ttccccaagc    900
ggcgacggct catgattcag cttgggactt cttcagccag cagccaagca ccatggtaag    960
caatggacca aggagccgca cctggggtga catgccaggg agtacacaag gcgttccgat   1020
gaccctcgtg tgaccaaggc agtacaacac tccacggagg actcgaagag attcggcaat   1080
atggaacaca gaactgacag gatggtagca cacgttgttc tgggccatgt ccggccacgg   1140
aatccctcgc agctaccgcc atatggtacg tttgcctggc tgagatgacc gtgaatccat   1200
ttctaacctc aagcccagga tggcttcggc gtccacacgt tccggtttgt caaagatgac   1260
ggctcgtcca agttgatcaa gtggcatttc aagtcacgcc agggaaaggc gagtctagtc   1320
tgggaagagg cgcaggttct ttctggcaag aatgccgact ccaccgtca ggacctctgg    1380
gatgctattg agtccgggaa cggaccagaa tgggatgtct cgtccagat tgtcgatgag    1440
tcccaggcgc aagcctttgg cttcgacttg ctggacccga caaagatcat ccccgaggag   1500
tacgcccct tgacgaagct gggcctcttg aagctggatc gcaatccgac caactacttc    1560
gccgagacgg agcaggtcat gttccaaccc ggtcatatcg tccgcggcat cgacttcacg   1620
gaggatcccc tgctacaggg acgcctcttt tcgtaccttg acacgcagct gaaccggaat   1680
ggcgggccca actttgagca gctgcccatc aacatgccgc gggtgccgat tcacaacaat   1740
aatcgcgacg cgccggcca gatgttcatc cacaggaaca gtatcctgt aagtgcctct    1800
tttgcctcga tcgttgtggt gccggcttgc tgacagacgc agtacactcc caacaccctg   1860
aacagtggtt atccgcggca agccaaccaa aatgccggac gcggattctt cacagcgcct   1920
ggccgtaccg ccagcggtgc cctcgtccgt gaggtgtcgc aacattcaa cgaccactgg    1980
tcgcagcccc gtctcttctt caactccctc actcccgtcg aacaacagtt cctcgtcaac   2040
gccatgcgct tcgaaatcag ccttgtgaag tcggaagaag tcaagaagaa cgtgctcacc   2100
cagctcaacc gcgtcagcca tgacgtggc gtgcgcgtgg ccgccgctat cggcctcggc    2160
gcgcccgacg cggacgacac atactaccac aacaacaaga cggctggcgt ctcaatcgtt   2220
ggaagcgggc ccttgcctac catcaagact ctccgcgtcg gcatcctggc taccacgagc   2280
gagtcgagcg cgctggatca ggcggcccag ctccgcaccc gtctggaaaa ggacgggctt   2340
gtggtcacgg ttgtggctga aacgctgcgc gaggggtag accagacgta ctcgacggcg    2400
gatgccacgg gtttcgacgg cgttgttgtt gtggacgggg cggcggcgct gtttgccagc   2460
accgcgtcgt cgccgttgtt cccgacgggc aggccgttgc agatctttgt ggacgcgtat   2520
cggtggggaa agccggtcgg tgtgtgtggt gggaagtcga gcgaggtgtt ggatgcggcg   2580
gatgttccgg aagacgggga cggggtgtat tcggaggagt cggtggacat gtttgtggag   2640
gagtttgaga aggggttggc tactttcagg gtgagtcttg atgcctttgt ttgttgtgat   2700
gttattgttt tgtttttgtct cggactttgt gaaagaatga cggactgacg tctttggtat   2760
ctagtttacc gatcggtttg ctctcgactc ttag                               2794
```

<210> SEQ ID NO 30
<211> LENGTH: 717
<212> TYPE: PRT
<213> ORGANISM: Scytalidium thermophilum

<400> SEQUENCE: 30

Met Asn Arg Val Thr Asn Leu Leu Ala Trp Ala Gly Ala Ile Gly Leu
1               5                   10                  15

```
Ala Gln Ala Thr Cys Pro Phe Ala Asp Pro Ala Ala Leu Tyr Ser Arg
             20                  25                  30

Gln Asp Thr Thr Ser Gly Gln Ser Pro Leu Ala Ala Tyr Glu Val Asp
         35                  40                  45

Asp Ser Thr Gly Tyr Leu Thr Ser Asp Val Gly Gly Pro Ile Gln Asp
 50                  55                  60

Gln Thr Ser Leu Lys Ala Gly Ile Arg Gly Pro Thr Leu Leu Glu Asp
 65                  70                  75                  80

Phe Met Phe Arg Gln Lys Ile Gln His Phe Asp His Glu Arg Val Pro
                 85                  90                  95

Glu Arg Ala Val His Ala Arg Gly Ala Gly Ala His Gly Thr Phe Thr
                100                 105                 110

Ser Tyr Ala Asp Trp Ser Asn Ile Thr Ala Ala Ser Phe Leu Asn Ala
            115                 120                 125

Thr Gly Lys Gln Thr Pro Val Phe Val Arg Phe Ser Thr Val Ala Gly
        130                 135                 140

Ser Arg Gly Ser Ala Asp Thr Ala Arg Asp Val His Gly Phe Ala Thr
145                 150                 155                 160

Arg Phe Tyr Thr Asp Glu Gly Asn Phe Asp Ile Val Gly Asn Asn Ile
                165                 170                 175

Pro Val Phe Phe Ile Gln Asp Ala Ile Gln Phe Pro Asp Leu Ile His
            180                 185                 190

Ser Val Lys Pro Arg Pro Asp Asn Glu Ile Pro Gln Ala Ala Thr Ala
        195                 200                 205

His Asp Ser Ala Trp Asp Phe Phe Ser Gln Gln Pro Ser Thr Met His
210                 215                 220

Thr Leu Phe Trp Ala Met Ser Gly His Gly Ile Pro Arg Ser Tyr Arg
225                 230                 235                 240

His Met Asp Gly Phe Gly Val His Thr Phe Arg Phe Val Lys Asp Asp
                245                 250                 255

Gly Ser Ser Lys Leu Ile Lys Trp His Phe Lys Ser Arg Gln Gly Lys
            260                 265                 270

Ala Ser Leu Val Trp Glu Glu Ala Gln Val Leu Ser Gly Lys Asn Ala
        275                 280                 285

Asp Phe His Arg Gln Asp Leu Trp Asp Ala Ile Glu Ser Gly Asn Gly
        290                 295                 300

Pro Glu Trp Asp Val Cys Val Gln Ile Val Asp Glu Ser Gln Ala Gln
305                 310                 315                 320

Ala Phe Gly Phe Asp Leu Leu Asp Pro Thr Lys Ile Ile Pro Glu Glu
                325                 330                 335

Tyr Ala Pro Leu Thr Lys Leu Gly Leu Leu Lys Leu Asp Arg Asn Pro
            340                 345                 350

Thr Asn Tyr Phe Ala Glu Thr Glu Gln Val Met Phe Gln Pro Gly His
        355                 360                 365

Ile Val Arg Gly Ile Asp Phe Thr Glu Asp Pro Leu Leu Gln Gly Arg
        370                 375                 380

Leu Phe Ser Tyr Leu Asp Thr Gln Leu Asn Arg Asn Gly Gly Pro Asn
385                 390                 395                 400

Phe Glu Gln Leu Pro Ile Asn Met Pro Arg Val Pro Ile His Asn Asn
                405                 410                 415

Asn Arg Asp Gly Ala Gly Gln Met Phe Ile His Arg Asn Lys Tyr Pro
            420                 425                 430

Tyr Thr Pro Asn Thr Leu Asn Ser Gly Tyr Pro Arg Gln Ala Asn Gln
```

```
                    435                 440                 445
Asn Ala Gly Arg Gly Phe Phe Thr Ala Pro Gly Arg Thr Ala Ser Gly
            450                 455                 460

Ala Leu Val Arg Glu Val Ser Pro Thr Phe Asn Asp His Trp Ser Gln
465                 470                 475                 480

Pro Arg Leu Phe Phe Asn Ser Leu Thr Pro Val Glu Gln Gln Phe Leu
                485                 490                 495

Val Asn Ala Met Arg Phe Glu Ile Ser Leu Val Lys Ser Glu Glu Val
                500                 505                 510

Lys Lys Asn Val Leu Thr Gln Leu Asn Arg Val Ser His Asp Val Ala
            515                 520                 525

Val Arg Val Ala Ala Ala Ile Gly Leu Gly Ala Pro Asp Ala Asp Asp
        530                 535                 540

Thr Tyr Tyr His Asn Asn Lys Thr Ala Gly Val Ser Ile Val Gly Ser
545                 550                 555                 560

Gly Pro Leu Pro Thr Ile Lys Thr Leu Arg Val Gly Ile Leu Ala Thr
                565                 570                 575

Thr Ser Glu Ser Ser Ala Leu Asp Gln Ala Ala Gln Leu Arg Thr Arg
            580                 585                 590

Leu Glu Lys Asp Gly Leu Val Val Thr Val Val Ala Glu Thr Leu Arg
        595                 600                 605

Glu Gly Val Asp Gln Thr Tyr Ser Thr Ala Asp Ala Thr Gly Phe Asp
        610                 615                 620

Gly Val Val Val Val Asp Gly Ala Ala Ala Leu Phe Ala Ser Thr Ala
625                 630                 635                 640

Ser Ser Pro Leu Phe Pro Thr Gly Arg Pro Leu Gln Ile Phe Val Asp
                645                 650                 655

Ala Tyr Arg Trp Gly Lys Pro Val Gly Val Cys Gly Gly Lys Ser Ser
            660                 665                 670

Glu Val Leu Asp Ala Ala Asp Val Pro Glu Asp Gly Asp Gly Val Tyr
            675                 680                 685

Ser Glu Glu Ser Val Asp Met Phe Val Glu Glu Phe Glu Lys Gly Leu
        690                 695                 700

Ala Thr Phe Arg Phe Thr Asp Arg Phe Ala Leu Asp Ser
705                 710                 715
```